(12) United States Patent
Kruegle et al.

(10) Patent No.: US 12,121,699 B1
(45) Date of Patent: Oct. 22, 2024

(54) SYSTEMS AND METHODS FOR MONITORING OPERATIONS OF AN INFUSION DELIVERY DEVICE USING A PRESSURE SENSOR

(71) Applicant: Embecta Corp., Parsippany, NJ (US)

(72) Inventors: Abigail H. Kruegle, Somerville, MA (US); Muzaffer Y. Ozsecen, Groton, MA (US); Mark D. Wood, Sterling, MA (US)

(73) Assignee: Embecta Corp., Parsippany, NJ (US)

( * ) Notice: Subject to any disclaimer, the term of this patent is extended or adjusted under 35 U.S.C. 154(b) by 0 days.

(21) Appl. No.: 18/655,121

(22) Filed: May 3, 2024

Related U.S. Application Data

(60) Provisional application No. 63/591,363, filed on Oct. 18, 2023, provisional application No. 63/579,399, (Continued)

(51) Int. Cl.
| | |
|---|---|
| *A61M 5/142* | (2006.01) |
| *A61M 5/145* | (2006.01) |
| *A61M 5/168* | (2006.01) |
| *A61M 5/172* | (2006.01) |
| *G16H 40/63* | (2018.01) |
| *A61M 5/14* | (2006.01) |

(52) U.S. Cl.
CPC ........ *A61M 5/172* (2013.01); *A61M 5/14248* (2013.01); *A61M 5/1452* (2013.01); *G16H 40/63* (2018.01); *A61M 2005/1402* (2013.01); *A61M 2005/1403* (2013.01); *A61M 2005/14252* (2013.01); *A61M 2205/276* (2013.01); *A61M 2205/3327* (2013.01); *A61M 2205/3331* (2013.01); *A61M 2205/3584* (2013.01); *A61M 2205/505* (2013.01); *A61M 2205/8206* (2013.01)

(58) Field of Classification Search
CPC ............... A61M 5/1452; A61M 5/172; A61M 2205/276; G16H 40/60; G16H 40/63
See application file for complete search history.

(56) References Cited

U.S. PATENT DOCUMENTS

| | | | | |
|---|---|---|---|---|
| 5,681,285 | A * | 10/1997 | Ford | G16H 40/40 604/67 |
| 8,113,244 | B2 * | 2/2012 | Kamen | A61M 5/16831 604/404 |
| 2023/0241310 | A1* | 8/2023 | Stewart | A61M 5/1684 604/152 |

FOREIGN PATENT DOCUMENTS

ES 2882900 T3 * 12/2021 ............. G16H 40/63

OTHER PUBLICATIONS

Machine translation of ES 2 882 900 T3 (Year: 2013).*

* cited by examiner

*Primary Examiner* — Laura A Bouchelle
(74) *Attorney, Agent, or Firm* — Greenberg Traurig, LLP; David J. Dykeman; Roman Fayerberg

(57) ABSTRACT

The present disclosure relates to devices, systems and processes for delivering therapeutic fluids. Embodiments disclosed herein are directed to medical devices for housing a therapeutic fluid, and methods and systems for monitoring in an infusion delivery device, using a pressure sensor of the device, one or more of: (A) fill event detection; (B) fill volume detection; (C) mechanical compliance calibration/air detection of an infusion management system after fill event and priming; (D) occlusion detection after removal of insertion seal assembly; (E) detecting fluid path deployment of an infusion delivery device; (F) monitoring for occlusion detection during pump use; and (G) detecting an empty reservoir.

20 Claims, 54 Drawing Sheets

Related U.S. Application Data filed on Aug. 29, 2023, provisional application No. 63/578,478, filed on Aug. 24, 2023, provisional application No. 63/508,665, filed on Jun. 16, 2023, provisional application No. 63/499,848, filed on May 3, 2023.

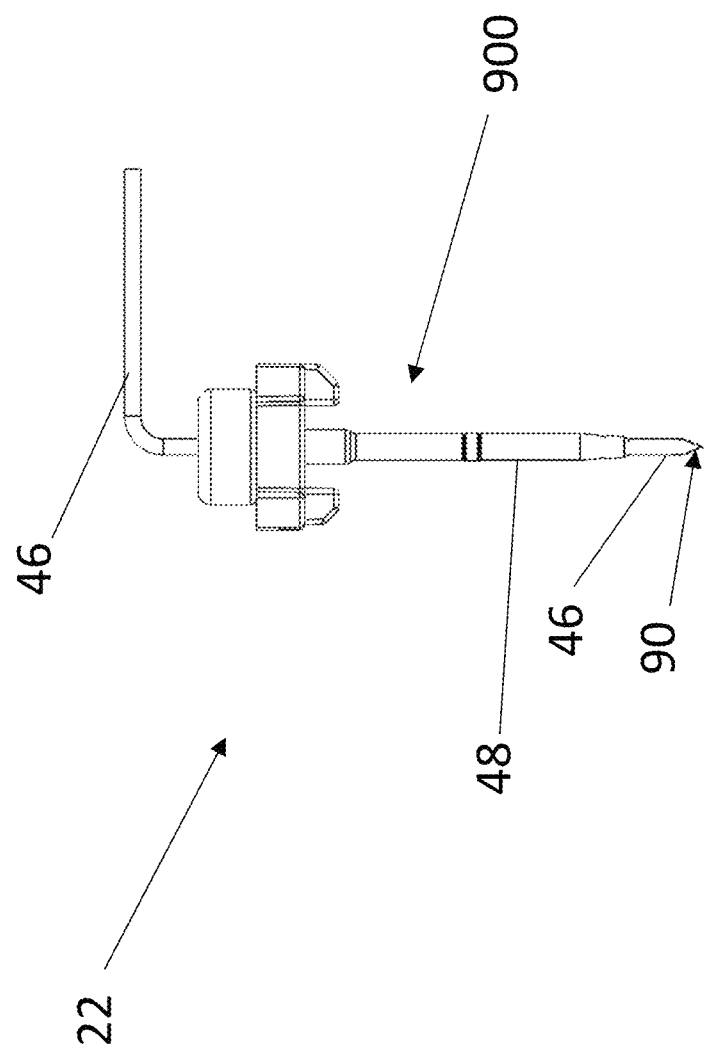

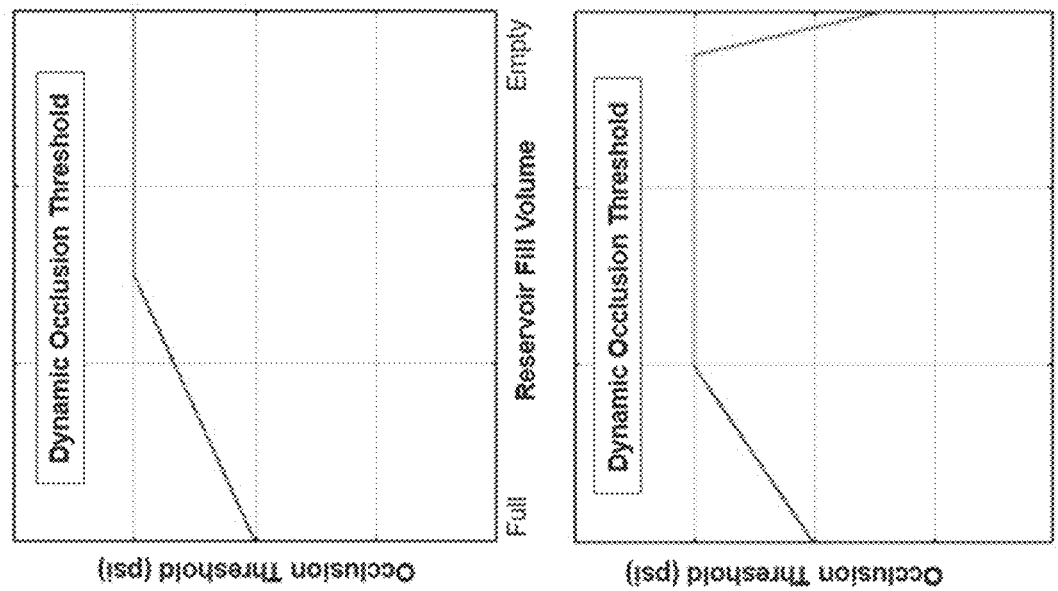
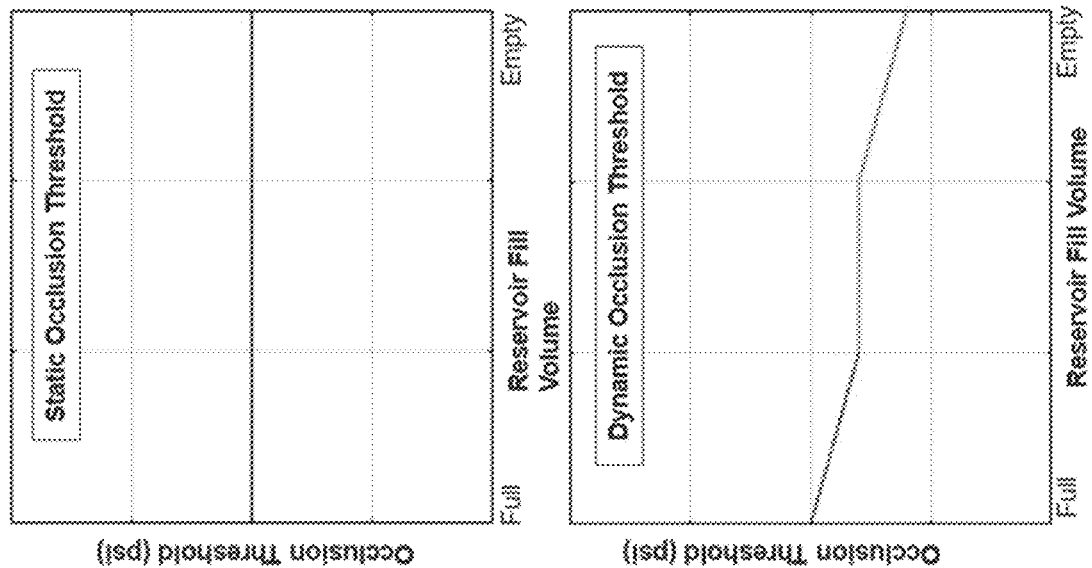
FIG. 34A
FIG. 34B
FIG. 34C
FIG. 34D

SYSTEMS AND METHODS FOR MONITORING OPERATIONS OF AN INFUSION DELIVERY DEVICE USING A PRESSURE SENSOR

CROSS-REFERENCE TO RELATED APPLICATIONS

This application claims the benefit of and priority to U.S. Provisional Application No. 63/499,848, filed on May 3, 2023, U.S. Provisional Application No. 63/508,665, filed on Jun. 16, 2023, U.S. Provisional Application No. 63/578,478, filed on Aug. 24, 2023, U.S. Provisional Application No. 63/579,399, filed on Aug. 29, 2023, and U.S. Provisional Application No. 63/591,363, filed on Oct. 18, 2023, the content of these applications are hereby incorporated herein by reference in their entirety.

FIELD

This disclosure relates to infusion delivery devices having a pressure sensor for monitoring operations of the infusion devices.

BACKGROUND

An external ambulatory infusion pump is a medical device used to deliver medicament into a patient's body in a controlled manner that is designed to be portable or wearable. There are many different types of infusion pumps, which are used for a variety of purposes and in a variety of environments. Some infusion pumps are capable of delivering medicament in small amounts and may be used to deliver nutrients or medicaments—such as insulin or other hormones, antibiotics, chemotherapy drugs and pain relievers.

Insulin pumps are a type of external ambulatory infusion pump that helps diabetic patients keep their blood glucose levels within target ranges based on individual need. Some insulin pumps include various hardware and firmware so that the diabetic patient can, for example, attach the pump to their bodies, carry an amount of insulin within a reservoir for multiple daily use, and precisely deliver appropriate amounts of insulin to the patient continuously and/or on-demand. There is still a need for reliable insulin pumps.

SUMMARY

The present disclosure relates to an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: receive pressure data detected by the at least one pressure sensor while the fluid reservoir is being filled with a therapeutic fluid so as to translate the plunger within the fluid reservoir; determine when a fill event has occurred at a first time based on the pressure data satisfying a threshold value; and prevent or allow operation of the infusion delivery device at a second time based on whether a difference between the second time and the first time exceeds a degradation time of the therapeutic fluid.

The present disclosure relates to a method including: setting a pressure threshold of an infusion delivery device, wherein the infusion delivery device includes: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; monitoring a pressure in the fluid reservoir or fluid path while the fluid reservoir is being filled with a therapeutic fluid; registering a fill event when the monitored pressure exceeds the pressure threshold and recording a first time of the fill event; and preventing or allowing operation of the infusion delivery device at a second time based on whether a difference between the second time and the first time exceeds a degradation time of the therapeutic fluid.

The present disclosure relates to an infusion management system including: an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: receive pressure data detected by the at least one pressure sensor while the fluid reservoir is being filled with a therapeutic fluid so as to translate the plunger within the fluid reservoir; determine when a fill event has occurred at a first time based on the pressure data satisfying a threshold value; and prevent or allow operation of the infusion delivery device at a second time based on whether a difference between the second time and the first time exceeds a degradation time of the therapeutic fluid; and at least one controller in communication with the infusion delivery device, wherein the at least one controller is configured to exchange data or instructions with the infusion delivery device.

The present disclosure relates to an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: record a first pressure signal when the plunger is at a first position, record a second pressure signal when the plunger is at a second position distal to the first position, calibrate a mechanical compliance (MC) value based on a difference between the first pressure signal and the second pressure signal and based on a difference between the first position and the second position, and adjust an operation of the infusion delivery device based on the MC value.

The present disclosure relates to a method for an infusion delivery device including: recording a first pressure signal when a plunger of an infusion delivery device is at a first position, wherein the infusion delivery device includes: a fluid reservoir having a proximal end, a distal end, and the plunger disposed inside the fluid reservoir and moveable therein; a fluid path in fluid communication with the fluid reservoir; and at least one pressure sensor interfacing at least one of the fluid reservoir or the fluid path; recording a second pressure signal when the plunger is at a second position distal to the first position, calibrating a mechanical compliance (MC) value based on a difference between the first pressure signal and the second pressure signal and based on a difference between the first position and the second position, and adjusting an operation of the infusion delivery device based on the MC value.

The present disclosure relates to an infusion management system including: an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: record a first pressure signal when the plunger is at a first position, record a second pressure signal when the plunger is at a second position distal to the first position, calibrate a mechanical compliance (MC) value based on a difference between the first pressure signal and the second pressure signal and based on a difference between the first position and the second position, and adjust an operation of the infusion delivery device based on the MC value; and at least one controller in communication with the infusion delivery device, wherein the at least one controller is configured to exchange data or instructions with the infusion delivery device.

The present disclosure relates to an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; a processor in communication with the at least one pressure sensor and a non-transitory computer-readable medium having encoded thereon instructions that, when executed by the processor, cause the processor to: determine whether the fluid path is in a pre-deployed configuration or a deployed configuration based on comparing pressure data collected from the at least one pressure sensor to one or more threshold values.

The present disclosure relates to a method for an infusion delivery device including: receiving pressure data from at least one pressure sensor of an infusion delivery device, wherein the infusion delivery device includes: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir and the fluid path; and determining whether the fluid path is in a pre-deployed configuration or a deployed configuration based on comparing pressure data received from the at least one pressure sensor to one or more threshold values.

The present disclosure relates to an infusion management system including: an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: determine whether the fluid path is in a pre-deployed configuration or a deployed configuration based on comparing pressure data collected from the at least one pressure sensor to one or more threshold values; and at least one controller in communication with the infusion delivery device, wherein the at least one controller is configured to exchange data or instructions with the infusion delivery device.

The present disclosure relates to an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: set a plurality of mechanical compliance (MC) values of the fluid reservoir, each MC value corresponding to a respective volume of liquid in the fluid reservoir; calculate a plurality of occlusion pressure thresholds, wherein each of the plurality of occlusion pressure thresholds is based on a respective MC value of the plurality of MC values; monitor a signal corresponding to a pressure in the fluid reservoir; and register an occlusion when the pressure exceeds an occlusion pressure threshold of the plurality of occlusion pressure thresholds, the occlusion pressure threshold corresponding to a volume of liquid in the fluid reservoir.

The present disclosure relates to a method for an infusion delivery device including: setting a plurality of mechanical compliance (MC) values of a fluid reservoir of an infusion delivery device, each MC value corresponding to a respective volume of liquid in the fluid reservoir, wherein the infusion delivery device includes: the fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; calculating a plurality of occlusion pressure thresholds, wherein each of the plurality of occlusion pressure thresholds is based on a respective MC value of the plurality of MC values; monitoring at least one signal corresponding to a pressure in the fluid reservoir; and registering an occlusion when the pressure exceeds an occlusion pressure threshold of the plurality of occlusion pressure thresholds, the occlusion pressure threshold corresponding to a volume of liquid in the fluid reservoir.

The present disclosure relates to an infusion management system including: an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: set a plurality of mechanical compliance (MC) values of the fluid reservoir, each MC value corresponding to a respective volume of liquid in the fluid reservoir; calculate a plurality of occlusion pressure thresholds, wherein each of the plurality of occlusion pressure thresholds is based on a respective MC value of the plurality of MC values; monitor at least one signal corresponding to a pressure in the fluid reservoir; and register an occlusion when the pressure exceeds an occlusion pressure threshold of the plurality of occlusion pressure thresholds, the occlusion pressure threshold corresponding to a volume of liquid in the fluid reservoir; and at least one controller in communication with the infusion delivery device, wherein the at least one controller is configured to exchange data or instructions with the infusion delivery device.

The present disclosure relates to an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: monitor one or more pressure signals; and determine an end of the fluid reservoir based on the one or more pressure signals.

The present disclosure relates to a method for an infusion delivery device including: monitoring one or more pressure signals in an infusion delivery device, wherein the infusion delivery device includes: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; and determining an end of the fluid reservoir based on one or more pressure signals.

The present disclosure relates to an infusion management system including: an infusion delivery device including: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: monitor one or more pressure signals; and determine an end of the fluid reservoir based on the one or more pressure signals; and at least one controller in communication with the infusion delivery device, wherein the at least one controller is configured to exchange data or instructions with the infusion delivery device.

BRIEF DESCRIPTION OF THE DRAWINGS

The following presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 11B is an isolated side view of fluid path components of the insertion mechanism of an exemplary IDD of the present disclosure in the pre-deployed configuration;

FIGS. 34A-34D are graphical exemplary representations of a static (i.e., constant) occlusion pressure threshold that might be used in an exemplary IDD of the present disclosure (FIG. 34A) versus dynamic occlusion pressure thresholds (FIGS. 34B-34D) that might be used in an exemplary IDD of the present disclosure;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides embodiments of (1) infusion delivery devices (IDDs) and systems (for example, including a controller), (2) methods and systems for operating embodiments of an IDD, and (3) illustrative computer systems on which such methods may be performed. In some embodiments, the present disclosure provides systems and methods for monitoring IDD operations using a pressure sensor.

I. Infusion Delivery Devices and Management Systems

Figure 1A:
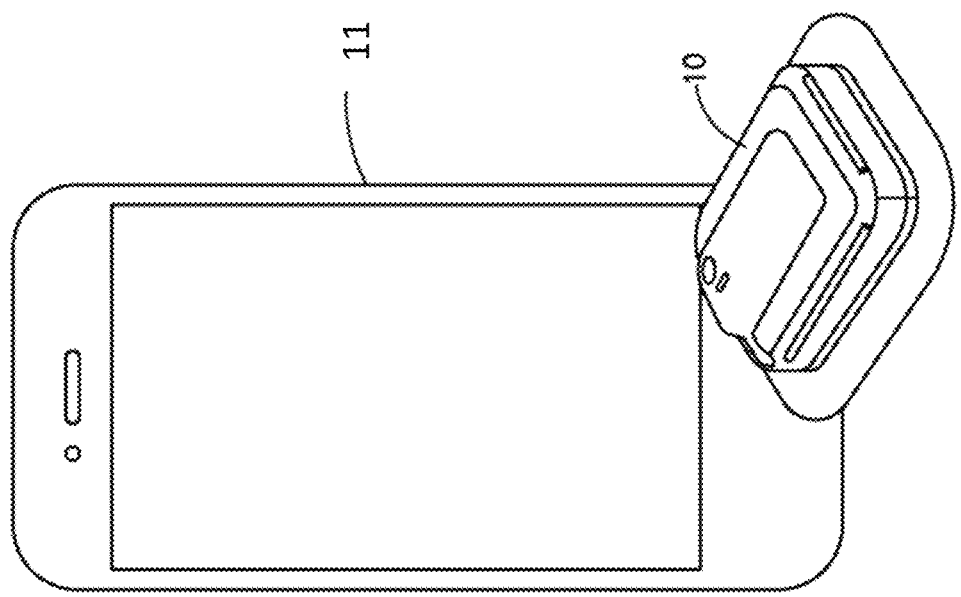
FIG. 1A shows an exemplary infusion delivery device (IDD) of the present disclosure and an optional wireless controller.
Figure 1B:
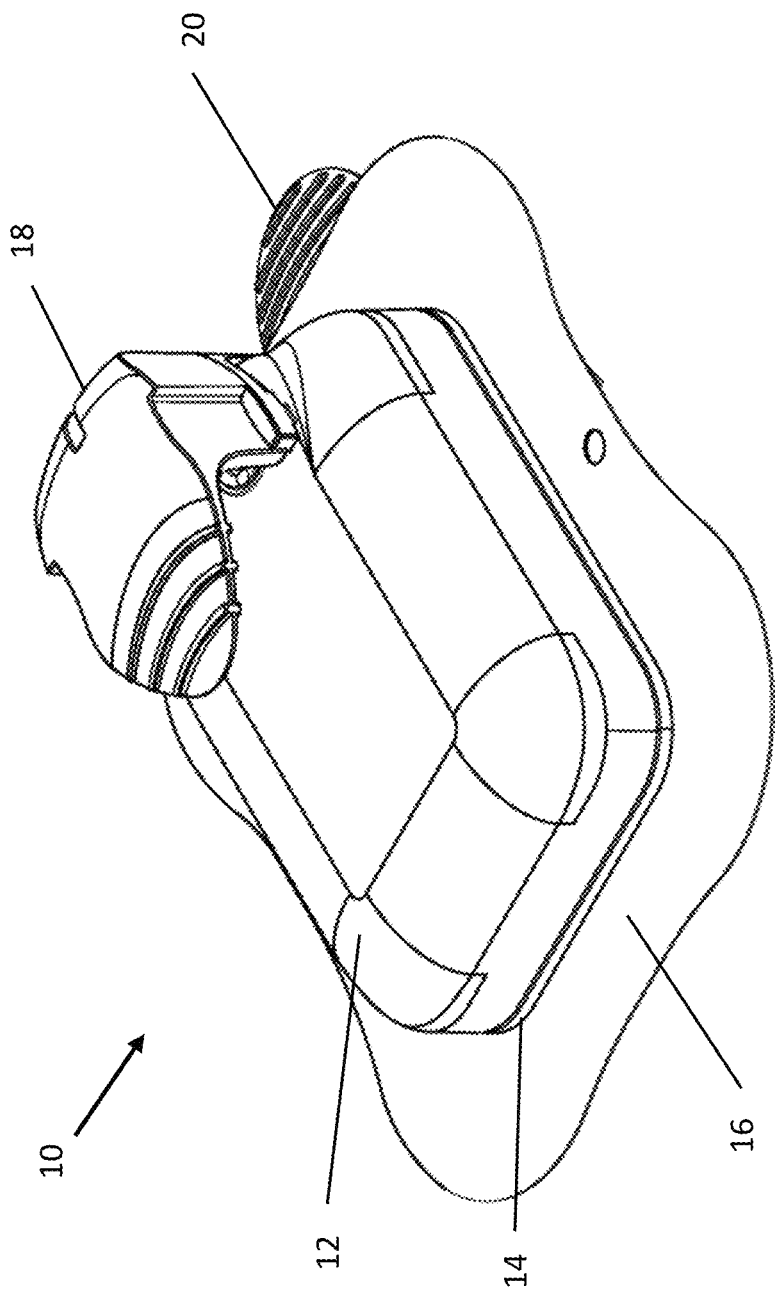
FIG. 1B shows an exemplary embodiment of a perspective view of an exemplary IDD of the present disclosure.

FIG. 1A provides an exemplary infusion delivery device (IDD) of the present disclosure and an optional wireless controller. FIG. 1B provides a perspective view of a wearable, fully disposable infusion delivery device (IDD) 10 depicted in accordance with an example embodiment of the present disclosure. In some embodiments, the IDD 10 is an insulin patch pump. Although described with respect to an insulin patch pump, the IDD 10 can be any other type of wearable or programmable medical device, such as any infusion device, configured to deliver any type of medicament or therapeutic fluid. In some embodiments, the medicament can comprise insulin or other pharmaceutical or therapeutic drug. In some embodiments, the IDD 10 can be capable of wirelessly communicating with a controller 11, such as a mobile phone, dedicated wireless remote controller (WC), or other control device, as illustrated in an embodiment in FIG. 1A. In some embodiments, the IDD 10 can include a wired controller rather than communicating with a controller remotely.

Figure 2:
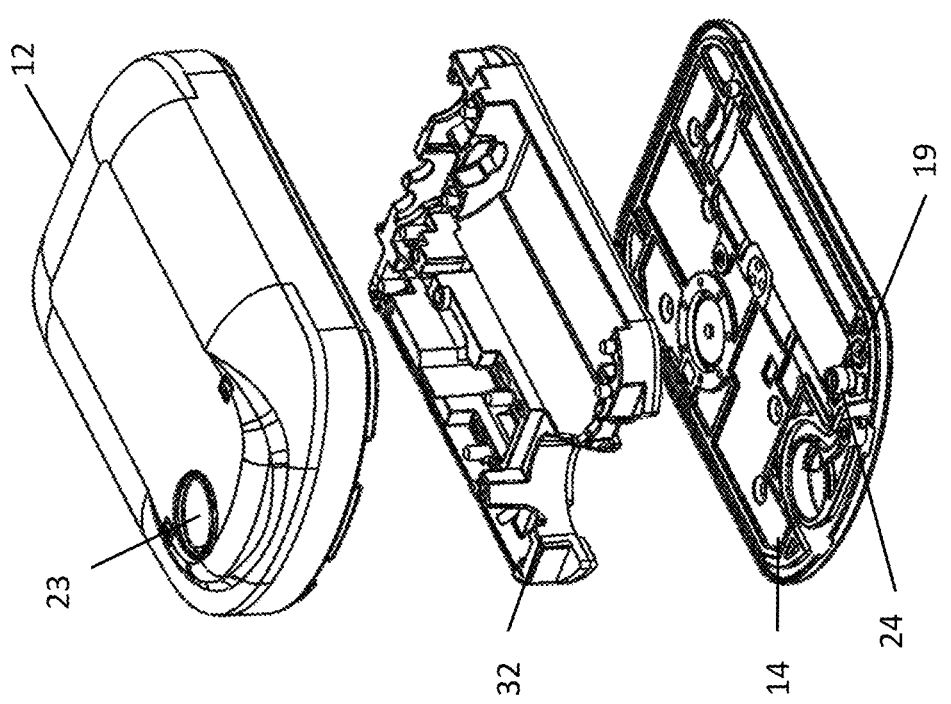
FIG. 2 is an exploded view of some of the components of an exemplary IDD of the present disclosure showing a top enclosure, a bottom enclosure, and an internal bracket superstructure.

In some embodiments, as shown in FIGS. 1B and 2, the IDD 10 includes a housing comprising a top enclosure 12 with a removable safety cover 18 and a bottom enclosure 14 with a removable adhesive patch 16 and an insertion seal assembly 20. The removable adhesive patch 16 includes one or more holes 17a, 17b and 17c. FIG. 2 is an exploded view of the IDD 10 showing a view of an internal bracket superstructure 32 configured and shaped to hold various components of the IDD 10 and positioned between the top enclosure 12 and the bottom enclosure 14 of the IDD 10. The bottom enclosure 14 includes a fill port 24. The top enclosure 12 includes a hole 23 through which a user-accessible and user-actuatable insertion mechanism 22 is configured to extend through, as shown in the exploded view of the IDD 10 in FIG. 3. The insertion mechanism 22, upon activation, inserts a catheter into the user's skin to establish a fluid path from a fluid reservoir to the user via the catheter and other components in the fluid path, described in more detail below. In some embodiments, the insertion may be vertical or close to perpendicular into the surface of the user's skin. In some embodiments, the insertion can be automated and not manually actuated by the user. To protect the user from accidentally activating the insertion mechanism 22 prematurely, the IDD 10 can include a removable safety cover 18 over the insertion mechanism 22. The insertion mechanism 22 of IDD 10 may be similar to an insertion mechanism described in U.S. patent application Ser. No. 17/838,938, which is incorporated herein by reference in its entirety. An embodiment of an insertion mechanism 22 for use in the IDD 10 is described in more detail below with respect to FIGS. 11A-11E.

Figure 3:
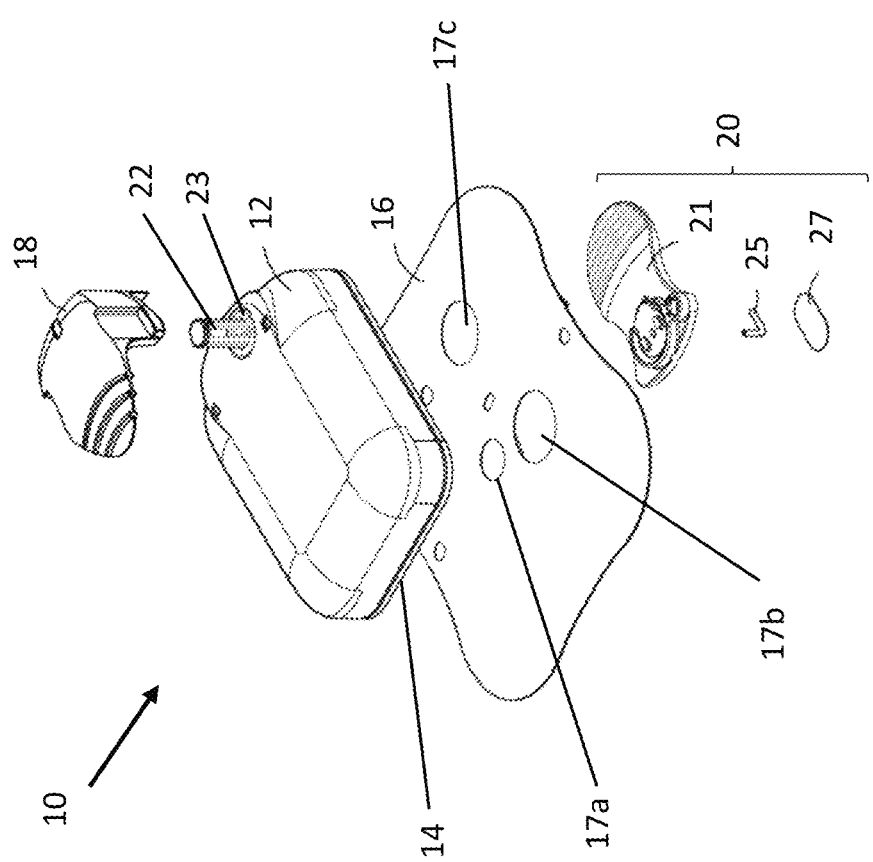
FIG. 3 is an exploded view of an exemplary IDD of the present disclosure.

The IDD 10 also includes an insertion seal assembly 20, shown in more detail in FIG. 3, that is positioned at the bottom end of the insertion mechanism 22, opposite the button end, as described below with respect to FIG. 11B. The insertion seal assembly 20 includes an insertion tab 21, an insertion tubing 25, a portion of which is retained within a slot that forms a volume used for priming the IDD 10, and a venting member 27. The insertion seal assembly 20 is positioned on the IDD 10 during the process of filling the reservoir.

In some embodiments, the venting member 27 is in fluid communication with a reservoir inside the IDD 10. In some embodiments, the venting member 27 is in the form of a hydrophobic vent material which prevents medicament from flowing out of the insertion tubing 25. In some embodiments, the insertion seal assembly 20 is removed by the user after priming, described in more detail below. A slot in the insertion tab 21 includes retaining means. In some embodiments, the distal portion of the insertion tubing 25 is bent so that it is retained within the slot. Retainers keep the insertion tubing 25 within the slot after assembly and enable the insertion tubing 25 to be removed with the insertion tab 21 when the IDD 10 has been primed and deployed. In some embodiments, barbs are used as retainers to keep the insertion tubing 25 within the slot. Any suitable method to retain the insertion tubing 25 within the slot may be used, as will be appreciated. This includes adhesive to attach the insertion tubing 25 to the inside of the slot, heat staking, mechanical lock, or any combination of attachment methods. Additionally, the insertion tubing 25 may be bent or penetrate straight through the insertion tab 21 and be attached to the insertion tab 21 using any suitable attachment method.

Figure 4:
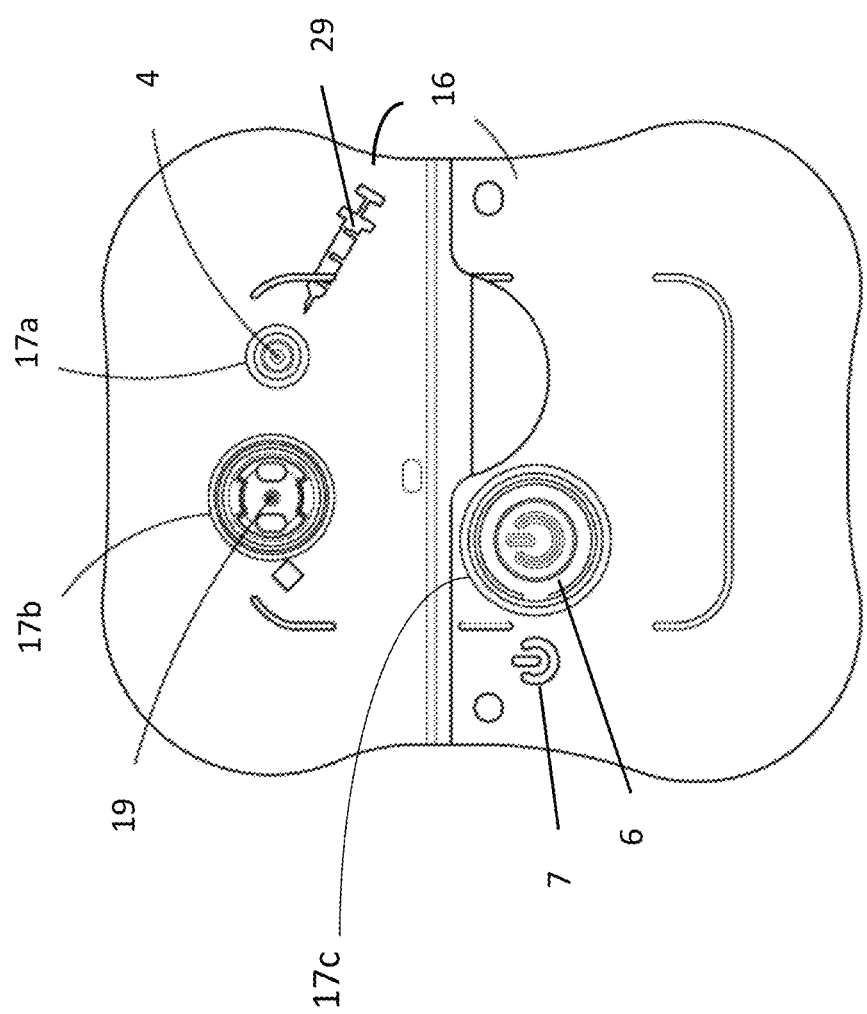
FIG. 4 is a bottom view of an exemplary IDD of the present disclosure.

FIG. 4 provides an exemplary embodiment of a bottom view of the IDD 10 depicted in FIG. 1. As shown in FIG. 4, the adhesive patch 16 includes one or more holes 17a, 17b and 17c, therethrough to expose the bottom surface of the IDD 10 to provide access to a fill port assembly that, in an embodiment, comprises a fill port 4 consisting of a small diameter hole in the bottom enclosure 14 and internal bracket assembly, the fill port 4 further comprising a fill port reducer cone 5 (see FIG. 10B), a fill port septum 26 that provides an entry into an inlet port 33 of the internal reservoir 34, and an opening 19 for access to the insertion mechanism 22, respectively, as will be explained in more detail below with respect to FIG. 5. The fill port septum 26 is used to provide a liquid seal at the reservoir inlet port 33. In some embodiments, the fill port septum 26 is concentric to the fill port 4. The fill port septum 26 is retained by the internal bracket superstructure 32 shown in FIG. 5. In some embodiments, a fill port indicia 29 may be included on the adhesive patch liner to help the user to locate the fill port 4. The bottom surface of the IDD 10 can also include an insertion opening 28 such that a catheter can extend from the bottom surface of the IDD 10 and be inserted into the skin of the patient to deliver medicament from the reservoir to the patient, as will be explained in more detail below with respect to FIG. 13. The insertion mechanism 22 may protrude through the insertion opening 19 to allow the catheter to be inserted into the user for delivery of medicament to the user. The adhesive patch 16 includes another hole 17c, which provides access to a power button 6, indicated to a user by a power button indicia 7 which might be printed on the adhesive liner, which can be depressed by the user when the user is ready to pair with, for example, a wireless controller (WC).

Figure 5:
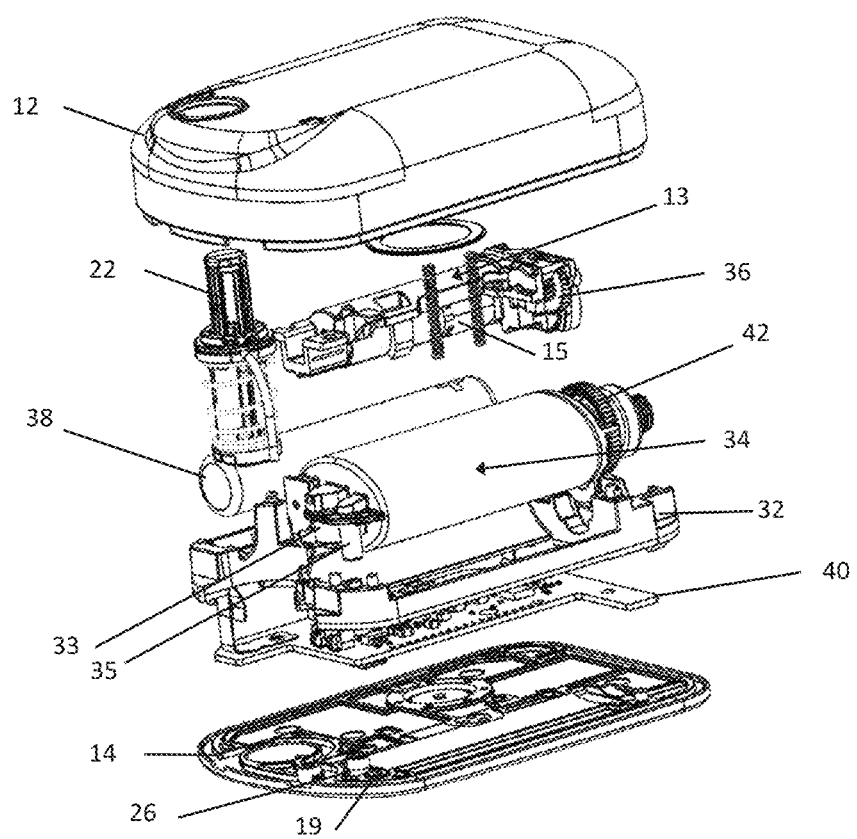
FIG. 5 is an exploded view of an exemplary IDD of the present disclosure showing exemplary internal components.

FIG. 5 illustrates an exemplary embodiment of an exploded view of the IDD 10 showing various components positioned within the top enclosure 12 and the bottom enclosure 14. A vent hole 24 is visible in the bottom enclosure 14. A hydrophobic vent membrane is positioned over the hole 24 to allow for equalization of internal pressures as well as to support EtO sterilization of the IDD 10 and provides visibility to a green LED on the PCBA 40. The additional components may comprise a reservoir 34, a motor 15 that is equipped with a planetary gearbox gearhead and interfaces with a gear train assembly 36, screw train assembly 42, a battery 38, and a printed circuit board assembly (PCBA) 40, as well as insertion mechanism 22 as previously discussed. In an embodiment, the gear train assembly 36 is maintained within a housing 13 having an end cap. The reservoir 34, the gear train assembly 36 and the battery 38 are constrained within the housing of the IDD 10 by the internal bracket superstructure 32 and top enclosure 12 (on the top half of the reservoir 34) to minimize relative motion of the components during pump operation. The PCBA 40 is disposed between the internal bracket superstructure 32 and the bottom enclosure 14. In an embodiment, the battery 38 is a single 1.5V AAAA battery.

Figure 6A:
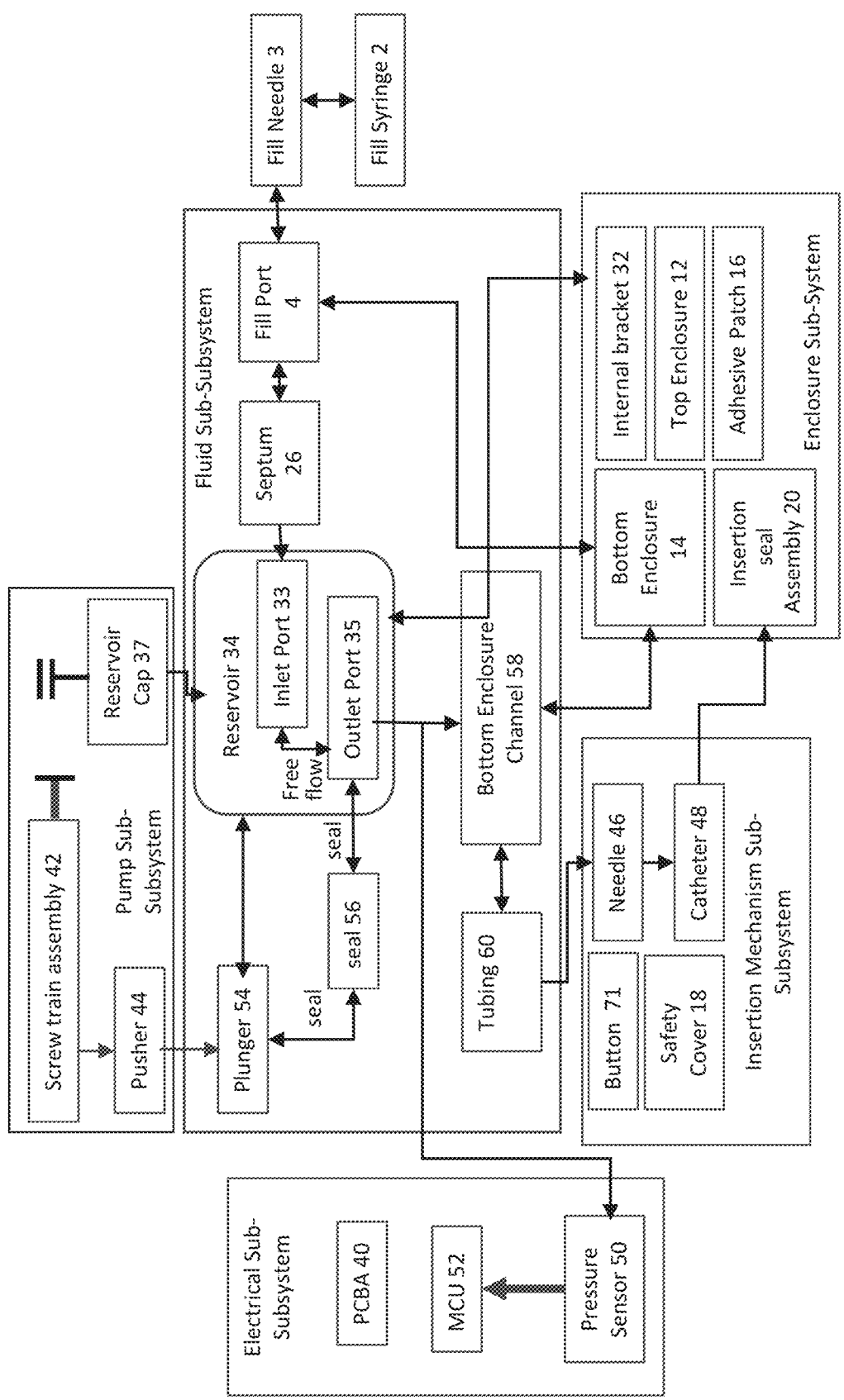
FIG. 6A is an exemplary block diagram illustrating connections between various sub-subsystem architectures of an exemplary IDD of the present disclosure.

FIG. 6A is an exemplary block diagram showing various subsystems of the IDD 10 and how the subsystems integrate with one another. The black arrows indicate an interface or communication between components, which may be one or more of a mechanical interface, a fluid interface, and an electrical interface. As shown, a fluid sub-subsystem is disposed within an enclosure sub-subsystem which includes, but is not limited to, the structure/location/retention/features (e.g., internal bracket 32/top enclosure 12/adhesive patch 16/bottom enclosure 14/insertion seal assembly 20) to support medicament fill, such as insulin or another drug, a pump sub-subsystem including a screw train assembly 42 and a pusher 44 to deliver the medicament (insulin/drug) to a patient as well as a reservoir cap 37, an insertion mechanism sub-subsystem (needle 46/catheter 48/button 71/safety cover 18), an electrical sub-subsystem (pressure sensor 50/MCU 52), and a fill syringe 2 and fill needle 3 for septum 26 penetration.

In some embodiments, the fluid sub-subsystem includes, but is not limited to, via fluidic interface, a fill port 4, a septum 26, and a reservoir 34 having an inlet port 33 and an outlet port 35. A free floating plunger 54/seal or o-rings 56 is disposed within the reservoir 34. The fluid sub-system further includes a channel 58 in the bottom enclosure 14 and tubing 60 that fluidly connect the fluid sub-system to the insertion mechanism sub-subsystem, in particular, a needle 46 and a catheter 48. In some embodiments, materials selected for use in the fluid path are sufficiently designed and qualified to support drug (e.g., insulin) stability. The reservoir 34 is configured to be filled with a medicament that is dispensed to the user via the insertion mechanism sub-subsystem. The fill port 4 is fluidically connected to the reservoir 34 so as to allow input of medicament by the user to the reservoir 34 through the inlet port 33. In some embodiments, the reservoir 34 is an oval shaped non-collapsible container used to store the medicament prior to delivery in a manner that mimics a typical syringe. In some embodiments, the reservoir 34 fluidically interfaces with the insertion mechanism sub-subsystem through the outlet port 35, the bottom enclosure channel 58, and the tubing 60 to provide fluid communication between the reservoir 34 and the insertion mechanism sub-subsystem to enable delivery of the medicament from the reservoir to the patient.

In some embodiments, the electrical sub-subsystem includes, but is not limited to, a PCBA 40 that houses and electrically interfaces many of the components of the IDD 10 including, but not limited to, integrated circuits (ICs), at least one microcontroller (MCU) 52 (with processor, memory, and input/output peripherals), a network adapter, and a pressure sensor 50. Some of the functions of the electrical sub-subsystem in conjunction with the firmware of the IDD 10 include, but are not limited to, turning the IDD 10 on/off; recognizing user input; processing data; storing data; managing power supply; sending and receiving data; priming; detecting reservoir volume; detecting occlusion; delivering insulin; and pairing/unpairing to an external device/application via Bluetooth®. In some embodiments, the electrical sub-subsystem includes, but is not limited to, a MCU with integrated Bluetooth Low Energy (BLE) capability that is used to house the main application code to control all inputs and outputs of the IDD 10. The term "Bluetooth Low Energy (BLE)" refers to a wireless communication protocol that is similar to, but independent of, traditional Bluetooth, that permits devices to communicate over short distances with lower energy. Although BLE is independent of Bluetooth, the two protocols can be supported by a single device and can use a single antenna. In some embodiments, the BLE MCU comprises a processor, a non-transitory computer-readable storage medium storing one or more programs configured for execution by a processor of the IDD 10.

An MCU of the IDD 10 can communicate with a wireless controller (WC) to exchange data and/or instructions with the IDD 10. In some embodiments, the MCU of the IDD 10 may receive information on basal and bolus dosing rates, deactivation requests and software updates as well as transmit pump health, dosing status and fault modes. In some embodiments, the electrical sub-subsystem includes, but is not limited to, a BLE chip antenna that is used to provide communication between the BLE MCU and the WC.

The pressure sensor 50 can interface with the reservoir, the fluid path or both. As such, the pressure sensor 50 can measure the pressure or change in pressure in the reservoir, the fluid path, or both, to the extent the pressures in the reservoir and the fluid path are different. Various types of pressure sensors can be used. In some embodiments, the pressure sensor 50 is configured to measure a gauge pressure.

In some embodiments, the pressure sensor 50 input interfaces with the closed end 34a of the reservoir 34 and is connected to the PCBA 40 with a flex cable 63 and connector and communicates to the BLE MCU. In some embodiments, the pressure sensor 50 is calibrated at a factory, and automatically reads a known-zero pressure reading during manufacturing to establish a set point in a controlled environment. Throughout the life of the IDD, this manufacturing pressure can be used as a reference, where the system can check that a pressure sensor reading is within a threshold of the manufacturing pressure ($P_{MFTH}$). If the $P_{MFTH}$ has been exceeded, the system may prevent further use of the IDD. In some embodiments, the pressure sensor 50 may be connected to MCU 52 via Inter-Integrated Circuit (I2C), a bus interface connection protocol for serial communication. The pressure sensor 50 measures gauge pressure, and readings are not impacted if atmospheric pressure changes. The gauge pressure is the pressure inside the reservoir or the fluid path relative to the pressure inside the IDD, outside the reservoir and/or the fluid path. The pressure inside the IDD, outside the reservoir equilibrates to atmospheric pressure within 1 psi through the bottom enclosure vent membrane.

In some embodiments, the IDD 10 includes a mechanism to ensure that the insertion seal assembly 20 is present during the filling process. For example, a magnet on the insertion tab 21 can generate a magnetic field for the electrical sub-subsystem of the IDD 10 to sense the presence of the insertion seal assembly 20 while the user is setting up the device. The magnet aligns with a sensor (not illustrated) provided on the PCBA 40 within the IDD 10. The presence of an insertion seal assembly 20 is determined by monitoring the magnetic field from a magnet embedded into the insertion seal assembly 20. This sensor is used to measure binary status of the accompanying signal. The signal processed from this sensor is later used by firmware to check if fill detect and priming processes can progress safely. While a magnet and magnet sensor, such as a Hall effect sensor are described as the mechanism to sense the presence of the insertion seal assembly 20 on the IDD 10 bottom enclosure 14, the embodiments are not so limited. Any suitable sensing mechanism could be used instead, including a photosensor, a mechanical switch, or any other sensing method.

Figure 6B:
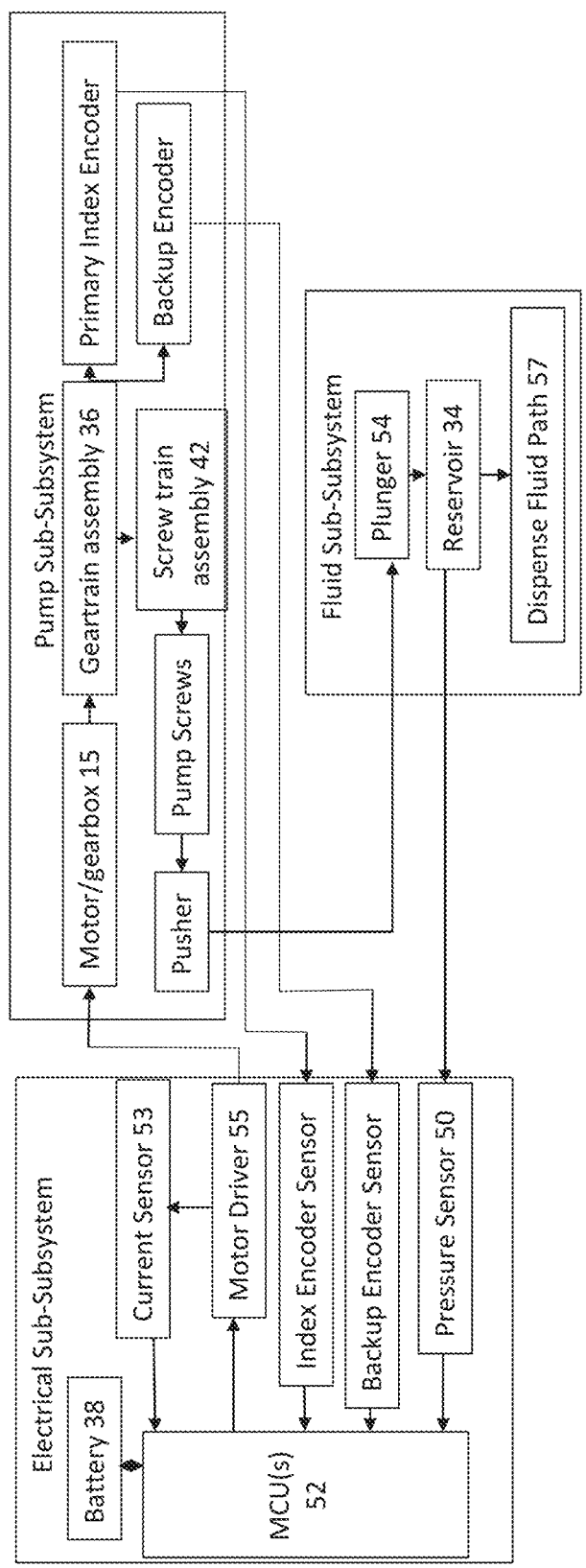
FIG. 6B is an exemplary block diagram illustrating possible connections between various sub-subsystem architectures of an exemplary IDD of the present disclosure.

FIG. 6B shows some additional features of various sub-systems of the IDD 10 and how the subsystems integrate with one another, and more specifically an electrical sub-subsystem, a pump sub-subsystem, and a fluid sub-subsystem.

In some embodiments, the fluid sub-system can include the reservoir 34, the plunger 54, and a dispense fluid path 57 that connects the reservoir to the patient. In this manner, in operation, the plunger is advanced in a distal direction within the reservoir, which expels the medicament from the reservoir 34 into the dispense fluid path 57 and causes the administration of the medicament to the patient through the dispense fluid path. In some embodiments, the dispense fluid path may comprise the needle 46 and the catheter 48. In some embodiments, the dispense fluid path 57 is fluidly connected to the reservoir 34. In some embodiments, the dispense fluid path may include a channel in the pump enclosure, a tubing, or both to fluidly connect the reservoir 34 to the needle and catheter. The dispense fluid path may be a part of the fluid path that enables the medicament to be added to the IDD and then to be dispensed from the IDD. In some embodiments, such fluid path can include one or more of the following components: the fill port 4, the inlet port 33 of the reservoir 34, the reservoir 34, the outlet port 35 of the reservoir 34, the needle 46, the catheter 48, and optionally a connector to connect the reservoir 34 to the needle 46 and the catheter 48 (such as the bottom enclosure channel 58, the tubing 60, or both). In some embodiments, the fluid path may include additional connection devices between the one or more components of the fluid path to form a continuous path for the medicament.

The pump sub-subsystem includes, but is not limited to, a motor/gearbox 15, geartrain assembly 36, screw train assembly 42, a pusher 44 to deliver the medicament (e.g., insulin/drug) to a patient, a primary index high resolution encoder, and a backup low resolution encoder.

As shown, the electrical sub-subsystem includes, but is not limited to, the PCBA 40 that houses and electrically interfaces many of the components of the IDD 10 including, but not limited to, integrated circuits (ICs), a motor driver 55, a battery 38, a current sensor 53, a pressure sensor 50, microcontrollers 52 (MCUs) with processor, memory and input/output peripherals, network adapter, index encoder sensor and backup encoder sensor. Some of the functions of the electrical sub-subsystem in conjunction with the firmware of the IDD 10 include, but are not limited to, turning the IDD 10 on/off; recognizing user input; processing data; storing data; managing power supply; sending and receiving data; priming; detecting reservoir volume; detecting occlusion; delivering insulin; and pairing/unpairing to an external device/application via Bluetooth®.

In some embodiments, there are two microcontrollers 52 in the IDD. In some embodiments, one additional MCU of the IDD 10 is an independent safety microcontroller ("Safety MCU") that monitors the current sensor, the index encoder, and backup encoder while communicating to the BLE MCU to ensure proper pump operation. The Safety MCU and BLE MCU each have the ability to shut down the motor/gearbox 15 in the event of a fault condition. A motor driver 55 is used to turn the motor/gearbox 15 forward. In some embodiments, the motor/gearbox 15 is a DC motor. In some embodiments, the DC motor is a DC brushed motor. The motor current is monitored on the high side of the motor with a sense resistor. This sense resistor is used to measure motor current to determine pump performance and infer battery health. In some embodiments, the current sensor 53 is also used to detect motor runaway. In some embodiments, the current sensor 53 is used for occlusion detection.

Figure 7:
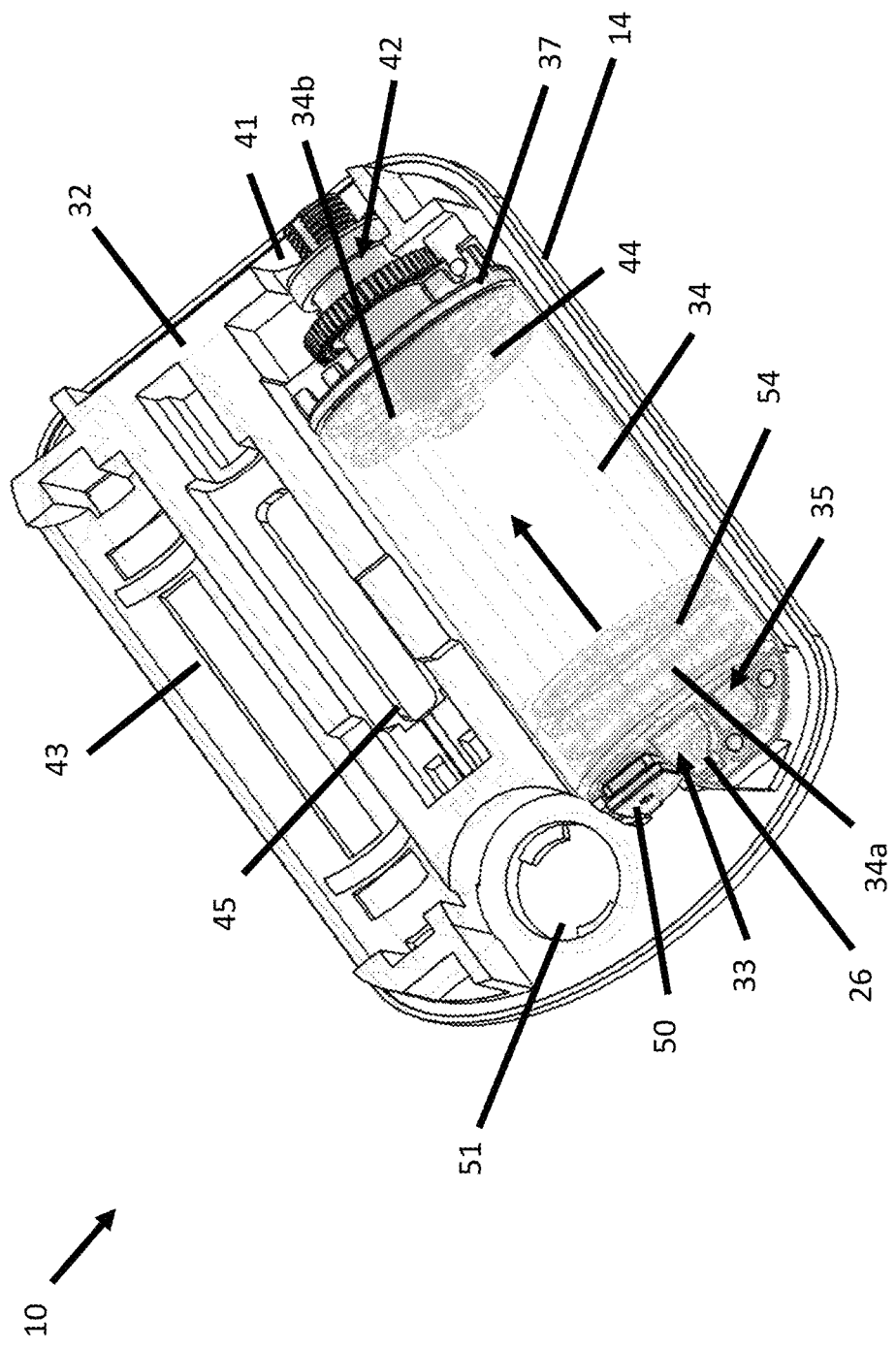
FIG. 7 is a perspective view of some of the inner components of an exemplary IDD of the present disclosure with its top enclosure removed for clarity.
Figure 8:
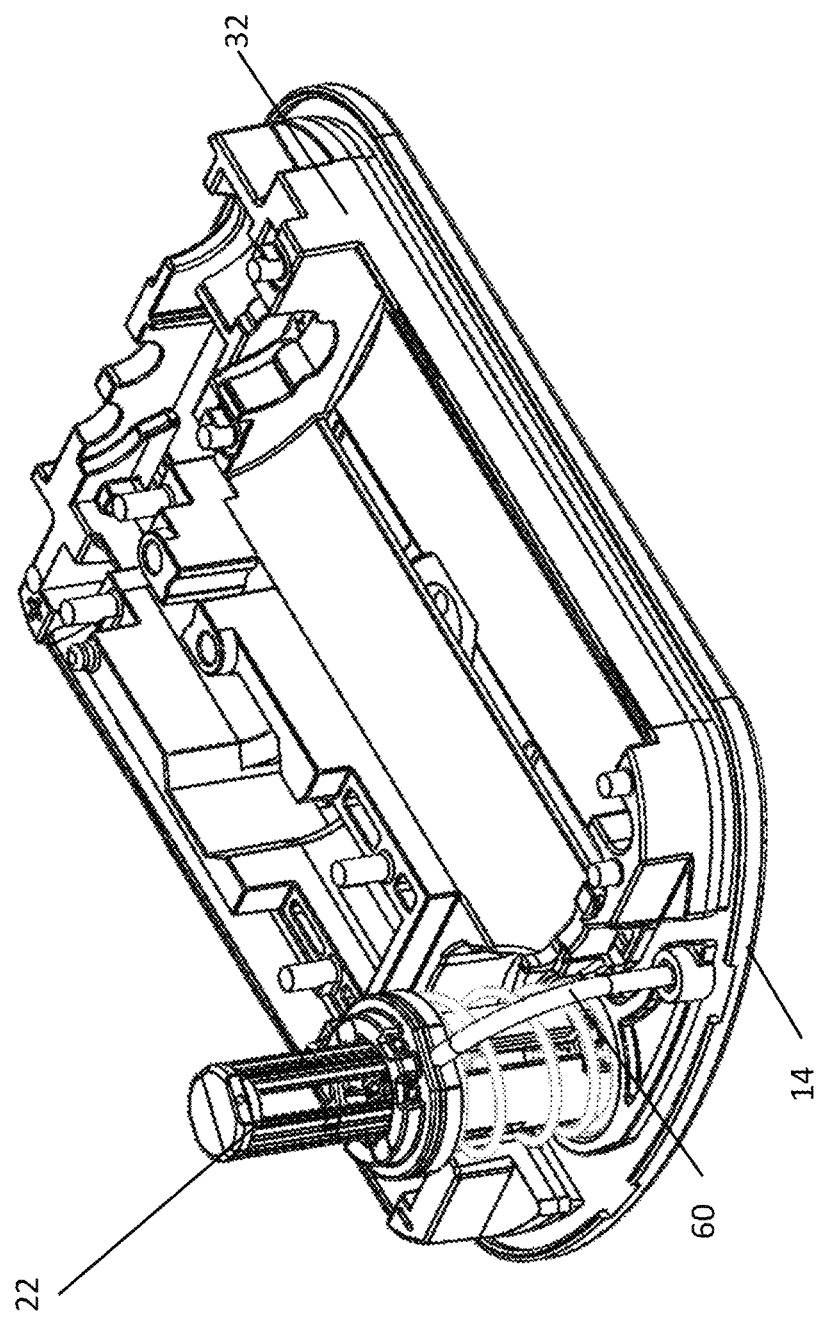
FIG. 8 is a perspective view of an exemplary IDD of the present disclosure showing an insertion mechanism and associated tubing for delivering a drug to a user.

FIG. 7 provides an exemplary perspective view illustrating a mechanical interface between the internal bracket superstructure 32 and reservoir 34 of the IDD 10. The reservoir 34 comprises a closed end 34a of reservoir 34, and a capped end 34b of reservoir 34. A medicament exits the reservoir 34 to flow to the user through outlet port 35 at closed end 34a, and the capped end 34b engages with a reservoir cap 37 to engage with a screw train assembly 42. The internal bracket superstructure 32 may comprise a compartment shaped to fit reservoir 34, and the reservoir 34 may be inserted into the compartment of internal bracket superstructure 32.

In some embodiments, the pressure sensor 50 is disposed within the reservoir 34 or the fluid path. In some embodiments, the pressure sensor 50 may be disposed at the closed end 34a of reservoir 34, such that the pressure sensor 50 is configured to measure a pressure in the reservoir 34. The closed end 34a of the reservoir 34 contains the inlet port 33 and the outlet port 35 and also engages the pressure sensor 50. The inlet port 33 is in fluid communication with the fill port 4 in the bottom enclosure 14. The bottom enclosure 14 comprises an outlet port 19 (visible in FIGS. 2 and 5) that is sealed via a gasket seal 8 (visible in FIGS. 9 and 10B) that is compressed between the outlet port 35 of the reservoir 34 and bottom enclosure 14. Compressive force is achieved through the use of multiple thermal joints which fasten the reservoir 34 to the internal bracket superstructure 32 and the internal bracket superstructure 32 to the bottom enclosure 14. The internal bracket superstructure 32 may comprise space 43 for the battery, space 45 for the motor/gearbox 15, space 51 for the insertion mechanism, and space 41 for components of the screw train assembly. At the capped end 34b of the reservoir 34, a reservoir cap 37 is configured to be coupled to a sleeve screw of the screw train assembly 42 of the pump sub-subsystem and the reservoir 34 within the fluid sub-subsystem acting as a connection between the two sub-subsystems. It has features that constrain axial and rotational movement of the reservoir 34 through heat stakes and surface features to the internal bracket superstructure 32.

Figure 9:
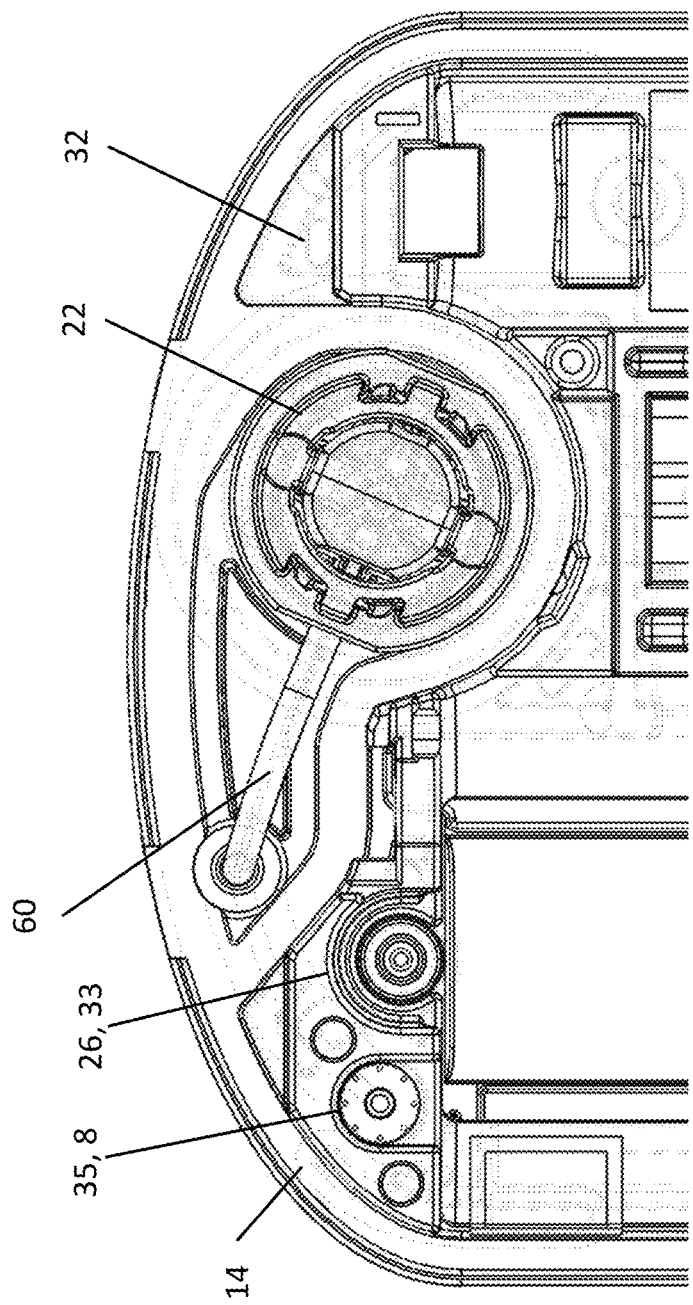
FIG. 9 is a close-up top view of a portion of an exemplary IDD of the present disclosure showing some of the components of a fluid path.
Figure 10A:
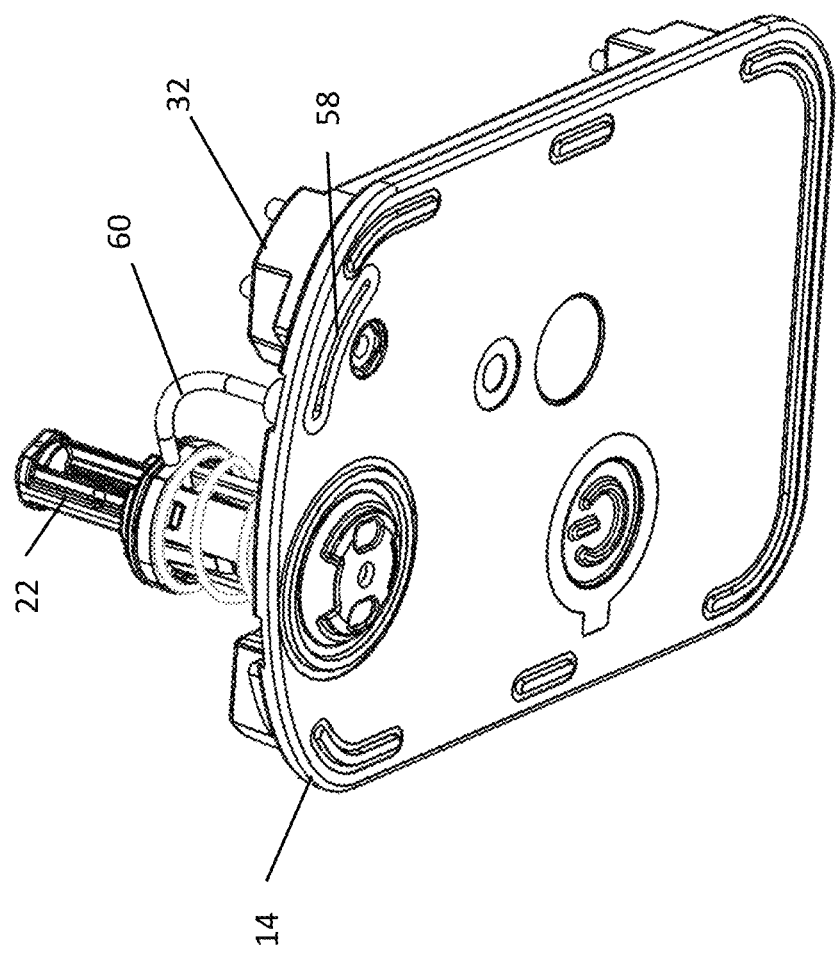
FIG. 10A is a bottom perspective view of an exemplary IDD of the present disclosure showing some components of a fluid path, including an insertion mechanism and associated tubing for delivering a drug to a user.
Figure 10B:
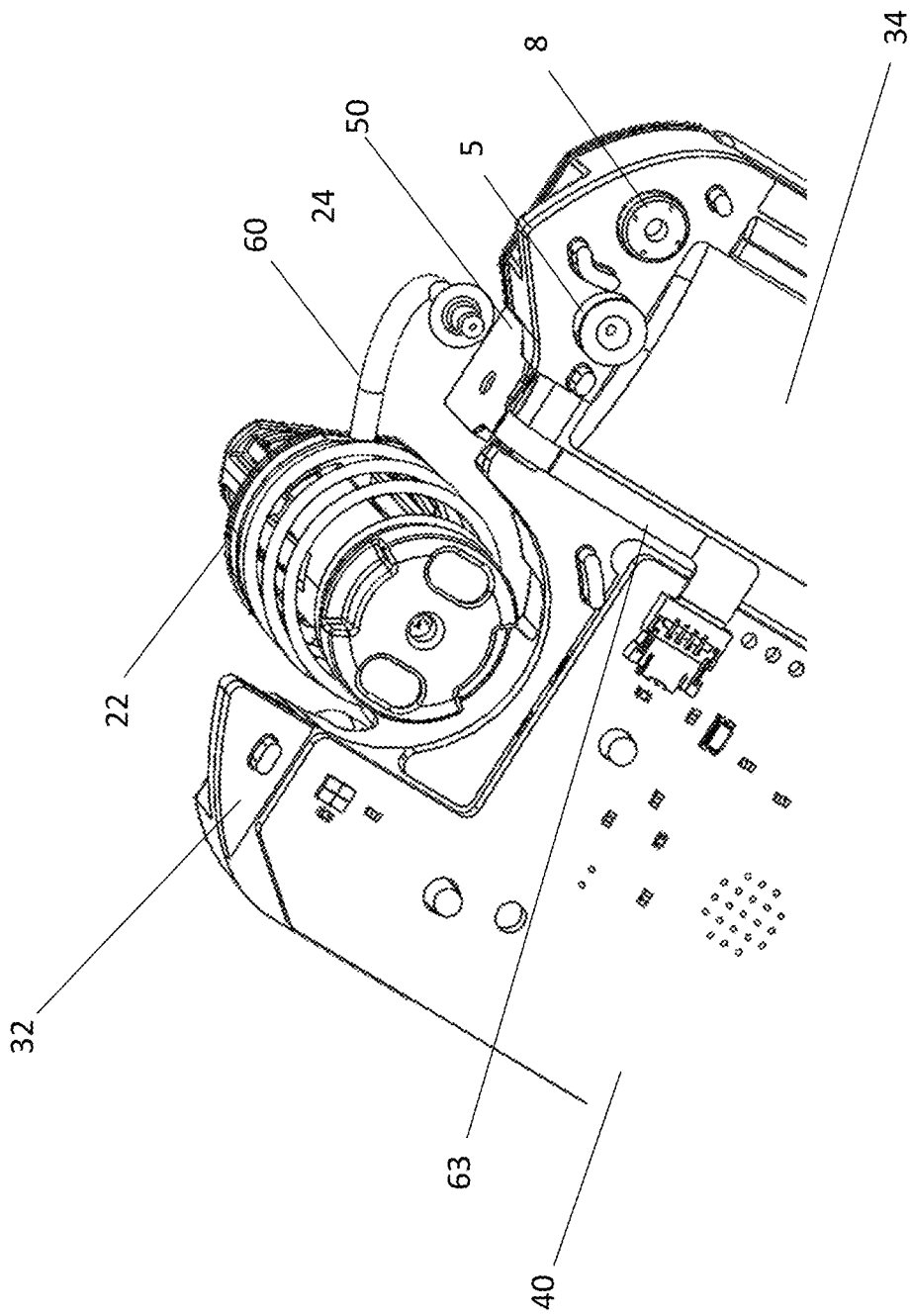
FIG. 10B is a bottom perspective view of an exemplary IDD of the present disclosure with some components removed for clarity.

FIGS. 8, 9, 10A, and 10B provide additional views of the IDD 10, illustrating the fluid flow path from the reservoir to the insertion mechanism 22 of the insertion mechanism sub-system using the tubing 60. FIG. 9 provides a top view of the IDD 10 to illustrate the tubing 60 and its connection to the bottom enclosure 14 to connect to the reservoir 34, while FIGS. 10A and 10B provide bottom perspective views to further illustrate an embodiment of the dispense fluid path between the insertion mechanism 22 and reservoir 34 comprising bottom enclosure channel 58 and tubing 60. "Proximal," as used herein in relation to one or more components or points of the fluid path, refers to the direction towards, or being nearer to, a capped end of the reservoir of the IDD 10 (e.g., an end of the reservoir that does not include an outlet port for distributing fluid out of the reservoir). "Distal," as used herein in relation to one or more components of or points along the fluid path, refers to the direction towards, or being nearer to, the point at which fluid is expelled from the fluid path of the IDD 10.

As shown in FIGS. 11A-11E, which show all or only a portion of components of the insertion mechanism 22 in some embodiments, the insertion mechanism 22 is configured to allow the fluid to flow from the outlet port 35 of the reservoir, through the bottom enclosure channel 58, through the tubing 60, through the needle 46, and through the catheter 48 into the patient. The insertion mechanism 22 includes a catheter hub assembly (which includes a catheter hub 79, the catheter 48, a wedge 78, and a septum 77—shown in FIG. 11B), a hub assembly (which includes the catheter hub assembly, a needle hub 75, and the needle 46 with a proximal end 92 of the needle 46—shown in FIG. 11E), a button assembly (which includes a button 71, the hub assembly, a cap 72, and a clip 74), a return spring 73, a housing 70, and the tubing 60. When a user wearing the IDD 10 presses the button 71 of the insertion mechanism 22, the return spring 73 is compressed and the needle 46 and the catheter 48 are both extended from a bottom surface of the insertion mechanism 22 and therefore from a bottom surface of the IDD 10. The insertion mechanism 22 is configured to then retract the needle 46 via release of the return spring 73, leaving the catheter 48 extended. The fluid from the reservoir 34 can then be delivered to the user.

In some embodiments described herein, the fluid path can have a first available volume prior to deployment of one or more components of the fluid path, such as the catheter or needle, to deliver fluid, from the housing of the IDD 10, and the fluid path can have a second available volume after deployment of one or more components of the fluid path. The second available volume can be greater than the first available volume. The "available volume," as used herein, can generally refer to the volume of the fluid path in a particular configuration (pre-deployment or post-deployment) that is available for receiving a liquid, such as a medicament. That is, the available volume refers to the volume of the fluid path, from the proximal end of the fluid path to the distal end of the fluid path, that can contain a volume of liquid in a particular configuration of the fluid path. As an example, the available volume of the fluid path can generally be thought of as the sum of the individual volumes of each component of the fluid path minus any overlap in the individual volumes of the components of the fluid path. An overlap in the individual volumes of the components of the fluid path can result from a first component of the fluid path being positioned within a second component of the fluid path such that liquid flows through the first component without flowing through, or be contained by the walls of, the second component. In such a case, the volume of the second component is not an available volume of the fluid path because it cannot fill with or contain liquid.

Figure 11A:
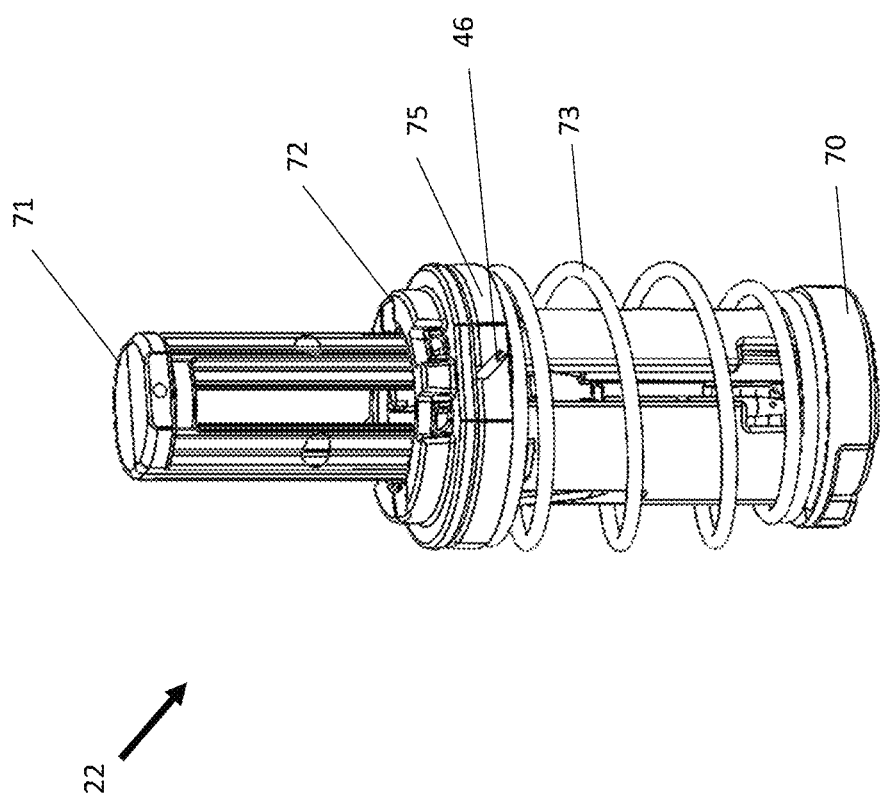
FIG. 11A is a perspective view of the insertion mechanism of an exemplary IDD of the present disclosure in a pre-activated configuration.

Referring now specifically to FIGS. 11A and 11B, the insertion mechanism 22 is depicted in a first, non-activated, state or configuration. FIG. 11B shows a fluid path 900, in particular a dispense fluid path, comprising the catheter 48 and the needle 46 disposed within the catheter 48. When the insertion mechanism 22 is in the non-activated configuration, the fluid path 900 is in the pre-deployed configuration (that is, no components of the fluid path 900 are deployed from the housing of the IDD 10). Therefore, FIGS. 11A and 11B also depict the fluid path 900 in the pre-deployed configuration. In the pre-deployed configuration, the fluid path 900 can have a first property value (e.g., a first pressure in the fluid path 900). FIG. 11A shows a perspective view of the insertion mechanism 22 in the non-activated configuration, and FIG. 11B shows the needle 46 and catheter 48 isolated from some of the portions of the insertion mechanism 22 with the insertion mechanism 22 in the non-activated configuration. In some embodiments, when the insertion mechanism 22 is in the non-activated configuration (or the fluid path 900 is in the pre-deployed configuration), the needle 46 is positioned within the catheter 48 in its entirety. In some embodiments, a portion of the needle 46 is positioned within the catheter. In some embodiments, the needle tip may extend beyond the catheter. In some embodiments, the needle 46 is positioned within the catheter 48 and extends the entire length, or substantially the entire length, of the catheter 48. Therefore, in the pre-deployed state, the available volume of the fluid path 900 does not include the entire volume, or substantially the entire volume, of the catheter 48. This is because, in the embodiment shown in FIG. 11B, for instance, fluid in the fluid path 900 can travel into the proximal end 92 of the needle 46 via the tubing 60, through the length of the needle 46, and to or out a distal end 90 of the needle 46 without ever entering the catheter 48 (e.g. without ever being contained in the fluid path 900 by the walls of the catheter 48). Therefore, in some embodiments, the volume of the catheter 48 is not available to receive fluid when the fluid path 900 is in the pre-deployed configuration. In some embodiments, when the fluid path 900 is in the pre-deployed configuration, the available volume of the fluid path 900 can include some or all of the volume of the reservoir 34 (FIG. 7), some or all of the volume of the bottom enclosure channel 58 (FIG. 10A), some or all of the volume of the tubing 60 (FIG. 10A), and some or all of the volume of the needle 46.

Figure 11C:
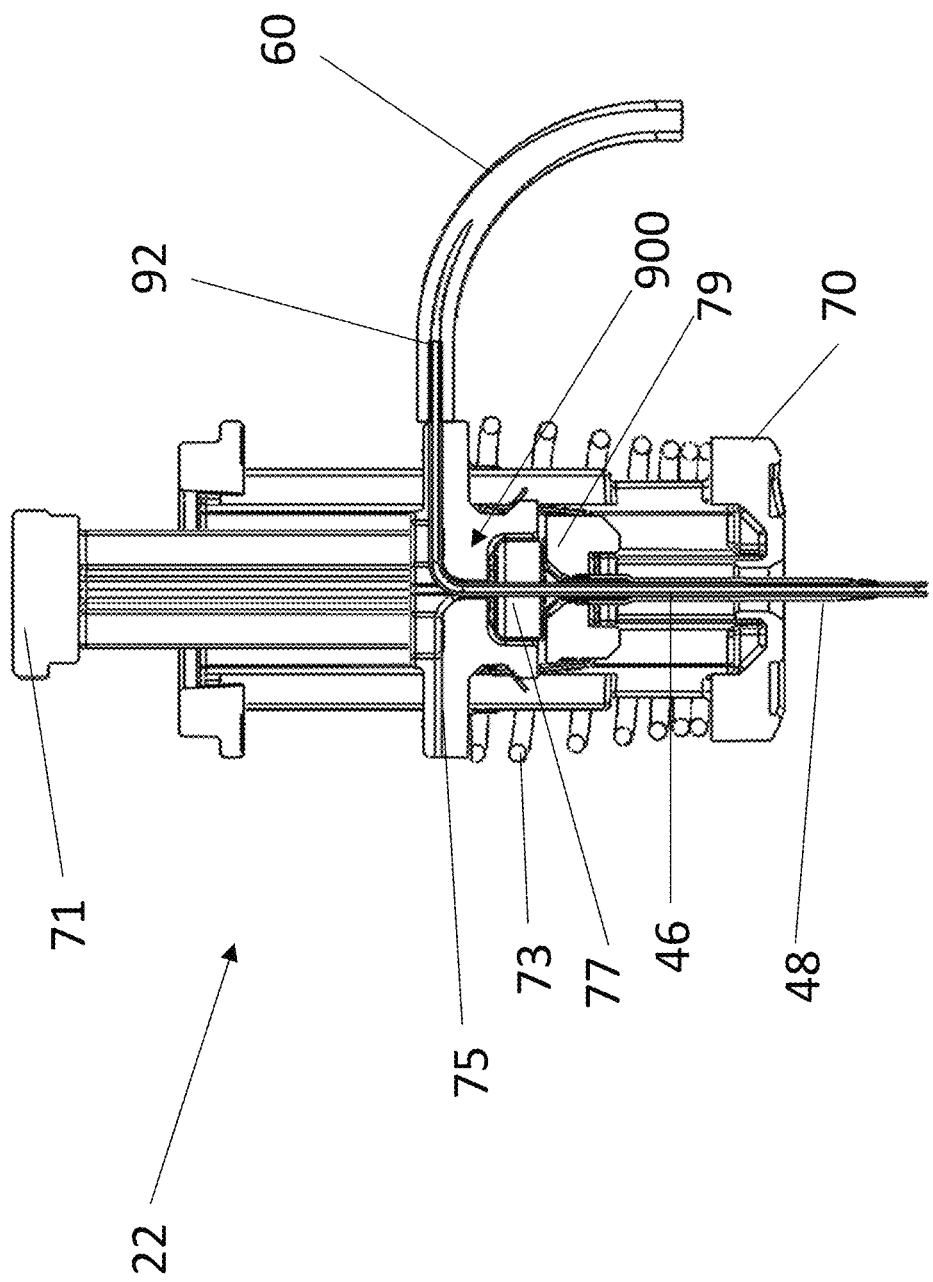
FIG. 11C is a cross-sectional view of the insertion mechanism of an exemplary IDD of the present disclosure during activation.

Referring now specifically to FIG. 11C, the insertion mechanism 22 is shown during activation, and the fluid path 900 is shown during deployment. When a user wearing the IDD 10 presses the button 71 of the insertion mechanism 22, the return spring 73 is compressed and the needle 46 and the catheter 48 both begin to extend from a bottom surface of the insertion mechanism 22 and therefore from a bottom surface of the IDD 10. In some embodiments, during deployment of the fluid path 900, the property of the fluid path 900 (e.g., the pressure in the fluid path 900) can remain unchanged from the first property in the pre-deployed configuration. In some embodiments, the available volume of the fluid path 900 during deployment can remain unchanged from the available volume of the fluid path 900 when the fluid path 900 is in the pre-deployed configuration. During deployment, the needle 46 and the catheter 48 can move together to extend from the bottom surface of the insertion mechanism 22. For instance, in some embodiments, when being deployed, the needle 46 and the catheter 48 do not move relative to each other. In some embodiments, during deployment, the needle 46 and the tubing 60 do not move relative to each other. Particularly, the tubing 60 can be flexible such that the tubing moves downward with the needle 46 during deployment. In some embodiments, the available volume of the fluid path 900 during deployment of the fluid path 900 can remain unchanged from the available volume of the fluid path 900 when the fluid path 900 is in the pre-deployed configuration due to an absence of relative movement between one or more components of the fluid path 900.

Figure 11D:
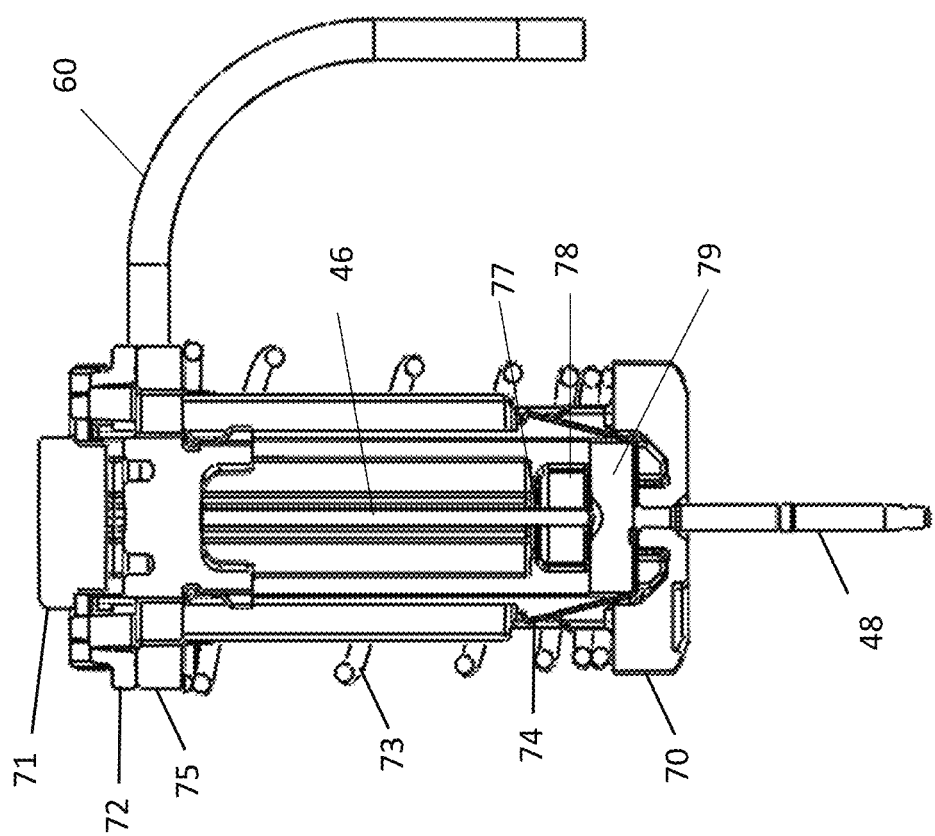
FIG. 11D is a partial cross-sectional view of the insertion mechanism of an exemplary IDD of the present disclosure in an activated configuration.
Figure 11E:
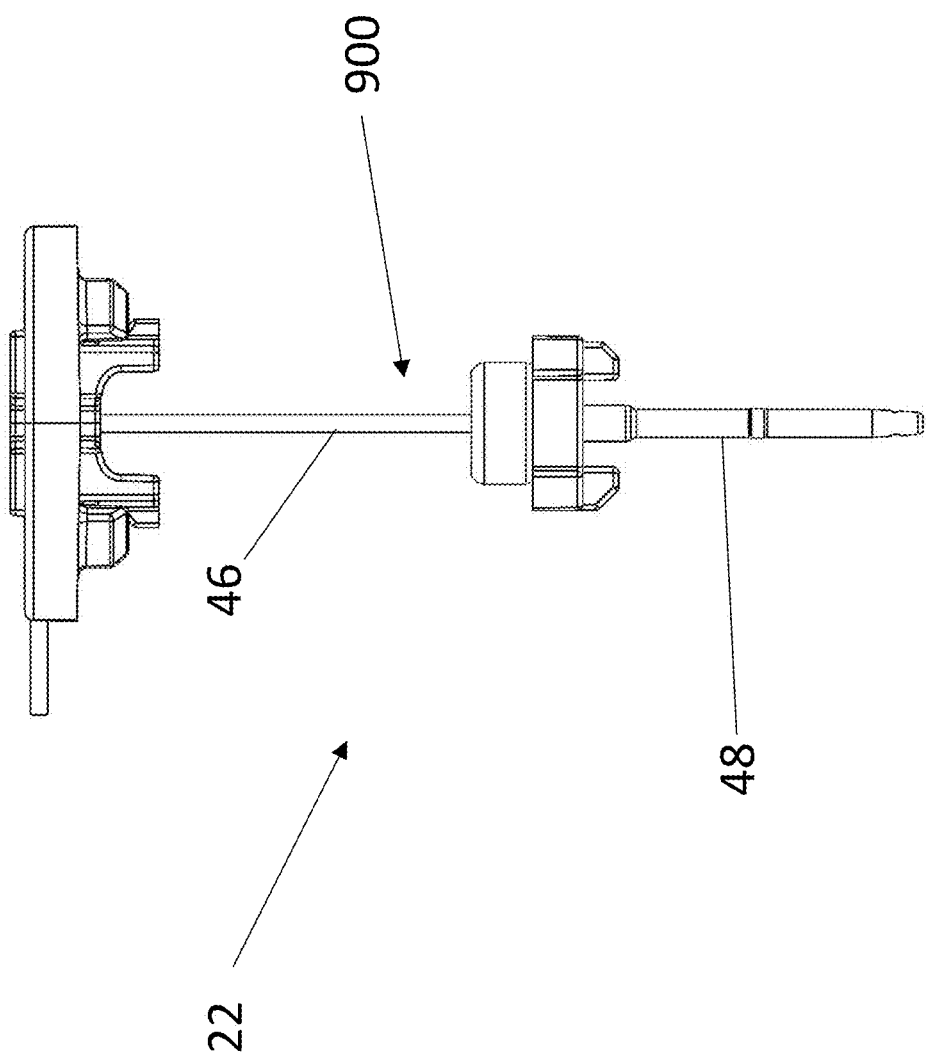
FIG. 11E is an isolated side view of fluid path components of the insertion mechanism of an exemplary IDD of the present disclosure in the deployed configuration.

Referring now specifically to FIGS. 11D and 11E, the insertion mechanism 22 is shown in the fully activated configuration. When the insertion mechanism 22 is in the fully activated configuration, the fluid path 900 can be in a deployed configuration. Therefore, FIGS. 11D and 11E, also, display the fluid path 900 in the deployed configuration. FIG. 11D illustrates a partial cross-sectional view of the insertion mechanism 22 in the activated configuration, and FIG. 11E illustrates the needle 46 and catheter 48 isolated from the some of the portions of the insertion mechanism 22 with the insertion mechanism 22 in the activated configuration. In the deployed configuration, or in some embodiments immediately after entering the deployed configuration, the fluid path 900 can have a second property value different from the first property value (e.g., a second pressure in the fluid path 900). After the button 71 is fully depressed, the insertion mechanism 22 is configured to then retract the needle 46 via release of the return spring 73, leaving the catheter 48 extended, as shown. The needle and the catheter remain in fluid communication. In some embodiments, the needle may connect to the catheter directly. In some embodiments, the needle may connect to the catheter indirectly such as using another conduit in fluid communication with both the catheter and the needle. The catheter 48 can be left extended or deployed from a bottom surface of the housing of the IDD 10. In some embodiments, the available volume of the fluid path 900 when the fluid path 900 is in the deployed configuration can be different than the available volume of the fluid path 900 when the fluid path 900 is in the pre-deployed configuration. In some embodiments, the available volume of the fluid path 900 when the fluid path 900 is in the deployed configuration can be greater than the available volume of the fluid path 900 when the fluid path 900 is in the pre-deployed configuration.

In some embodiments, some or all of the volume of the catheter 48 can be available volume of the fluid path 900 in the deployed configuration, where the same volume of the catheter 48 was not part of the available volume of the fluid path 900 in the pre-deployed configuration. In some embodiments, the movement of the needle 46 in the proximal direction relative to the catheter 48 can add some or all of the volume of the catheter 48 as available volume of the fluid path 900 in the deployed configuration. For instance, in the deployed configuration, liquid can enter the proximal end 92 (FIG. 11C) of the needle 46, travel the length of the needle 46, exit the distal end 90 (FIG. 11B) of the needle 46, enter the catheter 48 at the proximal end, or near the proximal end, of the catheter 48, and travel to the distal end of the catheter 48. Therefore, all or substantially all of the volume of the catheter 48 can contain fluid when the fluid path 900 in the deployed configuration. In some embodiments, when the fluid path 900 is in the deployed configuration, the available volume of the fluid path 900 can include some or all of the volume of the reservoir 34 (FIG. 7), some or all of the volume of the bottom enclosure channel 58 (FIG. 10A), some or all of the volume of the tubing 60 (FIG. 10A), some or all of the volume of the needle 46, and some or all of the volume of the catheter 48.

While in the example embodiment discussed above, the increased available volume of the fluid path 900 is the result of the needle 46 moving relative to the catheter 48, this should be appreciated as a non-limiting example. For instance, in some embodiments, during or after deployment of the fluid path 900, the needle 46 can move distally, such that the proximal end 92 of the needle 46 moves distally in the tubing 60. Therefore, in the pre-deployed configuration, fluid can travel through a first volume of the tubing 60 and then enter the proximal end 92 of the needle 46, and in the deployed configuration, fluid can travel through a second volume of the tubing 60 (equal to the first volume plus the volume of the tubing 60 vacated by the needle 46 due to the distal movement of the needle 46) and enter the proximal end 92 of the needle 46. It should be appreciated that in some embodiments, multiple components of the fluid path 900 can move relative to each other during or after deployment of the insertion mechanism 22, resulting in a different, and in some cases increased, available volume of the fluid path 900 in the deployed configuration compared to the pre-deployed configuration. In some embodiments, the available volume of the fluid path 900 can change, and in some cases increase, at one or more points along the fluid path 900. For instance, in some embodiments, the available volume of the fluid path 900 can increase in the deployed configuration relative to the pre-deployed configuration by distal movement of the needle 46 relative to the tubing 60 and by proximal movement of the needle 46 relative to the catheter 48.

Figure 12:
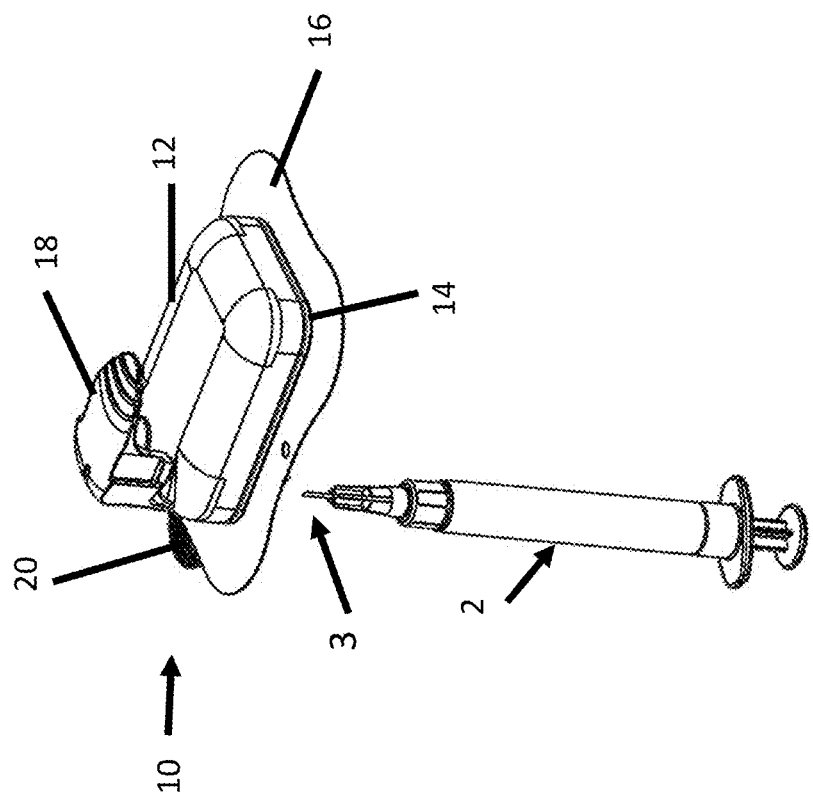
FIG. 12 shows an exemplary IDD of the present disclosure and a syringe with a needle preparing for a fill event.
Figure 13:
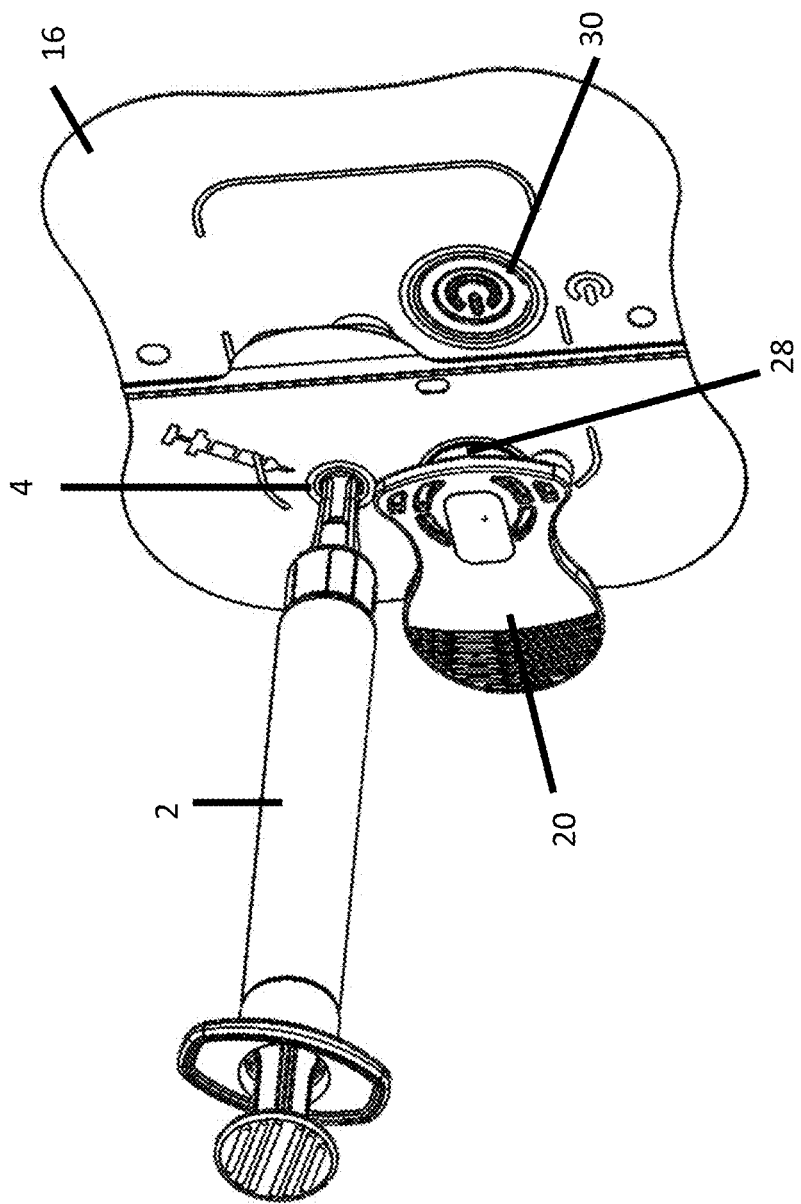
FIG. 13 is a perspective bottom view of an exemplary IDD of the present disclosure and syringe with needle of FIG. 12 during a filling step.

FIGS. 12-13 provide perspective views of the IDD 10 in preparation for and during a filling event. In some embodiments, a user may insert a needle of a filled syringe 2 into the fill port 4 through the fill port 4, and fill the internal reservoir 34 with an amount of a medicament as desired.

Figure 14:
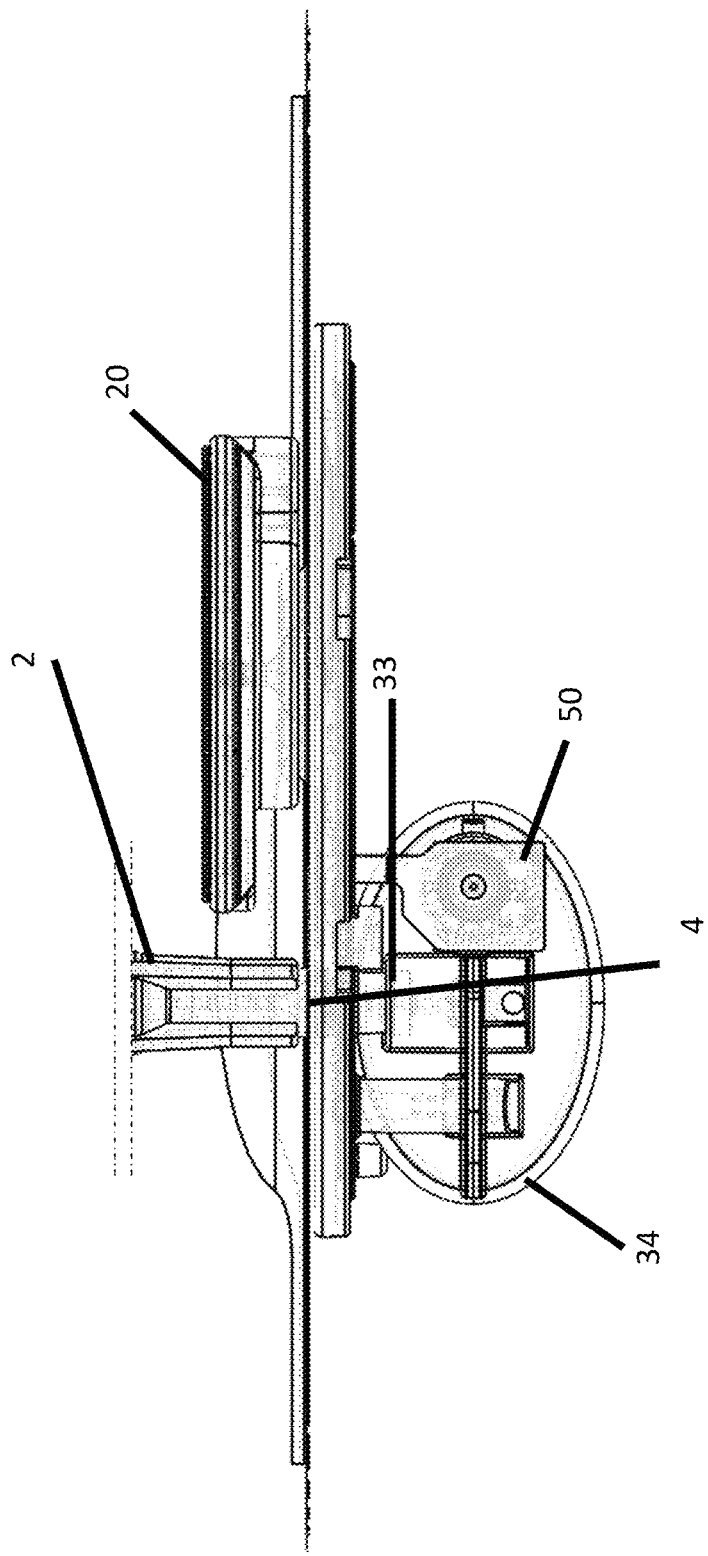
FIG. 14 is a side view of a portion of an exemplary IDD of the present disclosure and syringe with needle of FIG. 13 during a filling step.

FIG. 14 shows a side end view of the IDD 10 and the syringe 2 and the needle 3 during a filling event. In some embodiments, during the filling event, the insertion seal assembly 20 is still attached to the IDD 10 and the fluid path is selectively blocked when the fill of the medicament fluid is completed. As illustrated in FIG. 14 in conjunction with FIGS. 12-13, a user fills the IDD 10 via the fill port 4. As the medicament flows into the inlet port 33 of the reservoir 34, the floating plunger 54 is forced back within the reservoir 34, moving from a first position to a second position (as indicated by the direction of the arrow in FIG. 7) as the reservoir 34 fills with the medicament. In some embodiments, the plunger 54 is an assembly consisting of a rigid part with two o-rings 56 to provide fluid sealing. One o-ring 56 is located near the front and one is located near the rear of the plunger 54. The dual o-ring design also provides a length/diameter (LD) ratio to prevent jamming or loss of sealing if the piston were to tilt off axis during axial motion. The plunger 54 is intended to be floating, not rigidly coupled to other parts to allow variable doses to be filled into the IDD 10. After filling the medicament, the fluid paths may be blocked such that any medicament is not allowed to flow in the IDD 10.

II. Systems and Methods for Operating Embodiments of Infusion Delivery Devices and Management Systems Provided herein are methods and systems for operating an IDD, according to presently disclosed embodiments. Embodiments disclosed herein are directed to methods and systems for performing one or more of: (A) fill event detection; (B) fill volume detection; (C) mechanical compliance calibration/air detection of an infusion management system after fill event and priming; (D) occlusion detection after removal of insertion seal assembly; (E) detecting fluid path deployment of an infusion delivery device; (F) monitoring for occlusion detection during pump use; and (G) detecting an empty reservoir.

Figure 15:
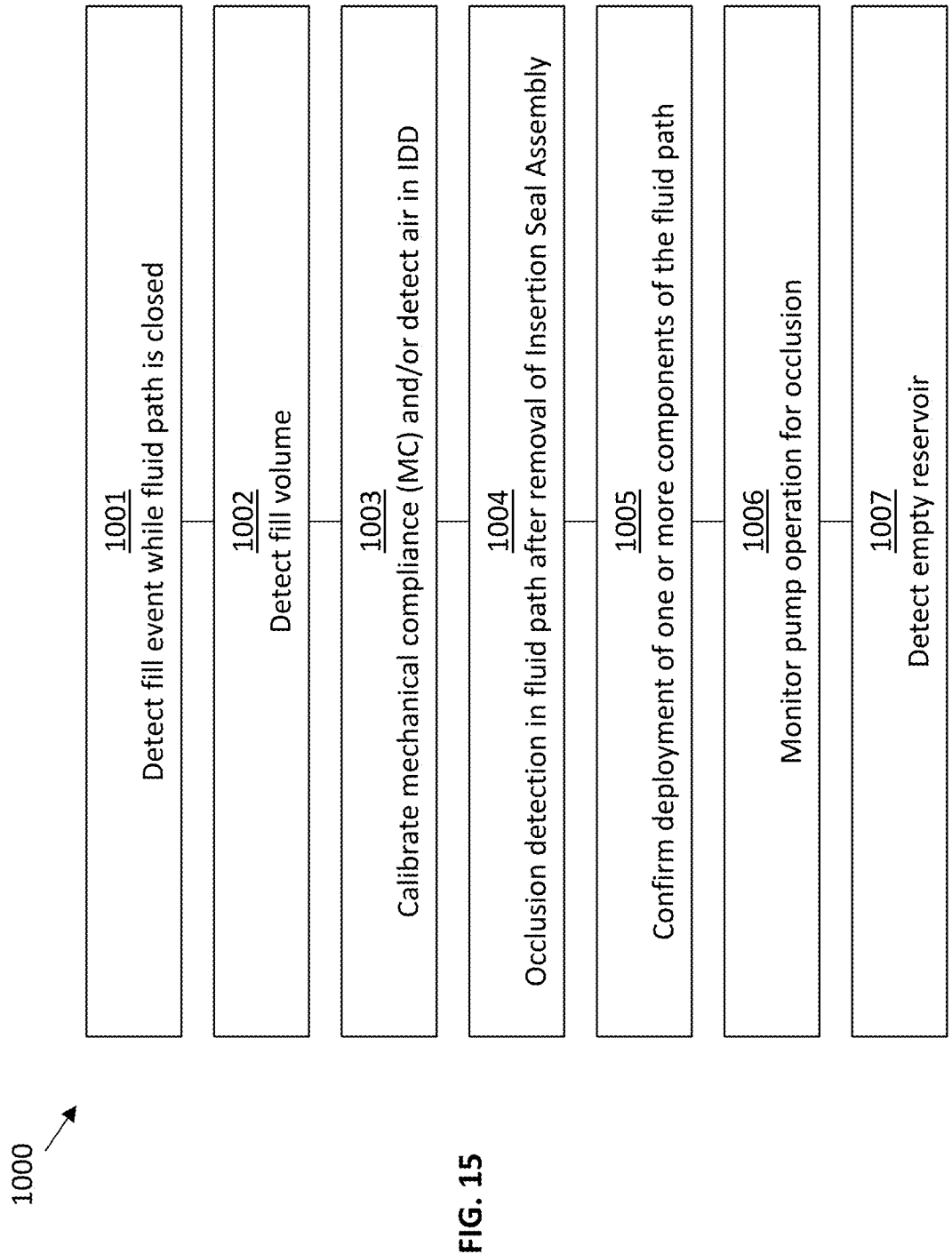
FIG. 15 is a block diagram of exemplary processes using an exemplary IDD of the present disclosure.

In reference to FIG. 15, the present disclosure provides systems and methods to perform one or more steps of an exemplary block diagram 1000 for operating an IDD. Step 1001 comprises detection of a fill event of an IDD. Step 1002 comprises detection of a fill volume of a reservoir of an IDD. Step 1003 comprises calibration of a mechanical compliance of an IDD and/or detection of the presence of air (e.g., an air bubble) within the fluid path of the IDD. Step 1004 comprises removing the insertion seal assembly and detecting an occlusion in the fluid path. Step 1005 comprises detecting a deployment of the fluid path that provide a passage for fluid to flow from the IDD to the patient. Step 1006 comprises detecting an occlusion during operation of the IDD. Step 1007 comprises detecting when the reservoir of the IDD is empty.

It should be noted that the order of the one or more steps in FIG. 15 is shown for illustrative purposes only. It should further be understood that various combinations of one or more of steps 1001-1007 may be employed in operating an IDD of the present disclosure, and the various combinations of the one or more steps 1001-1007 can be performed in parallel or sequentially. In some embodiments, the IDD is programmed to perform one of the one or more steps 1001-1007. In some embodiments, the IDD is programmed to performed multiple of the one or more steps 1001-1007.

A. Fill Event Detection

In reference to step 1001 of FIG. 15, the present disclosure provides systems and methods for detecting a fill event of the IDD 10.

To maintain medicament efficacy and patient safety, it is desirable to understand the conditions of the medicament, e.g., insulin, within the reservoir. In general, reservoirs are biocompatible and stable for insulin, but, based on the type of pump used (for example, disposable vs. long-term), the reservoir may only be designed for limited durations of medicament exposure. Mechanisms that can provide information about when medicament was added to a reservoir of a pump would be beneficial for determining that the reservoir was filled with medicament at the appropriate time, such that medicament stability within the infusion pump reservoir can be assessed so as to avoid potential medicament degradation and loss of activity prior to initiating delivery. In some embodiments, mechanisms that can provide information about when medicament was added to a reservoir of a pump would further be beneficial for determining how long the medicament has been sitting in the reservoir prior to insertion of the pump for use.

Figure 16:
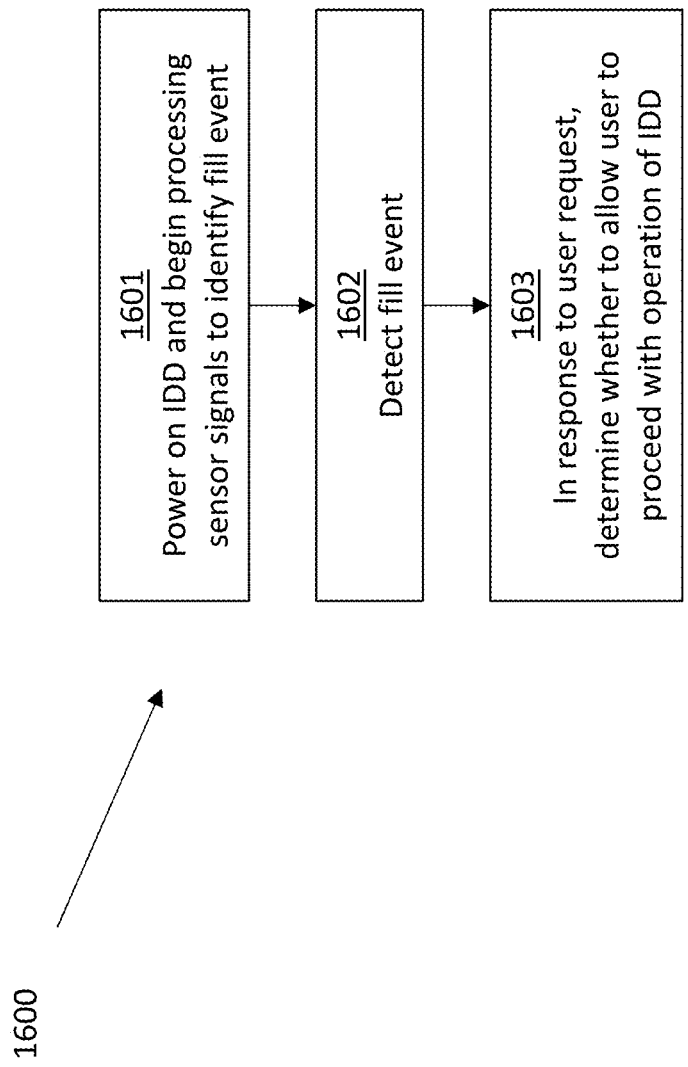
FIG. 16 is a flow chart of an exemplary process for detecting a fill event in an exemplary IDD of the present disclosure.

FIG. 16 illustrates a flow chart of an exemplary process 1600 for detecting a fill event after initializing an IDD 10. Step 1601 of process 1600 begins with initializing the IDD and processing sensor signals to measure and/or identify a fill event. In some embodiments, the pressure sensor 50 starts monitoring the pressure after pairing the IDD with a WC. In some embodiments, step 1601 comprises instructing the user to fill the reservoir with a medicament (e.g., insulin). Step 1602 comprises monitoring the IDD 10 to detect a fill event. Step 1603 comprises, in response to a request or confirmation from a user, determining whether to allow the user to proceed with operation of the IDD 10.

Figure 17:
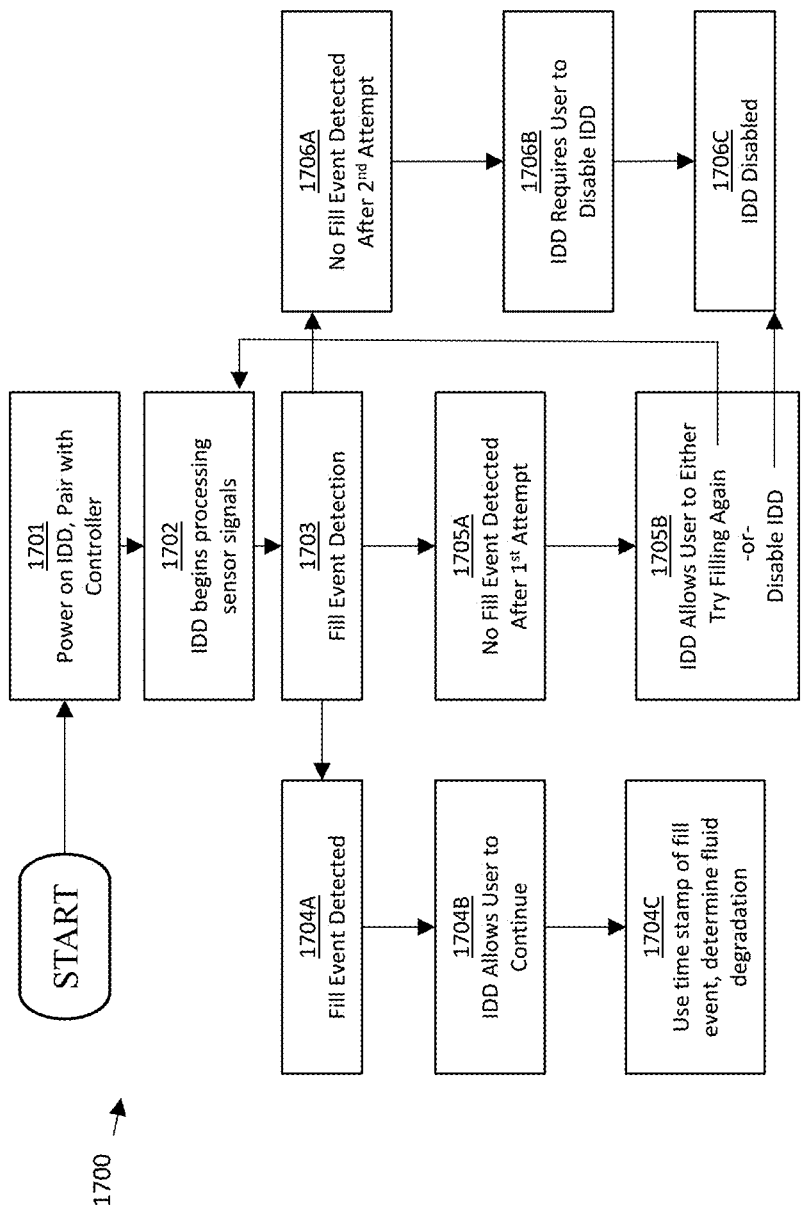
FIG. 17 is a flow chart of an exemplary process for detecting a fill event in an exemplary IDD of the present disclosure.

FIG. 17 illustrates a flow chart of an exemplary process 1700 of an IDD 10 performing a fill event detection process, according to embodiments of this disclosure. Step 1701 comprises powering on the IDD 10 and pairing with the WC. In step 1702, once pairing has been confirmed, the IDD 10 begins processing pressure measurements so as to identify a fill event. In some embodiments, the user is instructed to fill a reservoir 34 in the IDD 10 with a medicament (e.g., insulin). In some embodiments, the as the user fills the reservoir 34, a plunger 54 in the reservoir 34 may be forced through the reservoir 34. In some embodiments, the plunger 54 comprises a detached, floating plunger 54. In some embodiments, there may be friction between the plunger 54 and the reservoir 34 such that the friction may provide a frictional force that must be overcome for the plunger 54 to progress through the reservoir 34. This may require that the movement of the plunger 54 produce a minimum magnitude of force. Over a cross-sectional area of the plunger 54, this minimum magnitude of force may be equivalent to a fluidic pressure. As the reservoir 34 is being filled and the reservoir plunger 54 is in motion, a fluidic pressure is generated in the reservoir 34. In some embodiments, the at least one pressure sensor 50 is within the reservoir 34 or fluid path so as to measure this amount of fluidic pressure in the reservoir 34 or the fluid path. In some embodiments, the at least one pressure sensor 50 comprises an input that interfaces with a closed end of the reservoir 34. In some embodiments, the IDD 10 does not include, i.e., is devoid of, a flow sensor and includes at least one pressure sensor configured to measure fluidic pressure.

Using the at least one pressure sensor 50, fluidic pressure may be discretely or continuously monitored and used to detect a filling event, indicated in step 1703. The filling event detection in step 1703 is implemented to prevent users from using an IDD 10 that was previously filled with insulin prior to when they actually intended to use the IDD for immediate infusion delivery. An IDD 10 may be designed for a particular infusion time frame. In some embodiments, the infusion time frame may be up to 80 hours. In some embodiments, the system is configured to transmit notifications to a user during use to alert them of how much time the IDD 10 has been in use or has remaining to be in use. In some embodiments, the alert may be based on a predefined error code. In some embodiments, the time frame may be variable based on a type of medicament with which the reservoir is filled. In some embodiments, the time frame may be variable based on a use case of the IDD 10 and/or the medicament. In some embodiments, the system is configured to notify a user between 48-71 hours after initiating operation of the IDD 10. In some embodiments, the system is configured to notify a user at 72 hours after initiating operation of the IDD 10 to indicate an end of life of the IDD 10 is approaching. In some embodiments, the system is configured to notify a user at 79 hours after initiating operation of the IDD 10 to indicate the device will shut down in 1 hour. In some embodiments, the system is configured to notify a user at 80 hours that the device is shutting down now. If a user has pre-filled the IDD 10 prior to when they actually were prepared to use the IDD for insulin delivery, the insulin may be kept in the IDD for too long of a useful effective time that the insulin may degrade. Thus, if the IDD 10 is then turned on to initiate infusion, the user may be in danger of infusing dangerous or ineffective insulin. Step 1703 is required for the system to keep track of when the IDD 10 was initially filled with insulin. Thus, guidance from the system via fill event detection helps monitor for pressure signals at a stage prior to and when the user should be filling the IDD 10.

If a fill event is detected (step 1704A) during a time when the user is instructed to fill, the IDD 10 can continue to proceed with the user setup process (step 1704B), and the process takes a time stamp of the fill event (step 1704C). The user is safe to continue with the rest of preparing the IDD for use, ultimately allowing for infusion. The IDD 10 then knows that insulin was only just introduced into a fluid path, thus ensuring that the insulin has not had time to degrade.

If no fill event is detected when a user is instructed to fill for the first time (step 1705A), the process proceeds to step 1705B, which is interpreted by the process to indicate that the user either forgot to fill the IDD 10 or pre-filled the IDD 10. The user may then choose whether to proceed with the setup. In particular, step 1705B allows the user to either (a) try filling the device again in case they forgot to fill the IDD 10 (proceeding back to step 1702), rather than continuing with infusion, or (b) disable the IDD 10 (proceeding to step 1706C), so that they may try filling a different IDD. If the user chooses to disable the IDD 10 (step 1706C), the IDD will shut down, preventing further use. The user would then need to use another IDD if they want to set up an IDD. If the user chooses (a) (proceeding back to step 1702), the device again monitors the pressure in step 1703. If no fill event is detected again after the second attempt, as indicated in step 1706A, the IDD 10 system requires that the user disable the IDD 10, as indicated in step 1706B, and the IDD 10 is disabled in step 1706C, in which case the user may attempt from step 1701 with a new IDD. At any point in the process 1700, the process may proceed, and the user may be allowed to continue. The system then proceeds to step 1704C, in which case the time stamp of the fill event is used to determine whether degradation of the fluid has occurred. If a time sufficient for degradation of the fluid has passed, the IDD 10 automatically shuts down and prevents further use. If an insufficient time has passed, the user is able to proceed to use the IDD 10.

In some embodiments, the threshold amount of fluidic pressure required for the IDD 10 to positively register a fill event, e.g., a $P_{FETH}$, is pre-determined automatically by computing devices 112a and 112b. In an embodiment, the threshold amount of fluidic pressure required for the IDD 10 to positively register a fill event, e.g., $P_{FETH}$, is dynamic depending on any variety of relevant input variables, such as IDD state, environmental readings, or user interface input.

Figure 18:
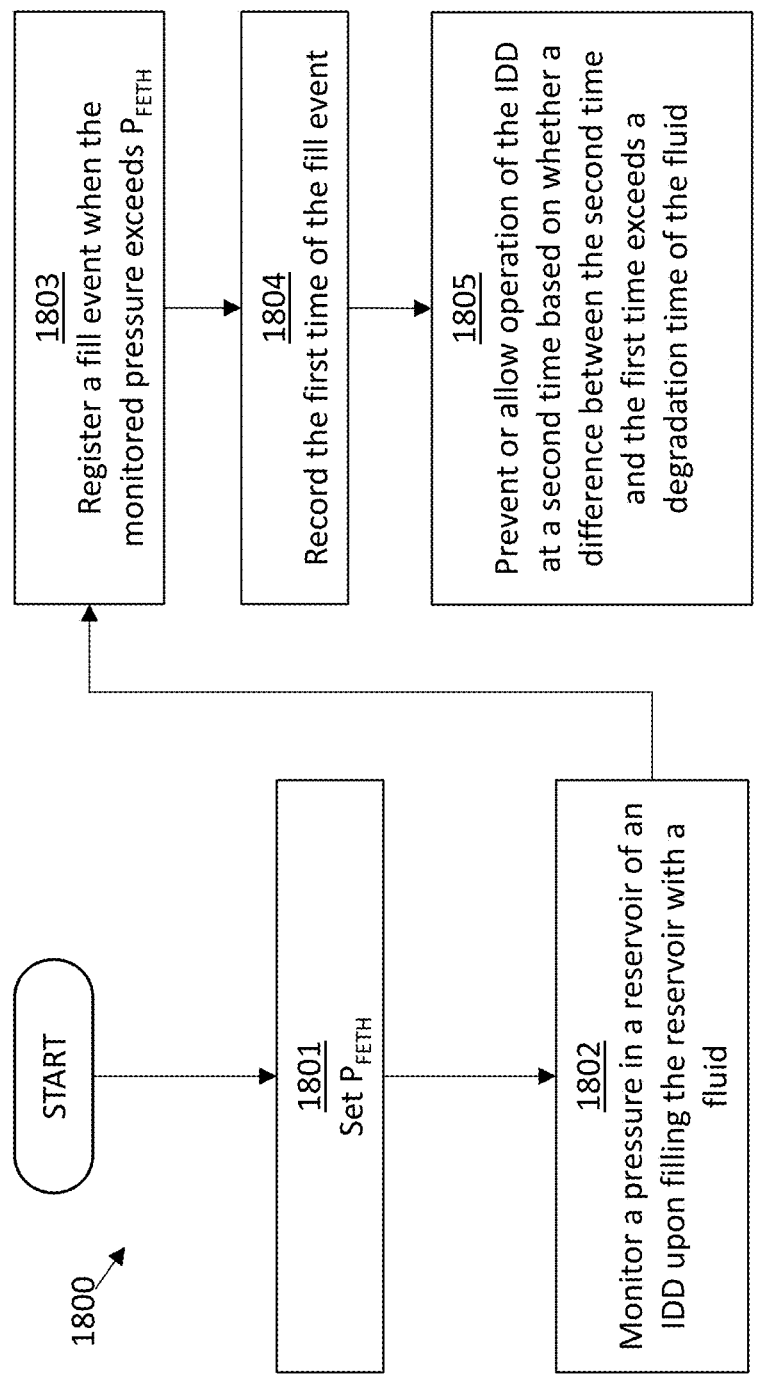
FIG. 18 is a flow chart of an exemplary fill event detection process in an exemplary IDD of the present disclosure.

FIG. 18 illustrates an exemplary process 1800, such as for step 1703 in process 1700, for detecting the fill event. In step 1801, the IDD 10 may set a $P_{FETH}$. In some embodiments, the $P_{FETH}$ is set based on a sum of a pre-defined constant, i.e., a pre-defined baseline pressure, and a pressure measurement when the IDD 10 is first powered on. In some embodiments, the $P_{FETH}$ is set based on a sum of a pre-defined constant, i.e., a pre-defined baseline pressure, and a pressure measurement when the IDD 10 is first paired with the WC. In some embodiments, the $P_{FETH}$ may change depending on a state of IDD 10 and any variety of relevant input variables, such as IDD state, environmental readings, or user interface input. In step 1802, the IDD 10, using the pressure sensor, monitors a pressure in the reservoir 34. If the pressure signal does not exceed $P_{FETH}$, then a fill event is not detected. In step 1803, the IDD 10 may register a fill event when the monitoring pressure exceeds $P_{FETH}$, and a fill event is detected. In step 1804, the time stamp of the fill event (e.g., a "first time" of the fill event) is recorded. Finally, in step 1805, if the user is trying to operate the IDD 10 at a later time, e.g., a second time, the IDD 10 may prevent or allow operation of the fluid delivery device at the second time based on whether a difference between the second time and the first time exceeds a degradation time of the fluid. In particular, the IDD 10 may prevent operation of the fluid delivery device when the difference exceeds the degradation time of the fluid, or the IDD 10 may allow operation of the fluid delivery device when the difference does not exceed the degradation time of the fluid.

In some embodiments, real-time pressure is monitored in the reservoir or the fluid path at various times. For example, in an embodiment, a signal of the pressure sensor is measured/monitored at a sampling rate of 1 Hz+/−5% (e.g., signal is obtained every 0.95-1.05 seconds). During a fill event, if a pressure measurement passes $P_{FETH}$, the fill event is detected. In some embodiments, a transient pressure event is captured by the pressure sensor which results in the signal measurement passing $P_{FETH}$. In some embodiments, $P_{FETH}$ may be a constant-threshold. In some embodiments, $P_{FETH}$ may be driven by an amount of pressure required to push the plunger 54 through the reservoir 34, which may be characterized based on frictional forces produced by the plunger 54. Such frictional forces may be measured by the pressure sensor 50 in the reservoir 34 or fluid path during the filling of fluid at various rates. In some embodiments, $P_{FETH}$ may minimize potential for false positives. In some embodiments, the false positives may occur due to noise factors affecting the pressure, which may include, for example, movement, orientation, and/or pre-fill volume of the IDD 10. These noise factors may be corrected for by the computing devices 112*a* and 112*b*.

In some embodiments, detection of a fill event may be used to determine an expiration or degradation time of the IDD 10 and/or the fluid, such as, for example, insulin. Upon measurement of the fill event, a timer may be incorporated to count down to the expiration or degradation time of the fluid. A lifetime of the IDD 10 or fluid may be directly driven by an amount of time the fluid is exposed to the fluid path, which may be a limiting factor.

Prior systems for detecting fill events require electrical contact with a conductive rod fixed to a plunger, which in turn requires coupling of the detecting with powering on an IDD. Embodiments described herein, however, may decouple the function of powering on an IDD with filling the IDD. Additionally, other systems may instruct users to change their infusion set every 2 or 3 days, but without means of enforcing this change or preventing users from using an infusion set that has not been pre-filled. Further, other systems are not configured to detect fill events for fully detached, free-floating plungers. Thus, the embodiments described herein are compatible with such detached, free-floating plungers, in addition to other attached-plunger architectures.

Figure 19:
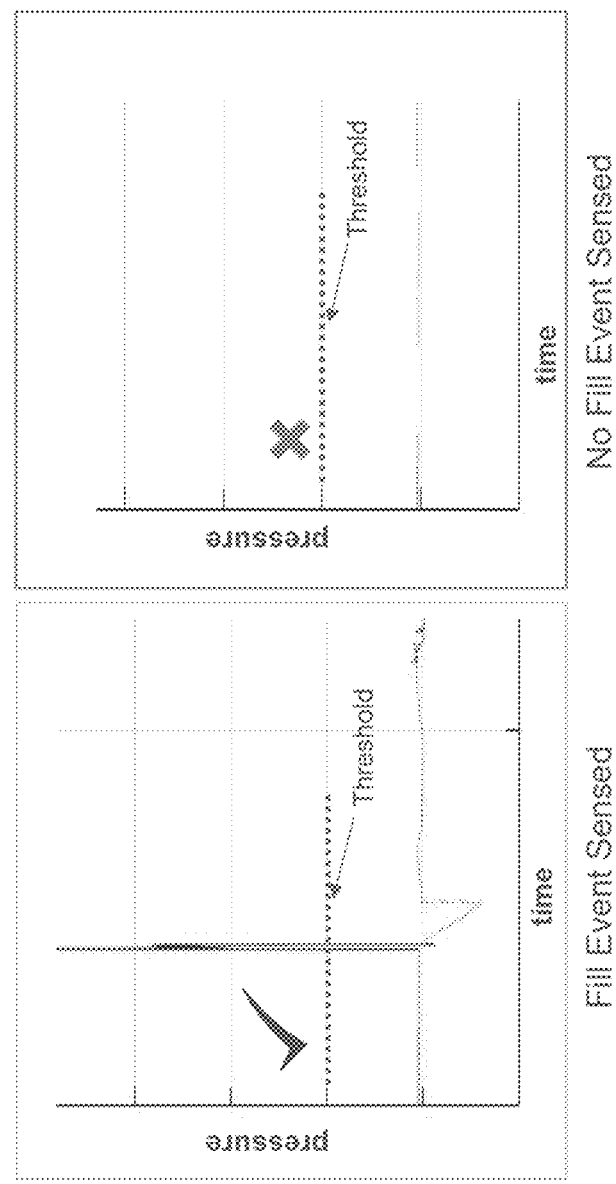
FIGS. 19A-19B are graphical outputs of pressure measured by an exemplary IDD of the present disclosure for detecting a fill event and a lack thereof, respectively.

FIGS. 19A-19B provide exemplary pressure outputs resulting from process 1800 illustrating a constant-threshold $P_{FETH}$ for detecting a fill event. In particular, FIGS. 19A-19B provide graphical outputs of pressure measured by the pressure sensor 50 in the reservoir 34 or fluid path. FIG. 19A depicts a $P_{FETH}$ value (dotted line) set above a baseline pressure being measured. In some embodiments, the baseline pressure is measured when no filling of the IDD 10 has occurred. In some embodiments, the baseline pressure is measured prior to filling of the IDD 10. When the IDD 10 is being filled by the user, a plunger 54 in the reservoir 34 may be forced through the reservoir 34. Friction may exist between the plunger 54 and the walls of the reservoir 34, and a baseline amount of force may need to be applied to the plunger 54 in order to overcome the friction and move the plunger 54 through the reservoir 34. This force against the cross-section of the plunger 54 is equivalent to a fluidic pressure in the reservoir 34. When the pressure rises and provides sufficient force to move the plunger 54, the pressure may exceed the $P_{FETH}$, the system is triggered to process the occurrence of a fill event. Contrarily, in FIG. 19B, a lack of a spike in pressure value causes the system to process the lack of a fill event, thereby either allowing the user to try filling again or to shut down the IDD 10. The $P_{FETH}$ value may be pre-determined based on the known force required to overcome the friction between the plunger 54 and the walls of the reservoir 34.

B. Fill Volume Detection

In reference to step 1002 of FIG. 15, the present disclosure provides systems and methods for detecting a fill volume of a fluid medicament in the IDD 10.

In some embodiments, once a fill event has been detected, it is further desirable to understand additional information about the fill volume of the medicament within the reservoir, i.e., how much medicament (e.g., insulin) has been added to the reservoir so as to know how many doses are possible for downstream operation of the IDD 10. Such user fill volume detection can be implemented using existing infusion pump systems present in most medicament delivery devices. Having an integrated method that detects fill volume using existing hardware provides a technical solution such that users do not have to keep track of and carry a separate filling device to perform the equivalent system functions. Further, the example embodiments of detecting a user fill volume described below may be useful for utilizing one of the occlusion detection systems in an IDD 10.

Figure 20:
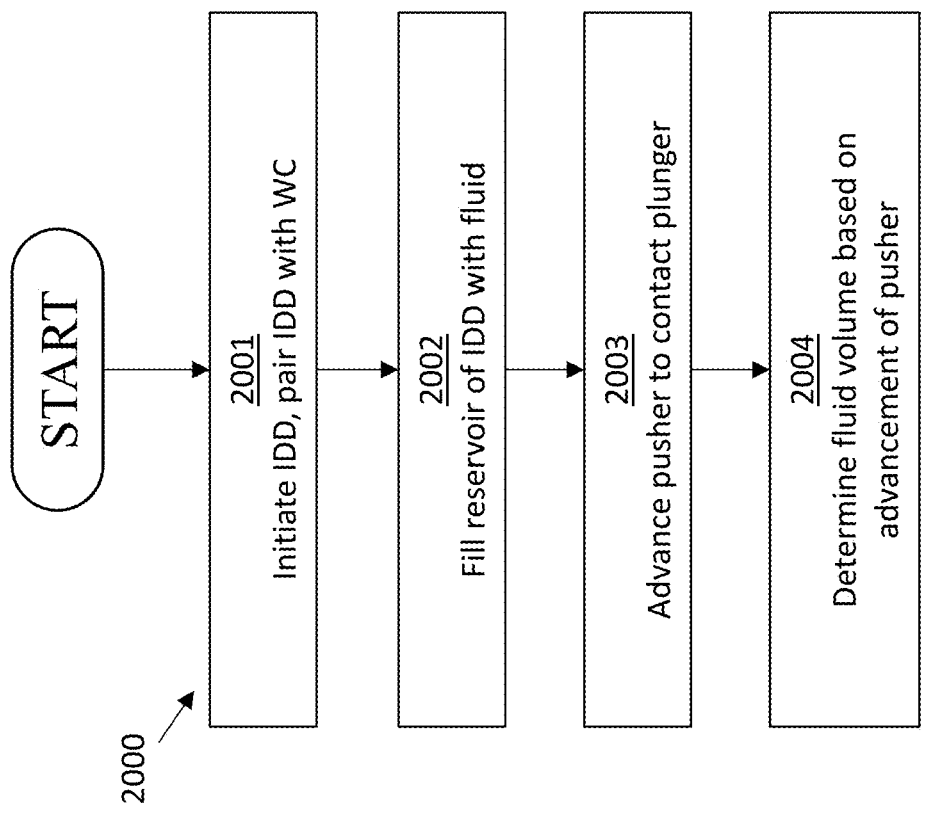
FIG. 20 is an exemplary process for performing a fill event and fill volume detection of an exemplary IDD of the present disclosure.

FIG. 20 illustrates a flow chart of an exemplary process 2000 for performing a fill volume detection of an IDD 10. In some embodiments, the process 2000 includes step 2001, where the IDD 10 is initiated and paired with a computing device, such as a wireless controller (WC) or smartphone running an application/program. The IDD 10 comprises a reservoir 34 that is empty of any medicament and the plunger 54 is positioned at its most distal position inside the reservoir 34. In step 2002, a user then fills the reservoir 34 of the IDD 10 with medicament. At step 2003, once the fill of the medicament has been completed, the fluid path is blocked, and the pump drive mechanism drives the plunger 54 that contacts pusher 44 until a pressure is generated in the reservoir or fluid path. In some embodiments, step 2003 does not initiate until the user or the IDD acknowledges that the reservoir is filled. At step 2004, the MCU tracks positions of pusher 44, and determines the user fill volume of the reservoir 34 by calculating a difference between an initial position and a final position of the pusher 44.

In some embodiments, as a user fills the reservoir 34, the volume of the fluid chamber portion defined in the reservoir 34 by the front (fluid facing) side of the plunger 54 increases. The plunger 54 has the stopper assembly formed of an elastic material to prevent leakage of any medicament retained in the fluid chamber portion of the reservoir 34 such that the plunger 54 is configured to seal the medicament from entering the portion of the reservoir 34 defined by a rear side of the plunger 54.

In some embodiments, once the fill of the medicament has been completed, the MCU performs an initialization process for determining the volume of the medicament, which is filled in the reservoir 34. In some embodiments, once a fill event has been confirmed, as detailed above, a user will send a request to prime the system. After a user sends a request to prime the system or when the medicament is filled in the reservoir 34, the plunger 54 freely moves to a first location between the closed end 34*a* and the capped end 34*b* of the reservoir 34. After filling the medicament, the fluid path is blocked such that any medicament is not allowed to flow in the IDD 10. Once the fill of the medicament has been completed and the fluid path is sealed, the pump drive mechanism begins driving the pusher 44 inside the reservoir 34 from the known position of the pump drive mechanism, which is defined in an initial position (Xo) of the pump drive mechanism, and the MCU keeps track of how much the pusher 44 connected to the pump drive mechanism has advanced from its initial position (Xo), for example, by reading a drive encoder. The drive encoder can be connected to the gear train unit and provide feedback to the MCU by sensing the pump motor action and also the rotation of the drive nut.

An exemplary process for determining a reservoir volume is described in detail with respect to U.S. patent application Ser. No. 17/591,398, filed Feb. 2, 2022, titled "A novel design for detecting user fill volume by utilizing existing occlusion hardware", incorporated herein by reference in its entirety. In some embodiments, the pump drive mechanism continues to drive the plunger 54 that contacts, for example, couples to, pusher 44 until the pressure is generated in the fluid path including the reservoir 34 as the plunger 54 is urged toward the capped end 34b of the reservoir 34 by pusher 44. As described above, the pressure of the fluid path including the reservoir 34 is sensed by the pressure sensor 50 in accordance with an exemplary embodiment of the present disclosure. When the pressure detected by the pressure sensor 50 is greater than, for example, predetermined threshold pressure ($P_{thresh}$), the plunger 54 is stopped at a second location within reservoir 34, and the MCU measures the advanced movement of the pump drive mechanism coupled to the plunger 54 at the second location of the plunger 54 as a current position (Xn) of the pump drive mechanism. Once the fluid path including the reservoir 34 is pressurized, which means that the detected pressure is greater than the predetermined threshold pressure ($P_{thresh}$), it has been understood that all drivetrain components in the pump drive mechanism have been fully engaged with the plunger 54 such that the medicament inside the reservoir 34 can be pushed for delivery. At this stage, the MCU can determine the user fill volume of the reservoir 34 by calculating the difference between the initial position (Xo) and the current position (Xn) of the pump drive mechanism. Accordingly, a volume available to be dispensed can be calculated by taking into account the difference between the initial position (Xo) and the current position (Xn), which volume corresponds to the amount of the medicament filled by the patient (or user). The user fill volume may then be used to compare actual and expected mechanical compliances of the IDD 10 at the corresponding fill volume, as is described below.

In some embodiments, the MCU keeps track of how much the pusher 44 connected to the pump drive mechanism has advanced from its initial position to its final position, for example, by reading the drive encoder (not shown). The drive encoder (not shown) tracks the number of increments it takes to advance the plunger 54 from its initial position to its final position, where each increment corresponds to a certain volume of the medicament. The MCU can then determine, based on the number of increments, an occluded volume, which is the volume of the medicament that would be delivered but for the blockage in the fluid path.

In some embodiments, plunger 54 contact with pusher 44 can be detected instead of, or in conjunction with, building pressure or generating flow. In exemplary implementations, any pressure sensing method or surrogate like current sensing, force sensing, membrane deflection, or torque sensing can be used. For example, because current can correspond to pressure/force/torque/etc., instead of setting a pressure limit, the processing and hardware could be applied to current signals instead of pressure signals.

In some embodiments, the screw train assembly 42 consists of two telescoping screws and a drive nut that interface with the gear train assembly 36, the reservoir cap 37 and the pusher 44. The screw train assembly 42 of the IDD 10 can be similar to the telescoping, simultaneously counter-rotating a sleeve screw and center screw, gear anchor and nut that is rotated via a gear train connected to the motor and gearbox as described in U.S. patent application Ser. No. 17/401,871, which is incorporated herein by reference in its entirety. In use, as the plunger 54 is pushed from the rear of the reservoir 34 towards the tubing ports, the screws telescope simultaneously. The pusher force is reacted back through the screw assembly to the drive nut which is constrained by the internal bracket. Radial constraint is also provided through the internal bracket.

In some embodiments, when the user fills the medicament in the IDD 10, the fluid path fills up to the venting member 27 of the insertion seal assembly 20 first and expels all air in the fluid path before the plunger starts moving. The majority of the volume filled by the user moves the plunger 54 from the closed end 34a of reservoir 34 to an unknown location between the closed end 34a (for example, corresponding to 0 U fill) and a starting known position (for example, corresponding to 310 U fill). An initialization processing starts with the outlet of the fluid path being blocked to liquid flow (for example, by the selectively downstream venting member 27), the reservoir plunger 54 being disposed at the unknown location, and pusher 44 connected to the screw train assembly 42 starting in a known position (Xo).

In some embodiments, after the user has confirmed that fill is completed, the MCU 52 reads the pressure and assigns this pressure to $P_0$. Then, in an exemplary implementation, the screw train assembly 42 starts driving the pusher 44 such that the pusher 44 connected to the screw train assembly 42 moves toward the closed end 34a of the reservoir 34 one step increment for a predetermined distance to take up the screw train compliance in the IDD 10, and the MCU 52 reads the pressure and assigns this pressure to $P_1$, and checks if the one step increment was completed. If the one step increment was not completed and if the pressure is generated and sensed, then the MCU 52 analyzes the pressure ($P_0$) to determine if the sensed pressure ($P_0$) is greater than a predetermined threshold pressure ($P_{thresh}$) (for example, within a range of 5 to 25 psi). If the pressure ($P_0$) is greater than the threshold pressure ($P_{thresh}$), then the plunger 54 has been fully bottomed out, the initialization process is completed, and the user fill volume is determined to be at the initial position (Xo) of the pump drive mechanism. If the pressure ($P_0$) is not greater than the predetermined threshold pressure ($P_{thresh}$), there may be a potential error in delivery device operation because the screw train assembly 42 should be able to advance the pusher 44 until measured pressure is greater than $P_{thresh}$ without stalling.

If the one step increment has been completed, the MCU 52 analyzes both pressures ($P_0$ and $P_1$) to determine if the pressures ($P_0$ and $P_1$) are each greater than the predetermined threshold pressure ($P_{thresh}$). If both pressures ($P_0$ and $P_1$) are each greater than the threshold pressure ($P_{thresh}$), the initialization process is complete and the user fill volume is determined by subtracting a current position (X1) of the screw train assembly 42 with one step increment from the initial position (Xo). In the exemplary embodiment of the present disclosure, the user fill volume is determined by subtracting 0.05 U from 310 U when one step increment of the screw train assembly 42 is completed. If the pressures ($P_0$ and $P_1$) are not greater than the threshold pressure ($P_{thresh}$), the MCU 52 continues to advance the pusher 44 connected to the screw train assembly 42 with a step increment.

In some embodiments, the screw train assembly 42 advances the pusher 44 by one step increment and the MCU 52 checks if the one step increment is completed. When the one step increment of the pump drive mechanism is completed, the MCU 52 checks if both pressures ($P_n$ and $P_{n-1}$) measured at the current position with one step increment (n-step increment) and the previous position before incrementing one step (n-1 step increment) are greater than the predetermined threshold pressure ($P_{thresh}$). In some embodiments, if the one step increment is not completed, the screw train assembly 42 continues to advance. In some embodiments, stalling may be monitored. In some embodiments, if the one step increment is not completed, the MCU 52 checks if the screw train assembly 42 is able to push against the threshold pressure without stalling. If both pressures ($P_n$ and $P_{n-1}$) are each greater than the threshold pressure ($P_{thresh}$), the MCU 52 determines that the initialization process is completed and the user fill volume is calculated by subtracting the current position (Xn) from the initial position (Xo) of the screw train assembly 42. For example, in the exemplary embodiment of the present disclosure, the user fill volume is calculated by subtracting 0.05*n from the initial position (for example, 310 U). In particular, in an exemplary implementation, one step increment of a pusher 44 corresponds to 0.05 U volume displacement.

If both pressures ($P_n$ and $P_{n-1}$) are not greater than the threshold pressure ($P_{thresh}$), the MCU 52 also checks if both pressures ($P_n$ and $P_{n-1}$) are greater than ($P_0+P_{delta}$) (for example, $P_{delta}$=within a range of 1 to 15 psi). If both pressures ($P_n$ and $P_{n-1}$) are greater than the pressures ($P_0+P_{delta}$), the MCU 52 determines that the initialization process is completed and the user fill volume is calculated by subtracting the current position (Xn) from the initial position (Xo) of the screw train assembly 42. For example, in the exemplary embodiment of the present disclosure, the user fill volume is calculated by subtracting 0.05*n from the initial position (for example, 310 U). If the predetermined threshold pressure has not been reached, the MCU 52 begins incrementing according to a user fill volume detection operation. It continues to increment until a pressure builds up. When the pressure criteria have been met, the MCU 52 stops the increments and determines the number of remaining increments corresponding to the user's fill volume by subtracting the current position from the initial position of the screw train assembly 42.

In some embodiments, the screw train assembly 42 will continue to advance in increments until the plunger has advanced forward a set maximum amount. Any more than this advancement may result in too little insulin in the reservoir, so the IDD 10 may prevent any further use. In some embodiments, the IDD 10 may then indicate to the user that they have not filled the reservoir with enough insulin, and may require starting over with a new IDD.

C. Mechanical Compliance Calibration/Air Detection of an IDD after Fill Event and Priming In reference to step 1003 of FIG. 15, the present disclosure provides systems and methods for calibrating a mechanical compliance in the IDD 10.

Once a fill volume has been determined, it is desirable to understand further information about a specific mechanical compliance of an IDD during setup. Because the typical liquid medicaments are incompressible, if a theoretical IDD was perfectly rigid and had no air in the fluid path, it would pressurize instantaneously and infinitely once it pumped the liquid medicament into a device having an occlusion. In reality, however, pressure builds up gradually when devices have an occlusion because of the mechanical compliance of the device and medicament. For example, as the IDD continues to deliver the medicament into the occlusion, the fluid path expands and air compresses to make room for the occluded volume. The magnitude of this mechanical compliance is driven by several factors. Elastomeric components in the fluid path increase compliance, as more fluid can be stored in the expanding elastomers before pressure is generated. Air in the fluid path also increases compliance, since air is compressible and will decrease in volume as pressure builds.

The mechanical compliance of the IDD determines how input flow rate (the amount a plunger advances in the reservoir), outlet flow rate (decreased during an occlusion), and internal pressure (increased during an occlusion) relate to one another. For example, devices with less compliance will generate greater pressure for a given occluded volume, compared to a more compliant device.

Figure 21:
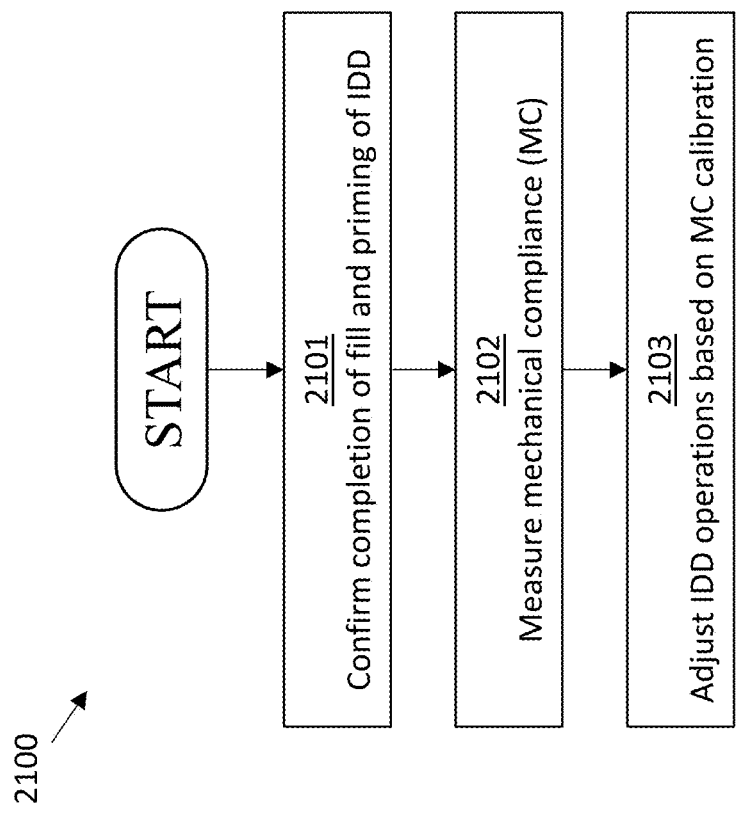
FIG. 21 is an exemplary process for adjusting operating parameters based on a calibration of the mechanical compliance of an exemplary IDD of the present disclosure.

FIG. 21 illustrates a flow chart of an exemplary process 2100 for adjusting operating parameters based on a mechanical compliance calibration process of an IDD 10. In step 2101, after an IDD is paired with a WC, a fill event detection process is performed to confirm a fill event has occurred, and priming of the IDD is initiated, for example, as described above. In step 2102, the mechanical compliance (MC) of the IDD may be calibrated. For example, the specific MC can be determined for the present conditions of the IDD and medicaments, as is described below, and is compared to an expected MC compliance (for example, tested during the manufacture of the IDD). In step 2103, the operations conditions of the IDD may be adjusted depending on the differences between the expected MC and the MC determined during the calibration step.

In some embodiments, the MC calibration process may occur as a step in the setup process of the IDD and may have the ability to determine if the user inadvertently filled the device with any air. If the user inadvertently fills one IDD with more air than another user has filled a different IDD, the MC will be different in the two IDDs. The ability of the compliance calibration of each IDD to detect air can be used to improve patient safety. For example, air in the fluid path, either in the reservoir or dispense fluid path, can result in under-infusion if the user believes that the IDD is delivering a drug, but instead the device is delivering air. The IDD may have several mitigations to prevent the user from filling the reservoir with any air, but there may still be a possible use error. The detection of a large amount of air could potentially prevent the user from proceeding with an infusion. In some embodiments, the IDD could tell the user that there is air in the reservoir or dispense fluid path, or could be used to deactivate the IDD if the air volume poses a danger. A significant volume of air could pose a threat to user safety since the infusion could deliver air instead of the intended drug.

In some embodiments, air detection may also be used to let the user know that there is air in the system but allow the user to proceed with infusion. This could inform users that they may need to change how they are filling the IDD in the future to minimize air, and may allow adjusting of a determined occlusion pressure threshold to account for excess compliance.

Figure 22:
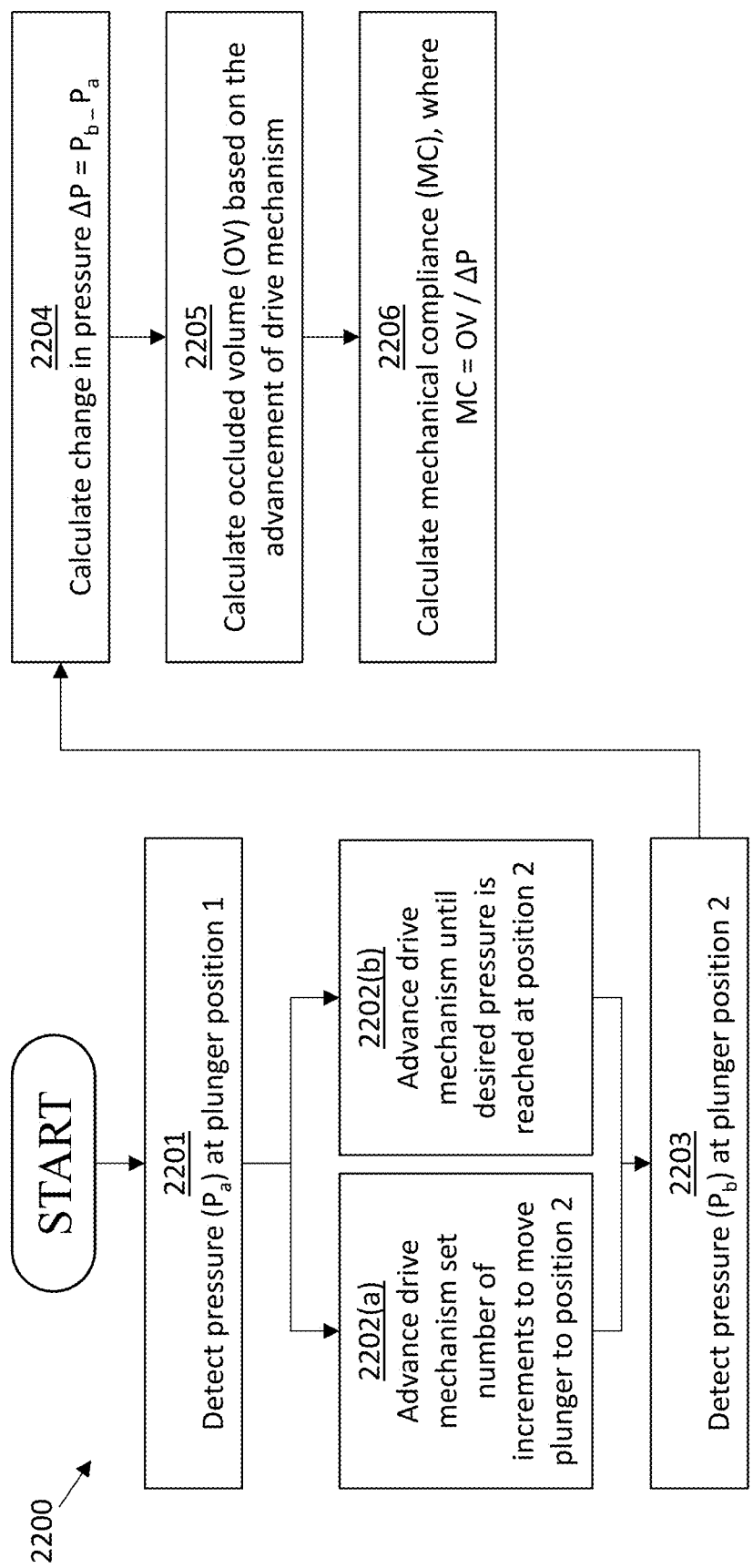
FIG. 22 is an exemplary process for individual compliance calibration during setup of an exemplary IDD of the present disclosure.

In some embodiments, the MC calibration process may be used to optimize occlusion detection, as will be described below, where the amount and function of the pressure increase is dependent not only on the volume of blocked flow, but also on the mechanical compliance of the device. Compliance of an IDD may be well understood, but there is part-to-part variability, and compliance further increases if users fill the IDD with some amount of air. Compliance that is unaccounted for in the occlusion detection system would result in the delayed detection of an occlusion event. By understanding the mechanical compliance of the system and changes thereto throughout the delivery cycle, a more accurate occlusion detection process can be developed. The value of mechanical compliance can be used to set a dynamic pressure threshold to determine an occurrence of an occlusion in the system. If the calibration step reveals that there is a difference between the specific MC and the expected MC, the IDD may then use this mechanical compliance assessment to tune the occlusion detection process to the device-specific compliance. The tuned process may then minimize false positive occlusion detection if the IDD-specific compliance is less than a programmed nominal compliance level. This may decrease the pressure threshold of occlusion detection to prevent missed occlusions if the device-specific compliance is greater than the assumed nominal compliance level. FIG. 22 illustrates an exemplary mechanical compliance calibration process for individual compliance assessment 2200, comprising compliance calibration after priming but prior to removal of an insertion seal assembly, which occurs during setup of the IDD 10. The IDD 10 may detect the occurrence of occlusions by monitoring, using the pressure sensor 50, the pressure in an IDD reservoir or dispense fluid path. Occlusion detection in this way relies on an understanding of the mechanical compliance of the IDD 10, e.g., the relationship between an occluded volume and a pressure generated at the pressure sensor 50, as the amount and function of the pressure increase is dependent both on the volume of blocked flow and the mechanical compliance of the device. Because of part-to-part variability between different IDDs, there may be mechanical compliance that is unaccounted for in the occlusion detection system, resulting in the delayed detection of an occlusion event. By understanding the mechanical compliance of each IDD 10 and changes thereto throughout the delivery cycle, a more accurate occlusion detection process can be developed. Thus, an individual compliance assessment may be used to tune an occlusion detection process to a device-specific compliance, so as to more accurately detect an occlusion based on the IDD-specific compliance relative to a programmed nominal compliance level. This may further minimize false positive occlusion detection to prevent missed occlusions if the device-specific compliance is different from the assumed nominal compliance level.

After the IDD 10 has determined that the reservoir 34 has been filled such that the pusher 44 is engaged with the plunger 54, the MCU may perform the individual compliance assessment 2200. In step 2201 of the individual compliance assessment 2200, an MCU in the IDD 10 reads the pressure via pressure sensor 50, when the plunger is at a first plunger position, and assigns this pressure as a first pressure ($P_a$). In steps 2202(a) and 2202(b), the MCU then causes the drive mechanism to drive the pusher 44 toward the closed end 34a of the reservoir 34 by one or more increments until a specific condition is met, based on how the mechanical compliance (MC) of the IDD 10 is to be calculated. Specifically, step 2202(a) requires the drive mechanism to drive the pusher 44 a specific number of increments to move the plunger 54 to a second plunger position. Alternatively, step 2202(b) requires the drive mechanism to drive the pusher 44 until a predetermined second pressure is reached, which may vary in the number of increments that the pusher 44 is driven relative to the number of increments in step 2202(a). Once the second pressure is reached, the MCU records the new position as the second plunger position. Step 2203 comprises detecting and recording the pressure ($P_b$) at the second plunger position.

Steps 2204 and 2205 comprise calculating the change in pressure (ΔP) and the occluded volume (OV), respectively. ΔP is calculated as the difference between the $P_a$ measured at the first plunger position and $P_b$ at the second plunger position. OV is calculated based on the number of increments driven at either 2202(a) or 2202(b). In step 2206, the MCU calculates the mechanical compliance (MC) based on the ΔP and OV, such that MC=OV/ΔP.

The individual compliance assessment 2200 may be used for several functions. One non-limiting exemplary embodiment is provided in FIGS. 23A-23B by using the calculated MC values to determine a volume of air that may have accidentally been added to the reservoir 34. The ability to detect air in the IDD 10 is a particular feature that may improve patient safety. Specifically, air in the reservoir or dispense fluid path can result in under-infusion of the medicament if air is being delivered to the user instead of the medicament, and the user has not been notified by the IDD of the under-infusion. Further, detection of a large amount of air could potentially prevent the user from proceeding with an infusion. Knowing of the volume of air in the reservoir or dispense fluid path may be used to deactivate the IDD if the air volume poses a danger, or to notify the user to proceed with caution during infusions. Additionally, if the user fills one IDD with more air than another user has filled a different IDD, the MC may be different between the IDDs, thereby requiring adequate understanding of how the air volume may affect the MC of the IDD in use.

Figure 23B:
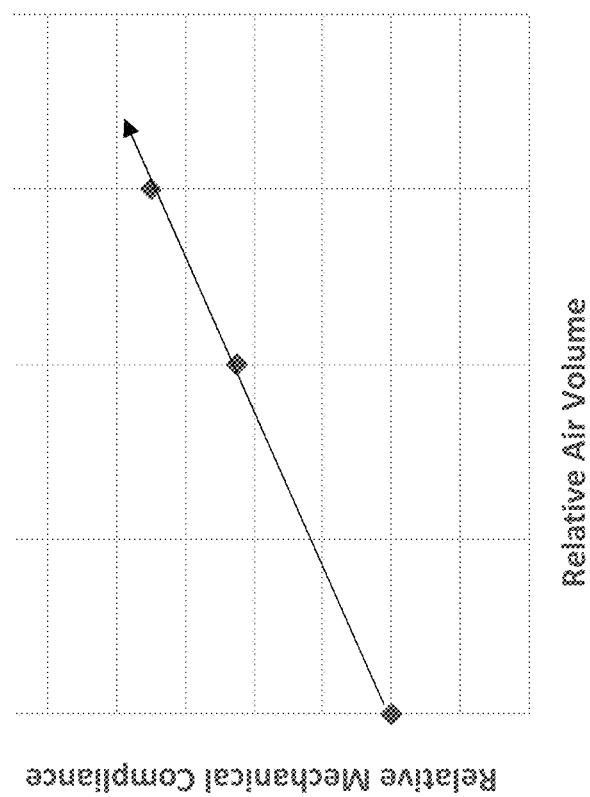
FIGS. 23A-23B show exemplary scatterplots illustrating the change in compliance as a result of filling reservoirs with specific volumes of air and generating additional pressurization following fill detection.
Figure 23A:
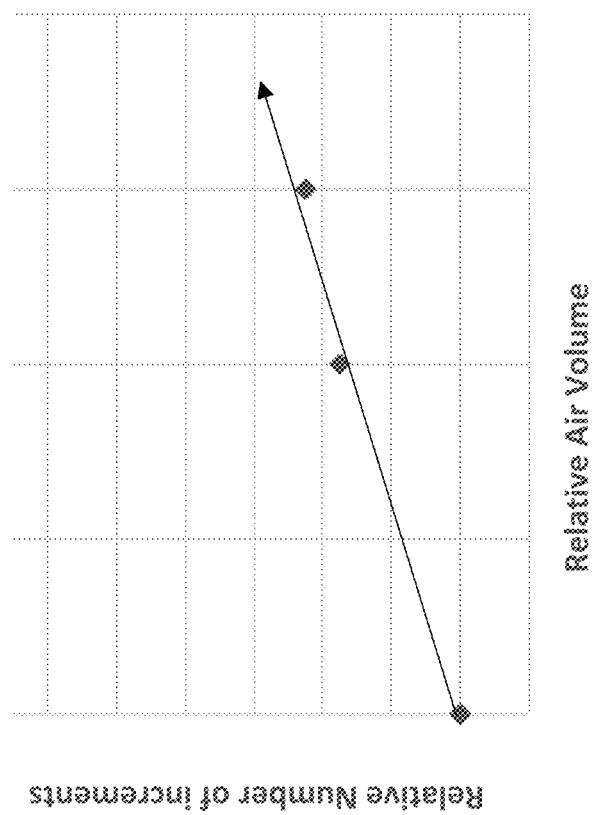

FIGS. 23A-23B illustrate exemplary scatterplots showing the MC with varying amounts of air within the reservoir 34. Following fill event detection, the number of increments the pusher 44 may advance to reach a second pressure $P_b$ following fill detection may vary based on the volume of air inadvertently added to the reservoir 34 (as shown in FIG. 23A). Each data point was obtained by advancing the drive mechanism of the IDD to generate a first pressure ($P_a$), holding the pressure, and then advancing the drive mechanism again until a second pressure ($P_b$) was generated. The difference in the number of increments required to obtain the second pressure ($P_b$) with air relative to liquid reflects a difference in the air volume within the reservoir 34, which further reflects the difference in MC of the IDD 10 as shown in FIG. 23B. In some embodiments, the air volume in the reservoir may be detected using mechanical compliance. In some embodiment, the actual mechanical compliance may be different than expected compliance as air may change the mechanical compliance. In some embodiments, the difference in compliance may be due to a change in volume of air in the reservoir.

Figure 24:
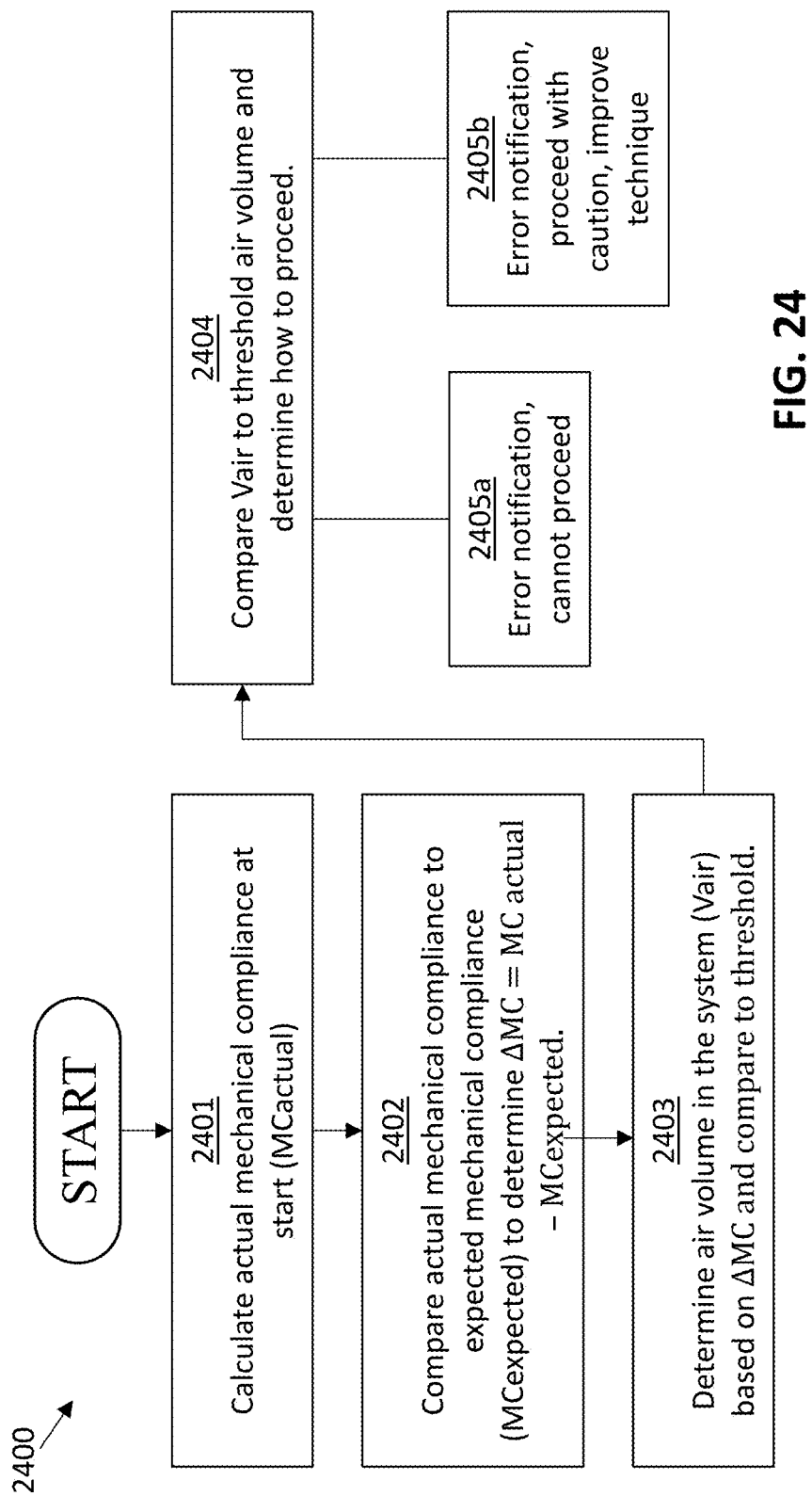
FIG. 24 illustrates an exemplary mechanical compliance calibration process for determining an MC of an exemplary IDD of the present disclosure when the user has filled the reservoir with a volume of air.

FIG. 24 illustrates an exemplary process 2400 for using an MC of the IDD 10 to determine a volume of inadvertent air in the medicament in the reservoir. As shown in FIGS. 23A-23B, if the IDD 10 has a significant volume of air in the reservoir, the pusher 44 would need to advance further to generate a given amount of pressure. An approximate volume of air in the IDD 10 may be determined based on a controlled pressurization during device setup.

Step 2401 comprises calculating an actual mechanical compliance ($MC_{Actual}$) at the beginning of operation of the IDD 10, which will be based on a pressure reading from the pressure sensor 50 and the corresponding detected volume of the reservoir at the pressure reading. Step 2402 comprises calculating a difference in MC values (ΔMC) by comparing the $MC_{Actual}$ to the expected mechanical compliance ($MC_{Expected}$), such that $\Delta MC = MC_{Actual} - MC_{Expected}$. In some embodiments, $MC_{Expected}$ may be determined based on the MC values, at the corresponding detected volume, obtained from step 2206 of the individual compliance assessment 2200. This may be the case if there is no air in the reservoir 34 or fluid path such that the $MC_{Expected}$ and $MC_{Actual}$ are equivalent. In some embodiments, $MC_{Actual}$ may be determined based on the MC values, at the corresponding detected volume, obtained from step 2206 of the individual compliance assessment 2200. Step 2403 comprises determining the potential volume of air in the reservoir 34 ($V_{Air}$) of the IDD 10, based on the ΔMC. Specifically, the ΔMC allows the IDD 10 to interpolate the volume required for the pressure sensor 50 to detect the pressure reading at the $MC_{Actual}$, thus any difference in the volume in the reservoir 34 relative to the expected volume used to obtain $MC_{Expected}$ may correspond to the $V_{Air}$. Next, step 2404 comprises comparing $V_{Air}$ to a predetermined threshold air volume, such that the threshold air volume may be programmed to indicate a dangerous amount of air volume or may be within a range where a safety risk is less severe. Based on the comparison to the threshold air volume, the user may be notified of an error in dispensing medicament (step 2405a), and may prevent the IDD 10 from further infusion. Alternatively, as shown in step 2405b, if the air volume is within an acceptable safety threshold, the IDD 10 may be allowed to proceed for further infusion but with modified infusion parameters so as to account for the $V_{Air}$, and thus higher MC. Even though the IDD 10 is allowed to proceed, the user may still be notified of the air volume in the medicament to improve the user's filling technique.

In some embodiments, determining an expected MC of the IDD 10 may develop reference data for various volumes of medicament in the reservoir, various volumes of air in the medicament, or both. Specifically, determining $MC_{Expected}$ values, such as those used in step 2402 of process 2400, to calibrate an individual IDD 10 prior to use with a patient at specified liquid (LV) and air (AV) volumes. Using the $MC_{Expected}$ values at different LV and/or AV values, the MCU may calculate an air volume in the reservoir 34 for determining how to proceed with infusion. Further, different MC curves may be determined so as to generate different occlusion pressure thresholds based on the amount of air that is present in the reservoir. Once the AV is calculated, then the pressure measurement may be compared to the corresponding threshold based on the $MC_{Expected}$ at that particular volume in the reservoir.

In some embodiments, for measuring an MC of the IDD 10, data from the pressure sensor 50 may be supplemented with a corresponding signal from a different sensor, such as, for example, a force sensor, a flow sensor, or a motor current sensor. In some embodiments, the pressure sensor 50 is an air-in-line sensor.

D. Occlusion Detection after Removal of Insertion Seal Assembly

In reference to step 1004 of FIG. 15, the present disclosure provides systems and methods for detecting an occlusion after detection of the fill event, priming of the IDD 10, detection of the fill volume, and removal of the insertion seal assembly.

In some embodiments, the IDD may check for internal occlusions in an IDD 10 prior to the user using the IDD 10, e.g., prior to applying the IDD 10 to a patient's body, prior to the user activating an insertion mechanism for inserting a catheter, and/or prior to a user requesting therapy. This can help prevent users from proceeding with an IDD 10 if an internal occlusion is detected. The IDD 10 may do so, for example, by monitoring a gauge pressure of the internal fluid path as components in the fluid path are added to or removed from the IDD 10 as part of the setup procedure. In some embodiments, the IDD 10 monitors the gauge pressure during removal of the insertion seal assembly 20 after a priming sequence.

Figure 25:
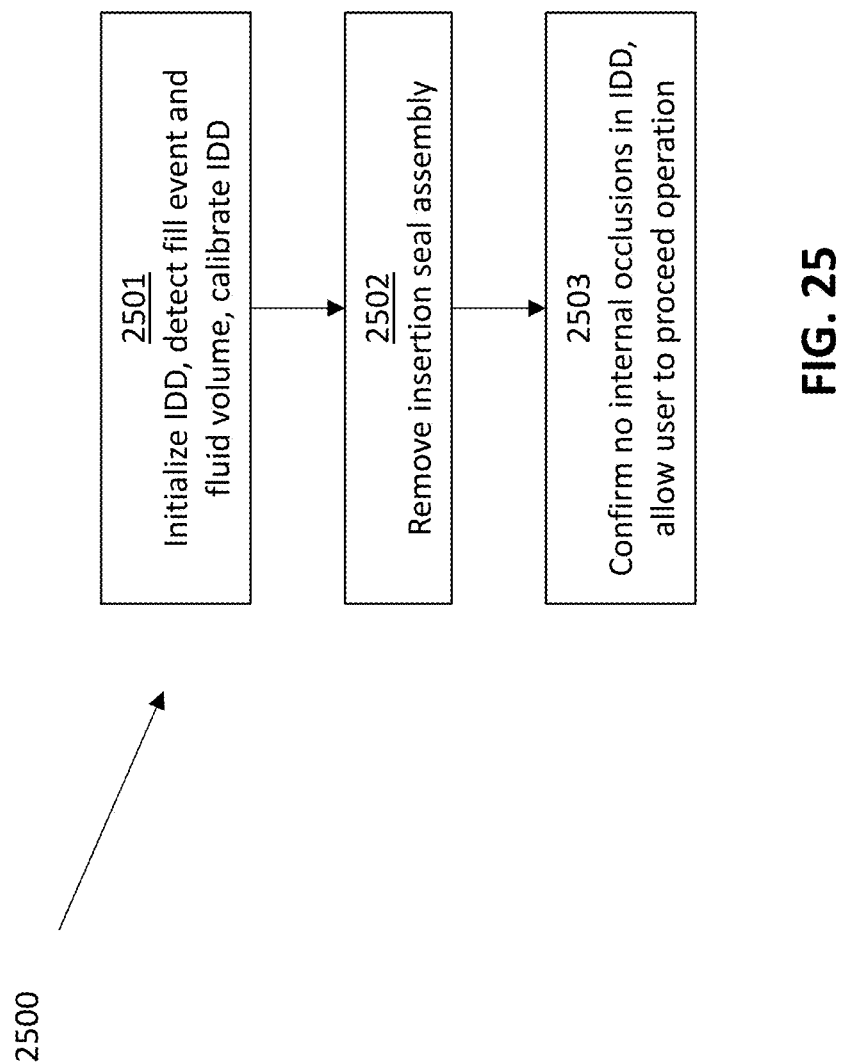
FIG. 25 is an exemplary method for a pressure check following removal of the insertion seal assembly.

FIG. 25 illustrates a flow chart of an exemplary process 2500 for checking for internal occlusions in an IDD 10. Step 2501 of process 2500 begins with initializing the IDD 10, filling of the reservoir with a medicament (e.g., insulin), detecting the fill event, determining a fill volume, and calibrating the IDD. Step 2502 then comprises removal of the insertion seal assembly. Step 2503 comprises checking the IDD 10 for any internal occlusions and, after confirming there are none, allowing the user to proceed with operation of IDD 10.

As described above, during priming, pressure builds in the fluid path and at the removal of the insertion seal assembly 20, the pressure would theoretically decrease to atmospheric pressure if there were no occlusions. This step serves as an opportunity to obtain an "auto-zero" pressure, or a new reference pressure for an equilibrated fluid path, $P_{EQ}$. It can be helpful to update the reference pressure prior to dosing to eliminate any environmental or time drift of the pressure sensor 50. If an occlusion is present, this pressure would read higher than those attributable to the use environment or shelf life. If the pressure reaches a threshold indicative of an occlusion, it will prevent use of the IDD and alert the user. A reading lower than normal would indicate another form of a malfunction that should also trigger an alert to the user.

In an embodiment, the IDD 10 may detect whether the pressure after the insertion seal assembly 20 removal is within an expected range relative to a set point, such as, for example, $P_{EQ}$ as described above, prior to injection of medicament. The IDD 10 could then alert the user if the pressure exceeds this threshold and prevent users from proceeding with using the IDD 10.

Figure 26:
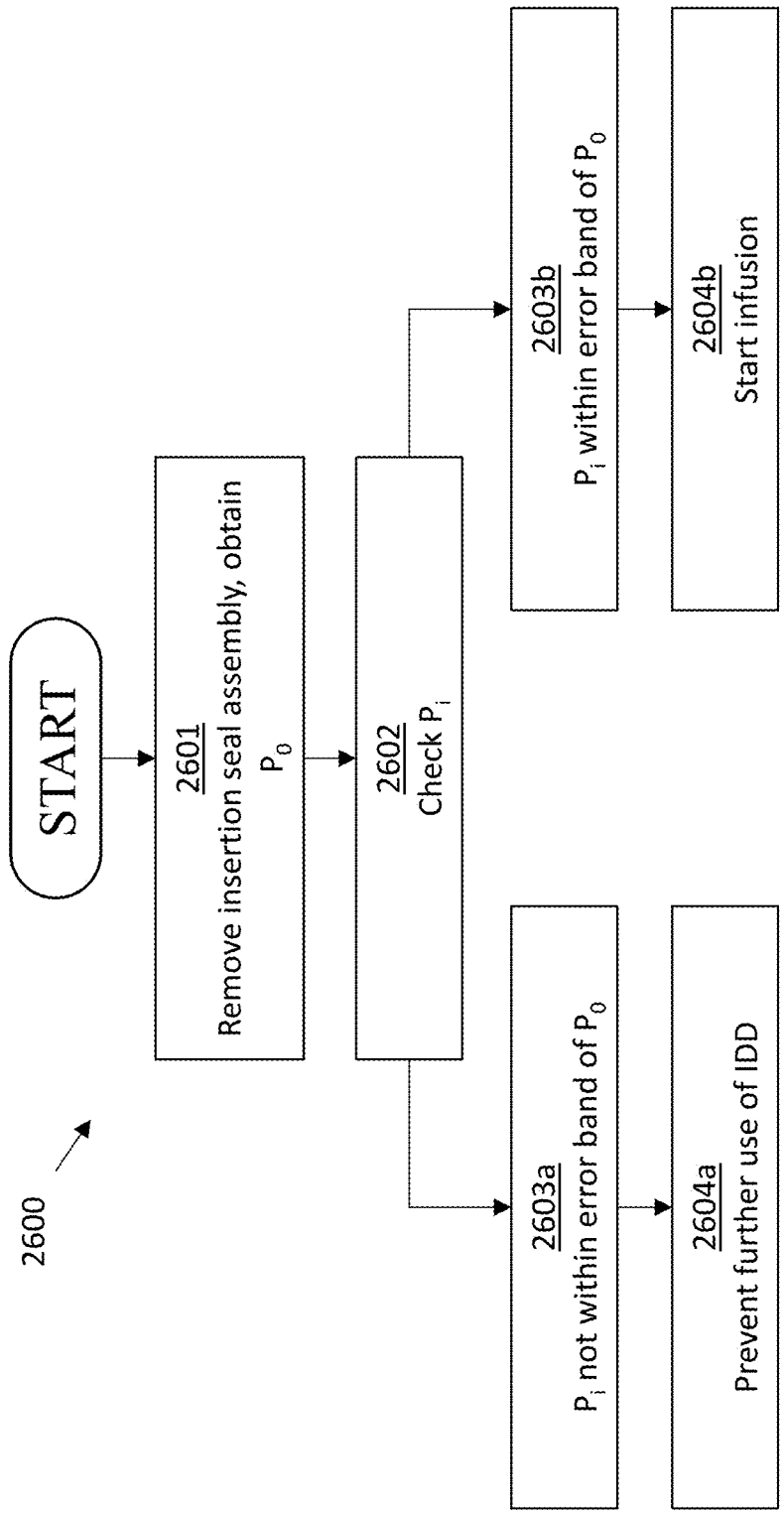
FIG. 26 is an exemplary method for a pressure check following removal of the insertion seal assembly.

FIG. 26 illustrates an exemplary method 2600 for determining if a fluid path of an IDD 10 has an occlusion prior to use. During the priming sequence, the gauge pressure of the fluid path increases as the screw train assembly 42 begins to advance the plunger 54, as was described above. Step 2601 comprises, following priming, instructing the user to remove the insertion seal assembly 20 from the IDD 10 to equalize the pressure of the fluid path with atmospheric pressure, i.e., $P_0$. In a fluid path with no obstructions, this pressure would relieve quickly and at a predictable rate, with some variation expected due to fluid path geometry variability and other environmental factors. Empirical testing of manufactured products can determine the expected duration of time to relieve the pressure, and whether any pressure is maintained after equalization due to head pressure or signal noise.

Step 2602 comprises reading the pressure sensor at a set duration after the removal of the insertion seal assembly 20, a reading referred to as $P_1$. In step 2603a, the pressure sensor determines that the pressure does not decay as expected, thus indicating a higher-than normal flow restriction to prevent the IDD 10 from further use in step 2604a. In step 2603b, the IDD 10 determines whether the pressure decay rate is within an expected range for an IDD with no occlusion, thus proceeding with infusion in step 2604b.

In some embodiments, for a manual insertion mechanism, this implementation could benefit from waiting a pre-determined amount of time between the detected removal of the insertion seal assembly 20 and the reading of the pressure $P_i$. This time should be long enough for the pressure reading to accurately detect the pressure decay rate of the fluid path, but brief enough that pressure $P_i$ can be logged before the system is applied to the user's body and inserted into tissue. For an automatic insertion mechanism, pressure $P_i$ could be recorded just prior to the insertion of the fluid path into user tissue.

E. Detecting Fluid Path Component Deployment of an Infusion Delivery Device

In reference to step 1005 of FIG. 15, the present disclosure provides systems and methods for detecting the deployment of a fluid path component of the IDD 10 after completion of one or more of fill event detection, fill volume detection, and MC self-calibration of the IDD 10.

In particular, in some embodiments, a fluid path of the IDD 10 is primed prior to deployment of one or more components of the fluid path into the patient's tissue or skin. In some embodiments, the one or more components of the fluid path for deployment comprises one or more of a catheter or a needle. In some embodiments, priming the fluid path generally involves flushing the fluid path with liquid and removing air bubbles from the fluid path. Priming the fluid path prior to deployment of one or more components of the fluid path into the patient's tissue can avoid administration of air bubbles or primed fluid from the IDD 10 into the patient's body. Similarly, the one or more components of the fluid path should be deployed into the patient's tissue or skin prior to administration of a dose of medicament from the IDD 10. Doing so can prevent the wasting of one or more doses of medicament by expelling a dose of medicament from the fluid path when one or more components of the fluid path are not in the patient's tissue. Therefore, it can be beneficial to determine when an insertion mechanism, e.g., insertion mechanism 22, deploys the one or more components of the fluid path from the housing of the IDD 10 and into the patient's tissue to ensure that the IDD 10 is being used or operated in a desired sequence.

In some embodiments, the IDD 10 of the present disclosure can include an insertion mechanism 22, as shown in FIGS. 11A-11E, for deploying one or more components of the fluid path, such as the catheter or the needle, or both, to deliver fluid, from the housing of the IDD 10 and inserting the one or more components of the fluid path into the patient's tissue. In some embodiments, at least one of a needle or a catheter can be deployed by the insertion mechanism 22 and inserted into the patient's tissue. The IDD 10 can further include one or more sensors positioned in or along the fluid path for sensing a property of the fluid path. The property of the fluid path can be a property of the fluid in the fluid path. In some embodiments, merely as an example, the property of the fluid path can be the pressure in the fluid path. In some embodiments, the property of the fluid path can be a sensed flow of fluid in the fluid path. In some embodiments, multiple sensors can be used to sense multiple properties of the fluid path.

In some embodiments, detecting the deployment of the one or more components of the fluid path is based on a change in length of the fluid path. For example, in its pre-deployment state, the needle is disposed within the catheter, which provides a first length to the fluid path. During the insertion of a catheter 48 into tissue, a needle 46 may pierce the skin and guide the catheter 48 into place. Then, the needle 46 may retract and leave the catheter 48 embedded in the tissue. This needle retraction introduces the catheter as additional volume in the fluid path, and thus may extend a length of the fluid path to a second length longer than the first length. As a result, the pressure in the fluid path may experience a measurable drop and generate a negative pressure when the catheter 48 or needle 46 is deployed. Since the mass of fluid and air in the fluid path has not changed, the slight addition of the volume of the catheter 48 leads to the negative pressurization, which may be detected by the pressure sensor 50. FIGS. 11B and 11E, above, show the expansion of the fluid path as the catheter leaves the needle following deployment.

Figure 27:
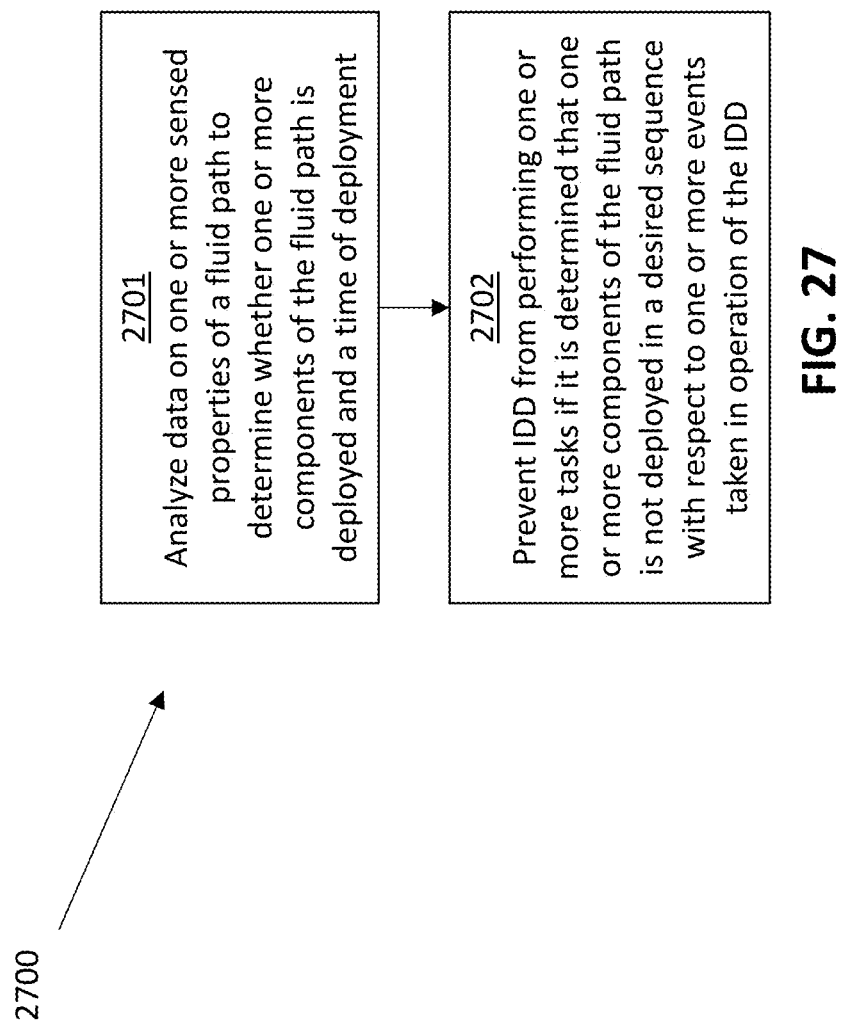
FIG. 27 is a flow chart of an exemplary process for detecting deployment of a fluid path.

FIG. 27 illustrates a flow chart of an exemplary process 2700 for the IDD 10 to carry out, based on sensed data from the one or more sensors, e.g., pressure sensor 50, positioned in or along the fluid path. At a step 2701, sensed data from the one or more sensors on the one or more properties of the fluid path can be analyzed to determine whether the one or more components of the fluid path, such as the catheter or needle, are deployed and, if deployed, a time when the one or more components of the fluid path were deployed from the housing of the IDD 10 (and into the patient's tissue, for instance). Particularly, there may be a spike or change in the detected property of the fluid path when the one or more fluid path components are deployed. At a step 2702, if it is determined that the fluid path of the IDD 10 is not deployed in a desired sequence with respect to one or more other events taken in operation of the IDD 10, the IDD 10 can be prevented from performing one or more tasks. For instance, if it is determined based on the sensed data that the one or more components of the fluid path were deployed from the housing of the IDD 10 (and likely inserted into the patient's tissue) prior to priming of the fluid path, the user can be prevented from then priming the fluid path or using the IDD 10 to administer a dose of medicament.

Figure 28:
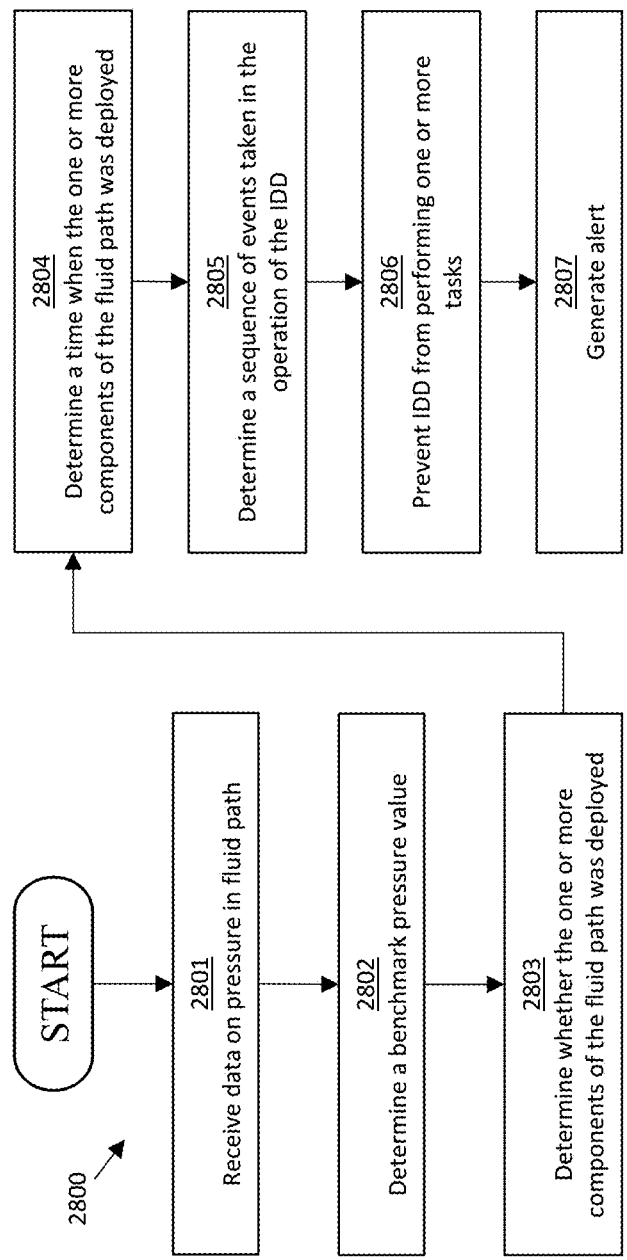
FIG. 28 is a flow chart of an exemplary process for detecting deployment of a fluid path.

FIG. 28 illustrates an example process 2800 for detecting deployment of the one or more components of the fluid path. In some embodiments, process 2800 can be carried out by any of the above-described computing devices for determining when one or more components of a fluid path of an IDD 10 are deployed from a housing of the IDD 10. At a step 2801 of the process 2800, data on pressure in the fluid path of the IDD 10 can be gathered. The data on the pressure in the fluid path can be gathered by the pressure sensor 50 that is positioned along the fluid path.

At a step 2802 of the process 2800, one or more threshold pressure values can be determined. The one or more threshold pressure values can be values to which the data on the pressure in the fluid path gathered in the step 2801 are compared. In some embodiments, the threshold pressure values can include one or more of an upper pressure threshold, a lower pressure threshold, or upper and lower threshold values (defining a range of pressures therebetween) of pressure in the fluid path. In some embodiments, the threshold pressure value can include a time, for example, an amount of time for a pressure threshold to be exceeded. In some embodiments the threshold pressure value can be a threshold rolling average of pressure in the fluid path over a timeframe of desired length (i.e., a threshold moving average). In some embodiments, the threshold pressure value can include a threshold rate of change of pressure. In some embodiments, the one or more threshold pressure values can include a threshold (e.g., upper threshold, lower threshold, or both upper and lower thresholds) rate of change of pressure in the fluid path. In some embodiments, the threshold pressure value can be a nominal pressure signature or pattern of pressure. In some embodiments, the threshold pressure value can be determined based on one or more inputs. For instance, in some embodiments, the threshold pressure value can be determined based on the detected medicament fill volume in the reservoir 34. The threshold pressure value can be determined based on any number of variables or characteristics relating to the IDD 10 and/or medicament contained in the IDD 10 (e.g., type of medicament, amount of medicament filled in the reservoir 34, particular pump or drive system architecture of the IDD 10, the expected length or available volume of the fluid path in the pre-deployed configuration, the expected length or available volume of the fluid path in the deployed configuration, the location of the pressure sensor 50 in the fluid path, etc.).

Still referring to the step 2802, the threshold pressure value can be determined such that the threshold pressure value is indicative of a known event relating to the operation or use of the IDD 10. For example, the threshold pressure value can be determined such that when an event relating to the IDD 10 takes place (e.g., deployment of the one or more components of the fluid path, and in some embodiments the catheter 48 specifically, or removal of the insertion seal assembly 20), the threshold pressure value can be expected to be exceeded or deviated from. In some embodiments, the threshold pressure value can be determined based on experimental data and/or machine learning processes. The experimental data can relate to monitored pressure of the fluid path of an IDD 10 during operation of the IDD 10, and particularly monitored pressure at a time when one or more events are known to occur. The machine learning processes can be trained on experimental data containing monitored pressure in a fluid path of an IDD 10 and known times of one or more events of interest occurring.

At a step 2803 of the process 2800, it can be determined whether the one or more components of the fluid path (e.g., the catheter 48, needle 46) were deployed from the bottom surface of the housing of the IDD 10. In some embodiments, it can be determined that the fluid path was deployed when the detected pressure in the fluid path (determined in step 2801) exceeds the threshold pressure value (determined in step 2802). For instance, it can be determined that the one or more components of the fluid path were deployed (e.g., the catheter 48, needle 46 extended from the housing of the IDD 10) when the detected pressure in the fluid path exceeds a threshold value, exceeds a threshold value for a set amount of time, exceeds a threshold average pressure value, and/or exceeds a threshold rate of change, etc. In some embodiments, it can be determined that the fluid path was deployed when the pressure signature of the detected pressure in the fluid path deviates from a nominal pressure signature. In the corollary, it can be determined that the fluid path has not been deployed when the detected pressure in the fluid path does not exceed the threshold pressure value. Similarly, it can be determined that the one or more components of the fluid path has not been deployed when the pressure signature of the detected pressure in the fluid path does not deviate from a nominal pressure signature.

In some embodiments, it can be directly determined whether the one or more components of the fluid path was deployed. For instance, if the threshold pressure value is determined and set as being indicative of the one or more components of the fluid path being deployed and it is determined that the detected pressure in the fluid path exceeds or deviates from the threshold pressure value, then it can be directly determined that the one or more components of the fluid path was deployed.

At a step 2804 of the process 2800, a time at which the one or more components of the fluid path was deployed from the housing of the IDD 10 can be determined. Particularly, in some embodiments, the time at which the detected pressure in the fluid path exceeds or deviates from the threshold pressure value can be determined. The determined time can be attributed as the time that the one or more components of the fluid path was deployed. In some embodiments where the deployment of the one or more components of the fluid path is indirectly determined based on the determination that the insertion seal assembly 20 was removed from the IDD 10, the time that the insertion seal assembly 20 was removed can be determined and assigned as the time of deployment of the one or more components of the fluid path (based on the assumption that the one or more components of the fluid path is deployed shortly or immediately after removal of the insertion seal assembly 20).

At a step 2805 of the process 2800, the sequence of events taken during the operation of the IDD 10 can be determined. Particularly, in some embodiments, it can be determined whether the deployment of the one or more components of the fluid path has occurred before priming the fluid path (e.g., it can be determined that as of the time of deployment of the one or more components of the fluid path, the fluid path has not been primed). In some embodiments, it can be determined whether the priming of the fluid path has occurred before deployment of the one or more components of the fluid path (e.g., it can be determined that as of the time of priming the fluid path, the one or more components of the fluid path have not been deployed). In some embodiments, it can be determined whether the one or more components of the fluid path have been deployed prior to an instruction to deliver a dose of medicament or prior to a scheduled delivery of a dose of medicament (e.g., it can be determined, at the time the IDD 10 is instructed to or scheduled to deliver a dose of medicament, whether the one or more components of the fluid path have been deployed).

At a step 2806 of the process 2800, the IDD 10 can be prevented from performing one or more tasks. In some embodiments, the IDD 10 can be prevented from performing one or more tasks based on the sequence of events taken during the operation of the IDD 10 determined during the step 2805. For instance, in some embodiments, if it is determined that the one or more components of the fluid path has been deployed prior to priming the fluid path, the IDD 10 can be prevented from both priming the fluid path and delivering a dose of medicament. In some embodiments, if it is determined that the one or more components of the fluid path has not been deployed, the IDD 10 can be prevented from delivering an instructed or scheduled dose of medicament (even if priming has already occurred). In some embodiments, the IDD 10 can be prevented from performing one or more tasks out of a desired sequence of operation of the IDD 10. In some embodiments, the IDD 10 can be prevented from performing the one or more tasks by locking a user out of initiating the one or more tasks (e.g., disabling one or more selectable icons on a user input device, not transmitting a particular instruction provided by the user, etc.). In some embodiments, the IDD 10 can be prevented from performing the one or more tasks by disabling the IDD 10 from performing the one or more tasks (e.g., disabling the IDD 10 by electrical and/or mechanical means from executing an instruction to perform the one or more tasks).

In a step 2807 of the process 2800, an alert can be generated to the user regarding operation of the IDD 10. In some embodiments, the alert can be provided on the IDD 10. In some embodiments, the alert can be provided on a remote device, such as a wireless controller or external computing device. The alert can be visual, auditory, and/or haptic. In some embodiments, the alert can indicate to a user when the IDD 10 is prevented from performing one or more tasks. For instance, in some embodiments, the alert can indicate that the IDD 10 is prevented from both priming the fluid path and delivering a dose of medicament. In such cases, the alert can further include a prompt for the user to discard the IDD 10, as the IDD 10 cannot be used for its desired operation. In some embodiments, the alert can indicate that the IDD 10 is prevented from delivering a dose of medicament (even if priming has already occurred). In such cases, the alert can further include a prompt for the user to deploy the one or more components of the fluid path. That is, if the user has primed the fluid path but is prevented from administering a dose because the one or more components of the fluid path is not deployed, the alert can prompt the user to deploy the one or more components of the fluid path.

It should be appreciated that the process 2800 discussed above is not limited to the order of steps presented in FIG. 28. That is, in some embodiments, the steps of the process 2800 can be performed in a different order than presented in FIG. 28. In some embodiments, one or more of the steps of the process 2800 can be performed substantially simultaneously. For instance, in some embodiments, the determine a threshold pressure value step 2802 can be completed simultaneously with or before receiving data on pressure in the fluid path in the step 2801.

Figure 29B:
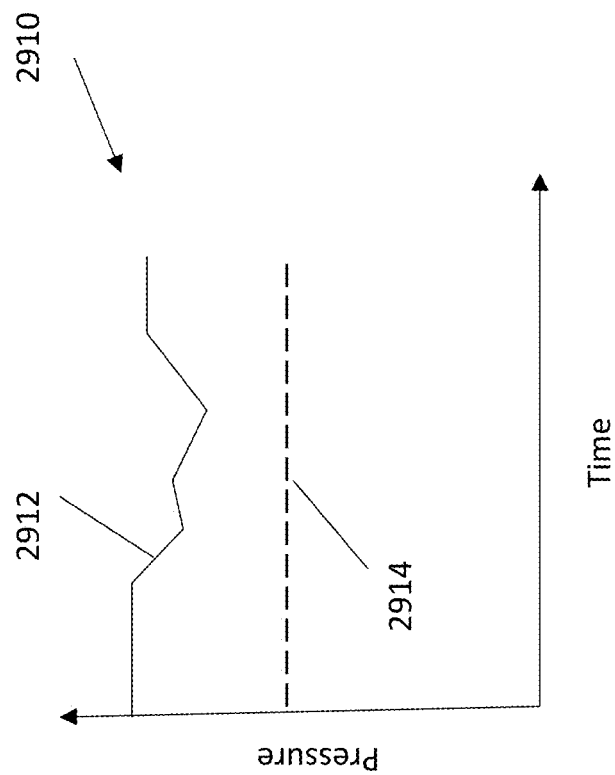
FIG. 29B is a graphical representation of determined pressure in the fluid path of an exemplary IDD of the present disclosure.
Figure 29A:
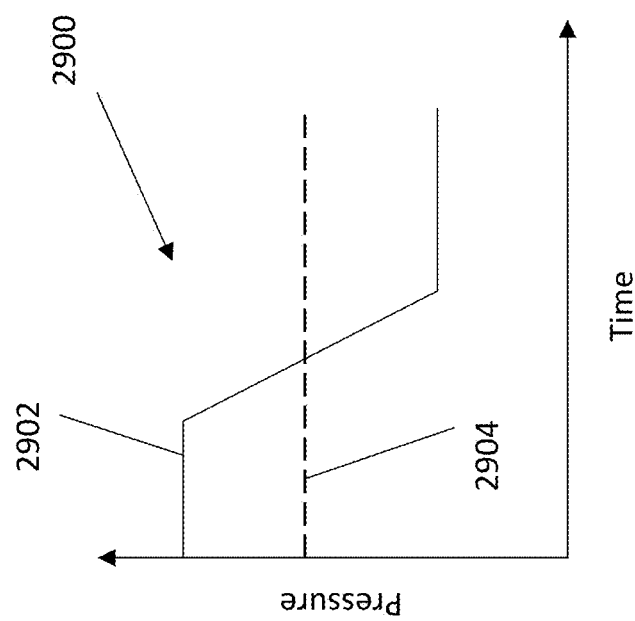
FIG. 29A is a graphical representation of determined pressure in the fluid path of an exemplary IDD of the present disclosure.

FIG. 29A illustrates an example plot 2900 of detected pressure in the fluid path over time. The plot 2900 includes a data set 2902. The data set 2902 may have been collected from an IDD 10 during the operation of the IDD 10. The data set 2902 is shown as exceeding a set threshold pressure value 2904. In the example shown in FIG. 29A, exceeding the pressure threshold value 2904 can include the detected pressure in the fluid path dropping below a lower threshold value.

The IDD 10 can include one or more programming instructions for determining the time at which the detected pressure in the fluid path exceeds or deviates from the one or more threshold pressure values. For instance, in some embodiments, it can be determined whether the detected pressure in the fluid path 900 exceeds (e.g., is greater than) an upper pressure threshold value. For instance, in some embodiments, it can be determined whether the detected pressure in the fluid path 900 exceeds (e.g., is less than) a lower pressure threshold value. For instance, in some embodiments, it can be determined whether the detected pressure in the fluid path 900 extends beyond an acceptable range of pressures (e.g., is greater than an upper pressure threshold or less than a lower pressure threshold). In some embodiments, it can be determined whether the detected pressure in the fluid path 900 exceeds a threshold pressure value for a set or pre-determined amount of time (that is, extends beyond a threshold pressure value and remains beyond a threshold pressure value for a set amount of time). Such analysis can eliminate false positives associated with only determining whether the detected pressure in the fluid path exceeds a pressure threshold value. In some embodiments, it can be determined whether the moving average of the detected pressure in the fluid path (i.e., the average pressure in the fluid path over any consecutive period of a set or predetermined amount of time (e.g., the average over any five second period)) exceeds a threshold average pressure value. Such analysis can eliminate false positives associated with only determining whether the detected pressure in the fluid path exceeds a pressure threshold value. The time at which the detected pressure in the fluid path exceeds or deviates from the one or more threshold pressure values can be stored in or more memory or data storage components. As an example, if it is determined that a particular event associated with the operation of the IDD 10 occurred (e.g., the deployment of the one or more components of the fluid path), the determined event can be timestamped, or associated with the corresponding determined time of occurrence. In a typical course of operation of the IDD 10, the user can be expected to deploy the one or more components of the fluid path immediately after removal of the insertion seal assembly 20 from the IDD 10. Therefore, in embodiments where the threshold pressure value is associated with removal of the insertion seal assembly 20, the occurrence and time of the removal of the insertion seal assembly 20 from the IDD 10 can be directly determined, as discussed above, from analysis of detected pressure in the fluid path. In some embodiments, this determined time can then be assigned to the deployment of the one or more components of the fluid path, which would be expected to immediately follow removal of the insertion seal assembly 20 from the IDD 10. Therefore, in embodiments, occurrence and time of occurrence of deployment of the one or more components of the fluid path can be indirectly determined.

If the above-described determinations on whether the detected pressure in the fluid path exceeds or deviates from the one or more threshold pressure values are made in the negative (e.g., it is determined that the detected pressure in the fluid path does not exceed a threshold value, etc.), it can be determined, based on the particular threshold pressure value in question, that a particular event associated with the operation of the IDD 10 has not occurred. For instance, in some embodiments, if it is determined that the detected pressure in the fluid path does not exceed or deviate from a threshold pressure value that was determined and set as being indicative of the catheter 48 being deployed from the bottom surface of the housing of the IDD 10, then it can be determined that the catheter 48 has not been deployed from the bottom surface of the housing of the IDD 10. Similarly, in some embodiments, if it is determined that the detected pressure in the fluid path does not exceed or deviate from a threshold pressure value that was determined and set as being indicative of the insertion seal assembly 20 being removed from the IDD 10, then it can be determined that the insertion seal assembly 20 has not been removed from the IDD 10. As mentioned above, the determination made on the removal of the insertion seal assembly 20 can be assigned to the deployment of the one or more components of the fluid path. For instance, because deployment of the one or more components of the fluid path would be expected to follow removal of the insertion seal assembly 20 from the IDD 10, if it is determined that the insertion seal assembly 20 has not been removed from the IDD 10, then it can also be determined that the one or more components of the fluid path have not been deployed.

FIG. 29B illustrates an example plot 2910 of detected pressure in the fluid path over time. The plot 2910 includes a data set 2912. The data set 2912 provides an example of data collected from an IDD 10 during the operation of the IDD 10. The data set 2912 is shown as not exceeding a set threshold pressure value 2914. That is, in the example shown in FIG. 29B, the threshold pressure value 2914 can be a lower pressure threshold and exceeding the threshold pressure value 2914 can include the detected pressure in the fluid path dropping below the threshold value. At all times for the plotted data set 2912, it can be determined that the particular event in the operation of the IDD 10 associated with the threshold pressure value 2914 (e.g., removal of the insertion seal assembly or deployment of the one or more components of the fluid path) has not occurred.

If any of the above-described determinations are made in the affirmative (e.g., it is determined that the detected pressure in the fluid path exceeds a threshold value, etc.), it can be determined, based on the particular threshold pressure value in question, that a particular event associated with the operation of the IDD 10 occurred. For instance, in some embodiments, if it is determined that the detected pressure in the fluid path exceeds or deviates from a threshold pressure value that was determined and set as being indicative of the catheter 48 being deployed from the bottom surface of the housing of the IDD 10, then it can be determined that the catheter 48 was deployed from the bottom surface of the housing of the IDD 10. Without being bound by theory, and as discussed above, the available volume in the fluid path can change when the one or more components of the fluid path is deployed. At the same time, the mass of air and liquid in the fluid path may remain unchanged from before deployment to after deployment. Therefore, immediately after deployment of the fluid path, there may be a change in detected pressure in the fluid path. The change in detected pressure in the fluid path can be a drop in pressure in the fluid path. The drop in the pressure in the fluid path can be a transition to a negative pressure. The negative pressure can then equalize over time. The change in pressure in the fluid path can be detected and the resultant pressure can be determined to exceed or deviate from a threshold pressure value.

It should be appreciated that other determinations on the occurrence of a particular event associated with the operation of the IDD 10 can be made depending on the particular threshold pressure value in question. For instance, in some embodiments, if it is determined that the detected pressure in the fluid path exceeds or deviates from a threshold pressure value that was determined and set as being indicative of the insertion seal assembly 20 being removed from the IDD 10, then it can be determined that the insertion seal assembly 20 was removed from the IDD 10. That is, in some embodiments, removal of the seal assembly 20 from the IDD 10 can cause a detectable change in pressure in the fluid path.

While embodiments discussed have focused on detecting and analyzing pressure in the fluid path to determine whether and when the fluid path is deployed or the insertion seal assembly 20 is removed from the IDD 10, it should be appreciated that this is merely a non-limiting example. For instance, the computing devices 112a and 112b, discussed below in more detail, can be similarly configured to receive data from one or more sensors measuring any desirable property of the fluid path, such as a flow of fluid in the fluid path. Deployment of the one or more components of the fluid path and/or removal of the insertion seal assembly 20 can cause a detectable change in the flow property of the fluid path, which in turn can be analyzed to determine the occurrence and time of occurrence of deployment or the one or more components of the fluid path and/or insertional seal assembly 20 removal.

F. Monitor Occlusion after User Attaches Pump and During Use

In reference to step 1006 of FIG. 15, the present disclosure provides systems and methods for detecting an occlusion during use of an IDD 10.

In particular, a medicament delivery path of a pump may become occluded, obstructing the intended flow and leading to reduced or blocked flow. A goal of an occlusion detection system in an infusion pump is to detect these occlusions and generate an alarm to alert the user prior to a significant amount of drug delivery is becoming obstructed. Thus, it is critical for occlusion detection systems to operate with consistent sensitivity within safety limits throughout the life of the infusion device.

Figure 30:
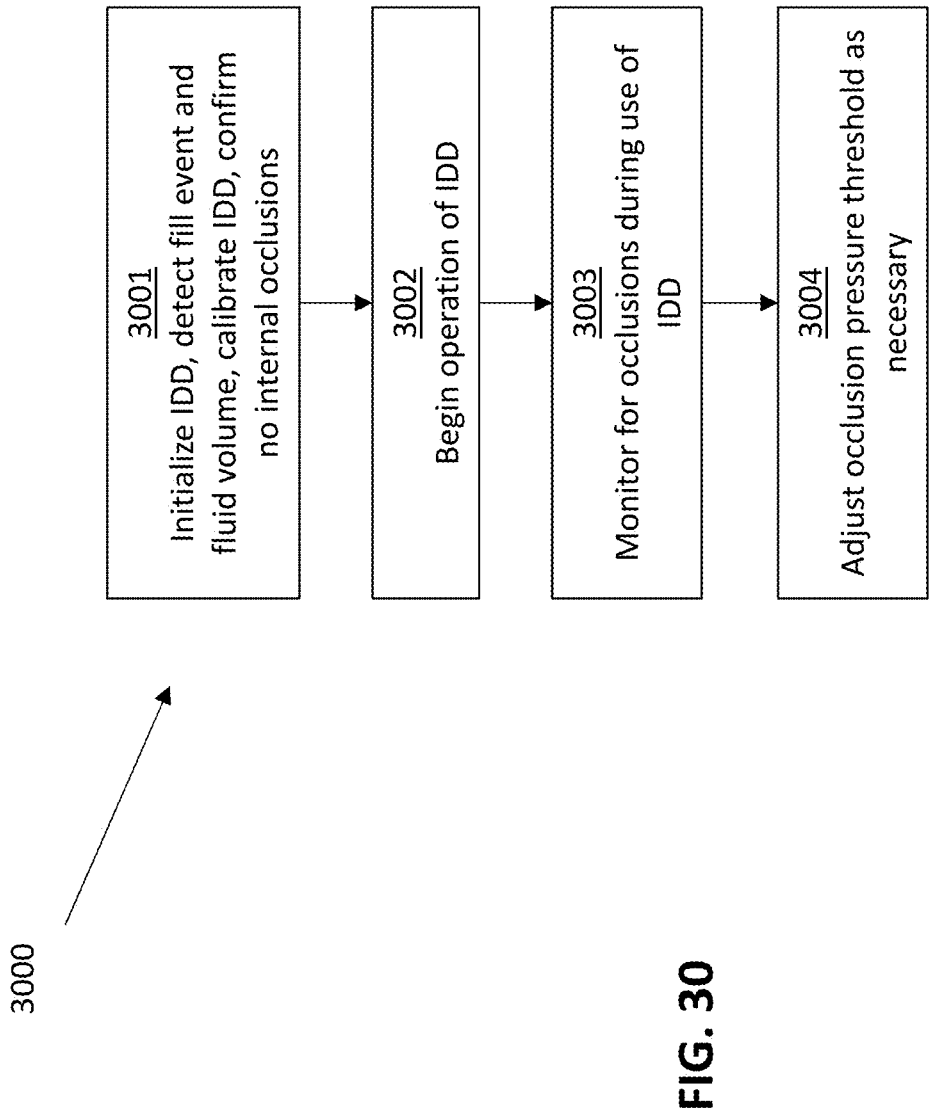
FIG. 30 is a flow chart of an exemplary process for monitoring for occlusions during use of an exemplary IDD of the present disclosure.

FIG. 30 illustrates a flow chart of an exemplary process 3000 for monitoring for occlusions during use of an IDD 10. Step 3001 of process 3000 begins with initializing the IDD, filling of the reservoir with a medicament (e.g., insulin), detecting the fill event, determining a fill volume, calibrating the IDD, confirming no internal occlusions, and priming the IDD. Step 3002 then comprises beginning operation of the IDD. Step 3003 comprises monitoring the IDD for occlusions during operation and determining whether to allow the user to proceed with operation. Step 3004 comprises adjusting an occlusion pressure threshold as necessary based on one or more factors, described in more detail below.

In some embodiments, the MC calibration process, such as process 2400 as described above, may be used to adjust an occlusion detection protocol based on an MC of the IDD 10, as described in detail below. In some embodiments, detecting an occlusion may be based on the relationship between an occluded volume (e.g., the amount of drug blocked from being dispensed), and a pressure generated at the pressure sensor 50 within the fluid path. However, the amount and function of the pressure increase is dependent not only on the volume of blocked flow, but also on the MC of the IDD 10. Thus, the MC may be used to adjust an occlusion detection threshold. Further, while an MC of an IDD 10 may be well understood, there is part-to-part variability, thus it may be desirable to obtain an individual compliance assessment per IDD 10. MC that is unaccounted for in the occlusion detection process may result in delayed detection of an occlusion event. Thus, understanding the MC of the IDD 10 and changes thereto throughout the delivery cycle, e.g., with a change in volume of medicament, a more accurate occlusion detection process can be developed.

Figure 31:
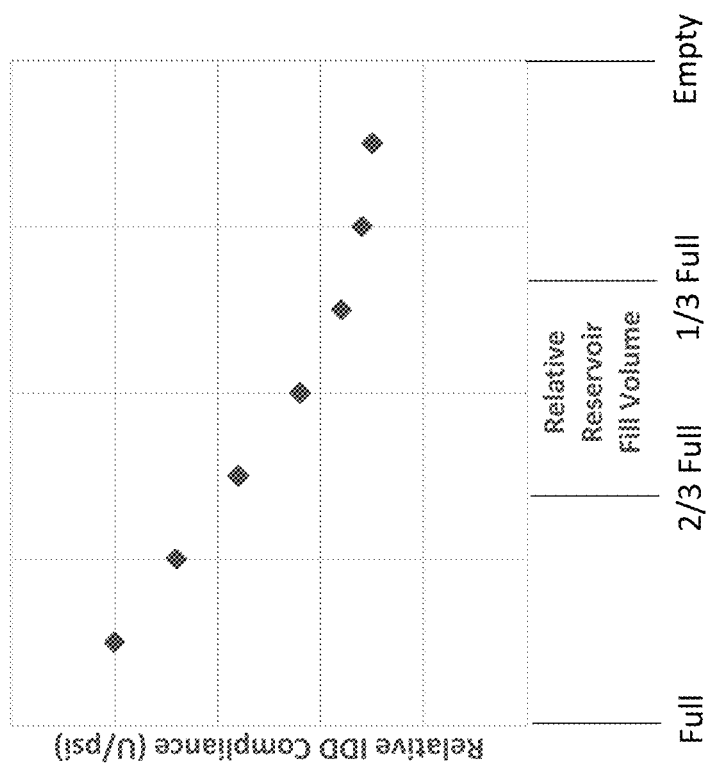
FIG. 31 shows a scatterplot dataset of an exemplary IDD of the present disclosure mechanical compliance (units/psi) vs. reservoir fill volume.

FIG. 31 shows a scatterplot dataset of an IDD mechanical compliance (units/psi) vs. reservoir fill volume. As shown in FIG. 31, the MC (indicated as the relative compliance of the IDD in U/psi, where U is the unit volume of drug in the reservoir 34) may vary based on the amount of fill volume with the reservoir 34 of the IDD 10. Because of the decrease in MC toward the end of the reservoir, as shown in FIG. 31, it may take less change in pressure in the system to go over the pressure threshold and to set off the alarm (e.g., less pressure is required for the sensor 50 to trigger an occlusion). Therefore, the pressure threshold can be dynamic and can increase as the volume of the medicament in the reservoir decreases, such that it would require a higher occluded volume to trigger an alarm.

The occluded volume, or the volume of the occlusion required to generate an alarm is dependent on the pressure threshold curve and mechanical compliance as following: Blocked Volume at Occlusion Alarm=(Compliance)×(Pressure Threshold). In this manner, the pressure threshold curve may be adjusted to optimize performance of the IDD 10 by changing the occlusion detection threshold of the IDD, while ensuring that the patient is administered a sufficient volume of medicament.

Figure 32A:
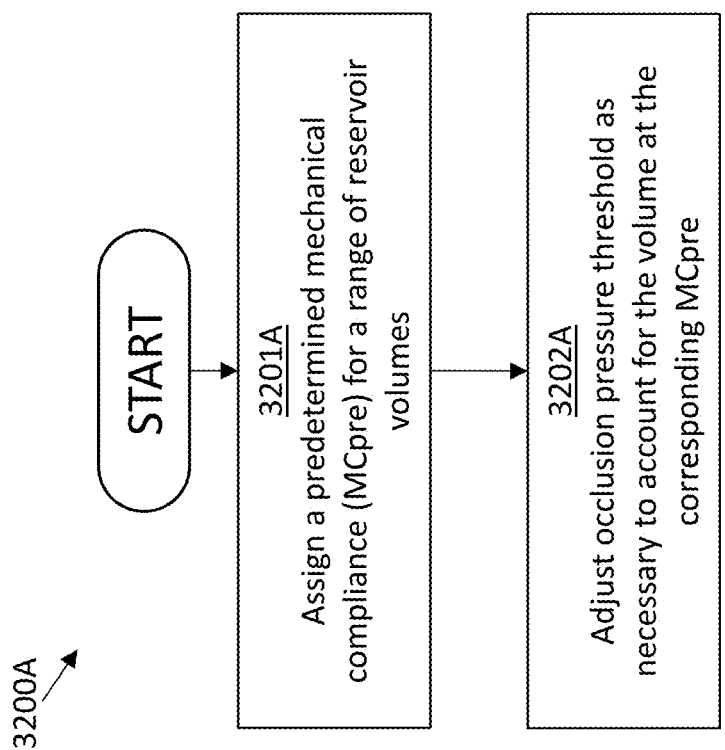
FIGS. 32A-32B illustrate exemplary MC calibration processes, for determining an MC of an exemplary IDD of the present disclosure, used for adjusting an occlusion pressure threshold in detecting an occlusion event.
Figure 32B:
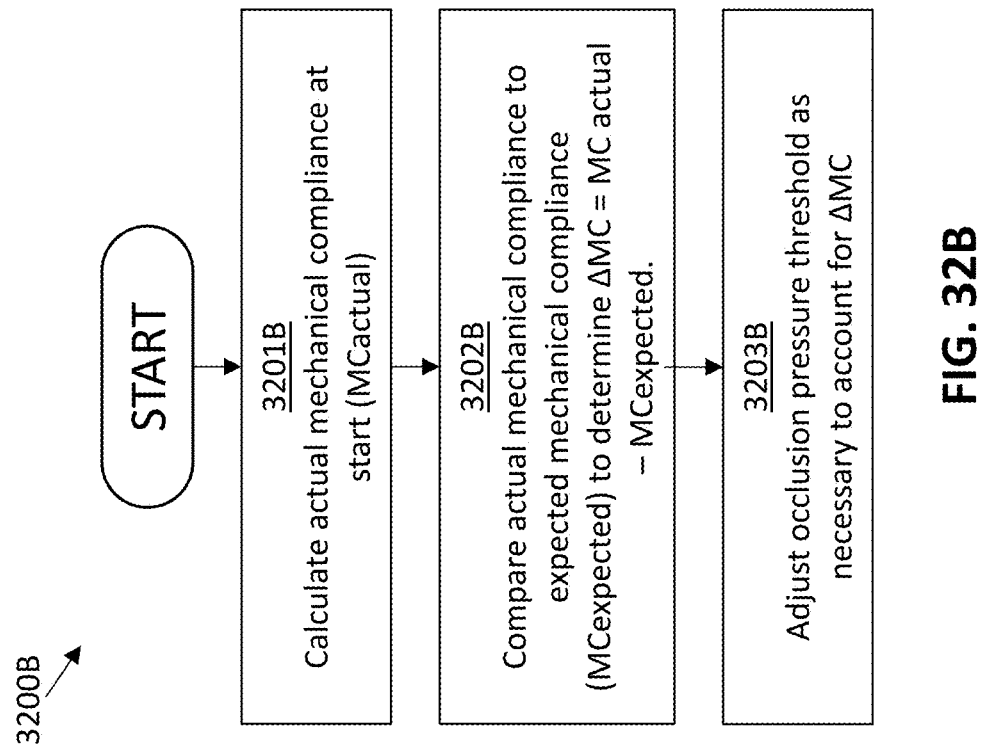

FIGS. 32A-32B illustrate exemplary processes 3200A and 3200B, respectively for using an MC of the IDD 10 to adjust an occlusion threshold. The MC values are used for adjusting an occlusion pressure threshold in detecting an occlusion event.

Process 3200A comprises use of an MC value is that predetermined based on an engineering characterization of IDD compliance. In some embodiments, the engineering characterization is based on one or more tests of a typical IDD. Step 3201A comprises assigning a predetermined mechanical compliance ($MC_{pre}$) for a range of reservoir volumes at the beginning of operation of the IDD 10, using a pressure reading at a corresponding detected volume of medicament in the reservoir 34. Step 3202A comprises adjusting the occlusion pressure threshold, such as shown in FIG. 31, as necessary to account for the for the volume at the corresponding $MC_{pre}$. If the MC calibration process 3200A reveals that the volume does not match the volume at the corresponding $MC_{pre}$, the IDD may then use process 3200A to tune the occlusion detection threshold based on the IDD-specific $MC_{pre}$. The tuned threshold may then minimize false positive occlusion detection if the IDD-specific MC is less than a programmed nominal compliance level.

FIG. 32B illustrates an exemplary process 3200B for using an MC of the IDD 10 to adjust an occlusion threshold. The MC values are used for adjusting an occlusion pressure threshold in detecting an occlusion event. Step 3201B comprises calculating an actual mechanical compliance ($MC_{Actual}$) at the beginning of operation of the IDD 10, using a pressure reading at a corresponding detected volume of medicament in the reservoir 34. Step 3202B comprises calculating a difference in MC values ($\Delta MC$) by comparing the $MC_{Actual}$ to the expected mechanical compliance ($MC_{Expected}$), such that $\Delta MC = MC_{Actual} - MC_{Expected}$. $MC_{Expected}$ may be determined based on the MC values at the corresponding detected volume. Step 3203B comprises adjusting the occlusion pressure threshold, such as shown in FIG. 31, as necessary to account for the $\Delta MC$. If the MC calibration process 3200B reveals that there is a difference between the specific MC and the expected MC, the IDD may then use process 3200B to tune the occlusion detection threshold based on the IDD-specific MC. The tuned threshold may then minimize false positive occlusion detection if the IDD-specific MC is less than a programmed nominal compliance level. This may change the occlusion detection threshold to prevent missed occlusions if the IDD-specific MC is greater than the assumed nominal compliance level.

Figure 33:
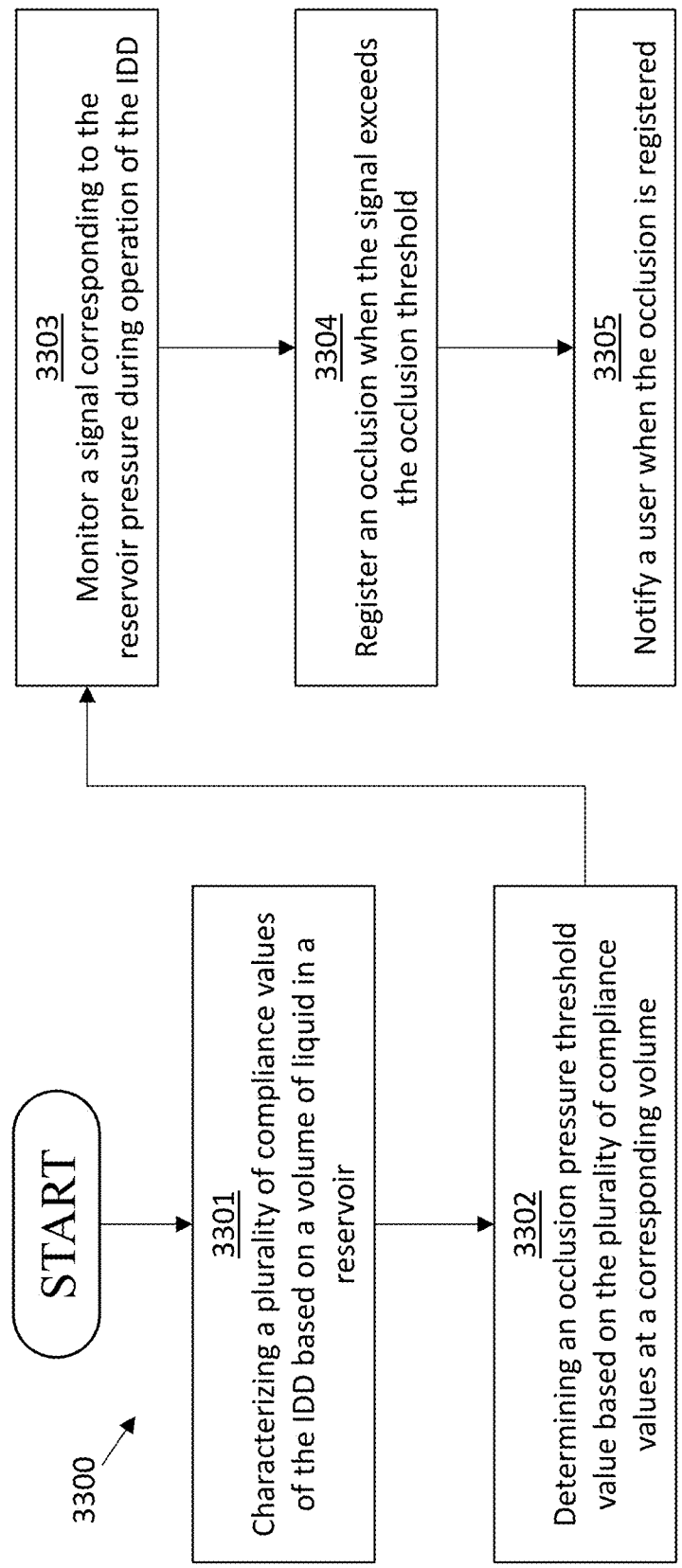
FIG. 33 is an exemplary method for occlusion detection, according to embodiments of this disclosure.

FIG. 33 illustrates an exemplary method 3300 for detecting an occlusion based on a pressure threshold profile as a function of a mechanical compliance (MC) of the IDD 10. In some embodiments, the occlusion pressure threshold curve is generated automatically by computing devices 112a and 112b via method 3300. In some embodiments, the occlusion pressure threshold curve can be manually generated or adjusted by a user, for example, via a user interface.

Step 3301 comprises characterizing a plurality of MC values of the IDD 10 based on a volume of liquid in the reservoir 34 and a measured pressure reading corresponding to a pressure in the reservoir 34 due to occluded liquid (e.g., volume of liquid dosed into the occlusion). The MC of the IDD 10 of the present disclosure may correspond to a sum of mechanical compliances, or total system compliance, for each of a plurality of different components in the IDD 10, such as, for example, a MC of the fluid path, including one or more of the reservoir 34 and the dispense fluid path.

In some embodiments, the MC of the reservoir 34 contributes to about half of the total system compliance when the plunger 54 is all the way at the back of the reservoir 34, e.g., when the reservoir is full of liquid. However, the total system compliance is reduced as the reservoir empties. Pressure threshold values corresponding to occlusions may be characterized based on the volume of blocked flow at different positions in the reservoir 34. In some embodiments, as is explained in more detail below with reference to FIGS. 34 and 35, each of the plurality of MC values may be calculated at discrete volumes of liquid in the reservoir. In some embodiments, the MC values may be calculated based on other factors, for example, medicament delivery rate, in combination with the volume of liquid in reservoir or by themselves.

Step 3302 comprises setting pressure threshold values as a function of the volume of medicament, e.g., insulin, in the reservoir 34 of the IDD 10 for determining an occlusion. A reservoir volume may comprise a corresponding capacity for doses such that a volume of the reservoir may be anticipated based on the number of doses administered. With a static threshold, the pressure may be measured at any particular fluidic volume, then used as the threshold consistently such that any pressure exceeding that threshold, no matter the volume in the device, would set off an alert, such as an alarm via the wireless controller and/or IDD or a message on the user interface of the wireless controller, that an occlusion has occurred. In some embodiments, a dynamic threshold accounts for changes in the MC of the IDD 10, such that the threshold may change based on the volume of the liquid in the reservoir 34. In some embodiments, the pressure threshold values are obtained through measurements by a pressure sensor 50 in the reservoir 34 or fluid path. Based on the information obtained for the MC of an IDD, dynamic pressure threshold values may be set for the IDD 10. In an embodiment, the pressure threshold values are defined by an equation and a corresponding curve. In some embodiments, a dynamic pressure threshold curve is set for the IDD 10 when the reservoir 34 is filled at three specific points: full, half full, and empty. In some embodiments, the dynamic threshold may be set for the IDD 10 when the reservoir is filled at five specific points: ¾ full, ½ full, ½ full, ¼ full and empty. In some embodiments, the threshold may be set based on other parameters, for example, delivery rate, in combination with the reservoir volume or by itself.

Referring back to FIG. 33, in step 3303, the IDD 10 may monitor a signal corresponding to one or more of a reservoir pressure or a dispense fluid path pressure in the IDD as the liquid is administering and comparing the signal to the pressure threshold curve. The signal may be obtained during use of the IDD 10, for comparison to the pressure threshold curve obtained from characterization of the MC of the IDD 10. In some embodiments, the signal is produced by a pressure sensor 50. In some embodiments, the signal from the pressure sensor may be supplemented by one or more signals from each of a motor current sensor, a force sensor, or a combination thereof.

In step 3304, the IDD 10 may register an occlusion when the signal exceeds the pressure threshold curve at that point, which may be based on the pressure threshold curve of the reservoir. Finally, in step 3305, the IDD 10 may notify a user when the occlusion is registered. In some embodiments, the alarm may be visual, such as through an LED or other light indicator, or audible, such as through a noise alarm.

Whether a device uses a pressure sensor or not, the infusion device typically utilizes a signal that correlates strongly to pressure in the reservoir, because pressure rises during an occlusion event with controlled infusion. For example, other systems may use a force sensor and/or encoders to detect a stall when the device is not strong enough to push against certain back-pressures. Such configurations are compatible with the IDD 10 as well. Further, other systems are not configured to detect occlusions for fully detached, free-floating plungers. Thus, the embodiments described herein are compatible with such detached, free-floating plungers.

FIGS. 34A-34D are graphical exemplary representations curve fittings of pressure thresholds that may be used in the IDD 10 in accordance with embodiments of this disclosure. In some embodiments, a static pressure threshold curve is used. In some embodiments, such static threshold may be used where the reservoir liquid volume is depleted (e.g., when more doses of drug are delivered), as it may be desirable to have higher sensitivity to small occlusions, which may result in more frequent alarms. The IDD 10 may keep track of the plunger 54 position in the reservoir 34 with each dose and determine the pressure threshold curve of each dose by interpolating (e.g., linear, polynomial, and spline) between the pre-defined points. In some embodiments, the static threshold may result in less sensitivity to occlusions and delayed occlusion alarms when the reservoir is full, but can still ensure that the patient receives a sufficient injection.

In some embodiments, a dynamic pressure threshold curve (as illustrated in FIGS. 34B-34D) may be used to detect occlusions, so that occlusions are detected at lower pressures in a full reservoir, and higher pressures in an emptier reservoir. Dynamic pressure threshold curves may change a sensitivity to the occlusion pressure. For example, using a dynamic threshold may increase the minimum volume required to set off an occlusion alarm by decreasing sensitivity to the occlusion pressure, while staying within IDD safety limits. In other words, a dynamic pressure threshold curve may maintain consistent sensitivity of the occlusion detection method over the full device lifetime. Functionally, this may reduce a number of false-positive occlusion alarms, while detecting occlusions without adding delay to occlusion alarms that would impact user safety.

In some embodiments, the occlusion pressure threshold curve may be optimized further based on a desired sensitivity of the pump at different stages of the delivery cycle. Generally, occlusion pressure threshold curves may be determined based on the volume of liquid within the reservoir 34, comprising setting an $n^h$ occlusion pressure threshold value ($OT_n$) corresponding to volume of medicament within the reservoir 34 ($VI_n$), then fitting a curve to each pressure threshold value at the corresponding VI value. By changing the pressure threshold for determining an occlusion, the sensitivity of the pump may be changed corresponding to the individual needs of the patient and compliance values of the individual IDD 10.

In some embodiments of an occlusion method of the present disclosure, when the MC is high, e.g., when the reservoir 34 is full, pressurization occurs slowly for a given occluded volume, so the occlusion detection method would require a low threshold to increase the sensitivity of the method; and when MC is low (e.g., when the reservoir 34 is empty), pressurization occurs rapidly for a given occluded volume, so the occlusion detection method would require a high threshold to decrease the sensitivity of the method. Depending on the type of IDD, there may be reasons to lower the pressure threshold as the reservoir 34 empties as illustrated in FIG. 34C. For example, if there is a delivery method where it is known that occlusions typically clear themselves when the reservoir 34 is full, but occlusions tend to be more severe when the reservoir 34 is almost empty, it may be beneficial to raise the pressure threshold when the reservoir 34 is full to allow the occlusions more opportunity to clear themselves, but detect occlusions more quickly at the end of the reservoir 34. In FIG. 34D, occlusions may be detected with a smaller trigger pressure as the reservoir 34 empties. In some embodiments, if it is determined that there is no change, or a change in the MC of the IDD 10 is negligible, the IDD 10 may determine that a static pressure threshold curve, as illustrated in FIG. 28A, is more appropriate than a dynamic pressure threshold curve.

In some embodiments, the IDD 10 may set a pressure threshold curve based on the plurality of compliance values and the volume. Thus, with each dose corresponding to the volume, a new threshold may be calculated. In some embodiments, the calculating comprises using linear interpolation at the volume between two of the plurality of pressure thresholds. For example, if the $400^{th}$ dose is being administered, the IDD 10 may interpolate between a pressure threshold of 20 psi at a $50^{th}$ dose (e.g., (50, 20)) and a pressure threshold of 15 psi at a $3,000^{th}$ dose (e.g., (3000, 15)) to calculate a pressure threshold of 21 psi at a $400^{th}$ dose (e.g., (400, 21)). In some embodiments, the interpolation is between two subsequent pressure thresholds of the plurality of pressure thresholds. In some embodiments, the calculating comprises using a predetermined equation between each of the plurality of pressure thresholds. In some embodiments, the calculating comprises using a lookup table. In some embodiments, the calculating comprises using a method with additional inputs (e.g., matrices, parametric equations).

Figure 35A:
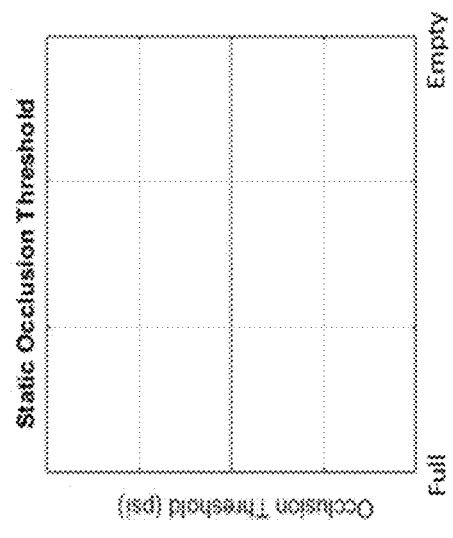
FIGS. 35A and 35B show examples of a static pressure threshold and the resulting sensitivity of an exemplary IDD of the present disclosure.
Figure 35B:
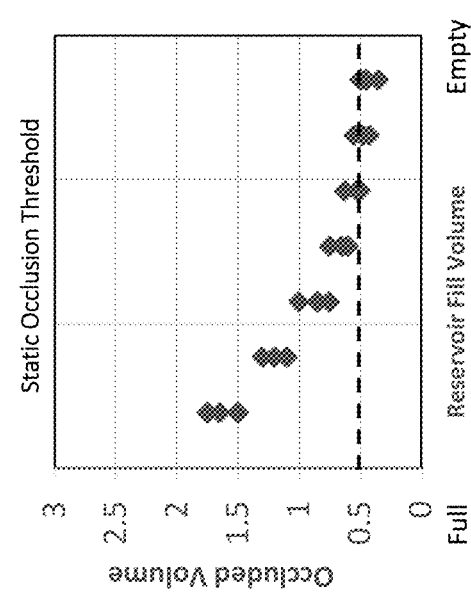

FIGS. 35A-35B provide a comparison of occlusion pressure threshold curves on the resulting occlusion alarms, specifically the blocked volume (e.g., occluded volume), required to set off the occlusion alarm. The occluded volume value alarm may be desired so that the patient is aware of the volume of liquid (e.g., insulin), that they are not receiving from the IDD 10 due to occlusion.

The occluded volume is dependent on the pressure threshold curve and mechanical compliance as following: Volume at Occlusion to Generate an Alarm=(Compliance)×(Pressure Threshold). In this manner, the pressure threshold curve may be adjusted to optimize performance of the IDD 10 (e.g., change sensitivity of the IDD), while ensuring that the patient is administered a sufficient volume of medicament.

FIG. 35A illustrates a static occlusion pressure threshold curve set. FIG. 35B provides a graphical output of an occluded volume required to set off the occlusion alarm based on the static occlusion pressure threshold curve. When the reservoir pressure measured spikes and exceeds the pressure threshold value, the IDD 10 is triggered to process the occurrence of an occlusion.

Figure 36A:
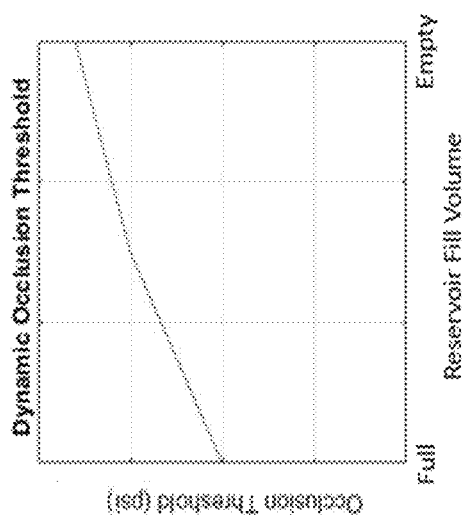
FIGS. 36A and 36B show examples of a dynamic pressure threshold and the resulting sensitivity of an exemplary IDD of the present disclosure.
Figure 36B:
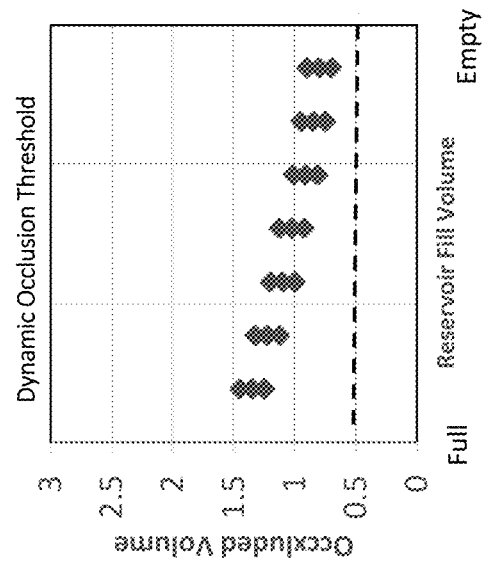

FIG. 36A illustrates a dynamic pressure threshold curve according to one aspect of the present disclosure, with the threshold varying based on the number of increments dosed that correspond to a liquid volume in the reservoir 34. In some embodiments, an occlusion method of the present disclosure may specify a $T_1$ psi threshold when the reservoir 34 is full (0 increments dosed so far), a $T_2$ psi threshold when the reservoir 34 is half full, and a $T_3$ psi when the reservoir 34 is empty. The three pre-defined points defined in the method (corresponding to increments dosed and associated pressure threshold) are (0, $T_1$), (½, $T_2$), (1, $T_3$). Because the IDD 10 of the present disclosure has a reservoir 34 with a known volume of medicament and known dispense stroke volume to count down doses and estimate how much medicament is expelled from the reservoir 34, with each new dose, the IDD 10 is keeping track of the relationship between reservoir 34 full volume and how many doses have been administered from the IDD 10, and thus a new occlusion pressure threshold can be calculated using the method. Using the above example, if the dose is being administered, the IDD 10 linearly interpolates between (0, $T_1$) and (½, $T_2$) to find the pressure threshold at any point during the delivery. FIG. 36B provides a graphical output of an occluded volume required to set off the occlusion alarm based on the dynamic occlusion pressure threshold curve of FIG. 36A.

Figure 37:
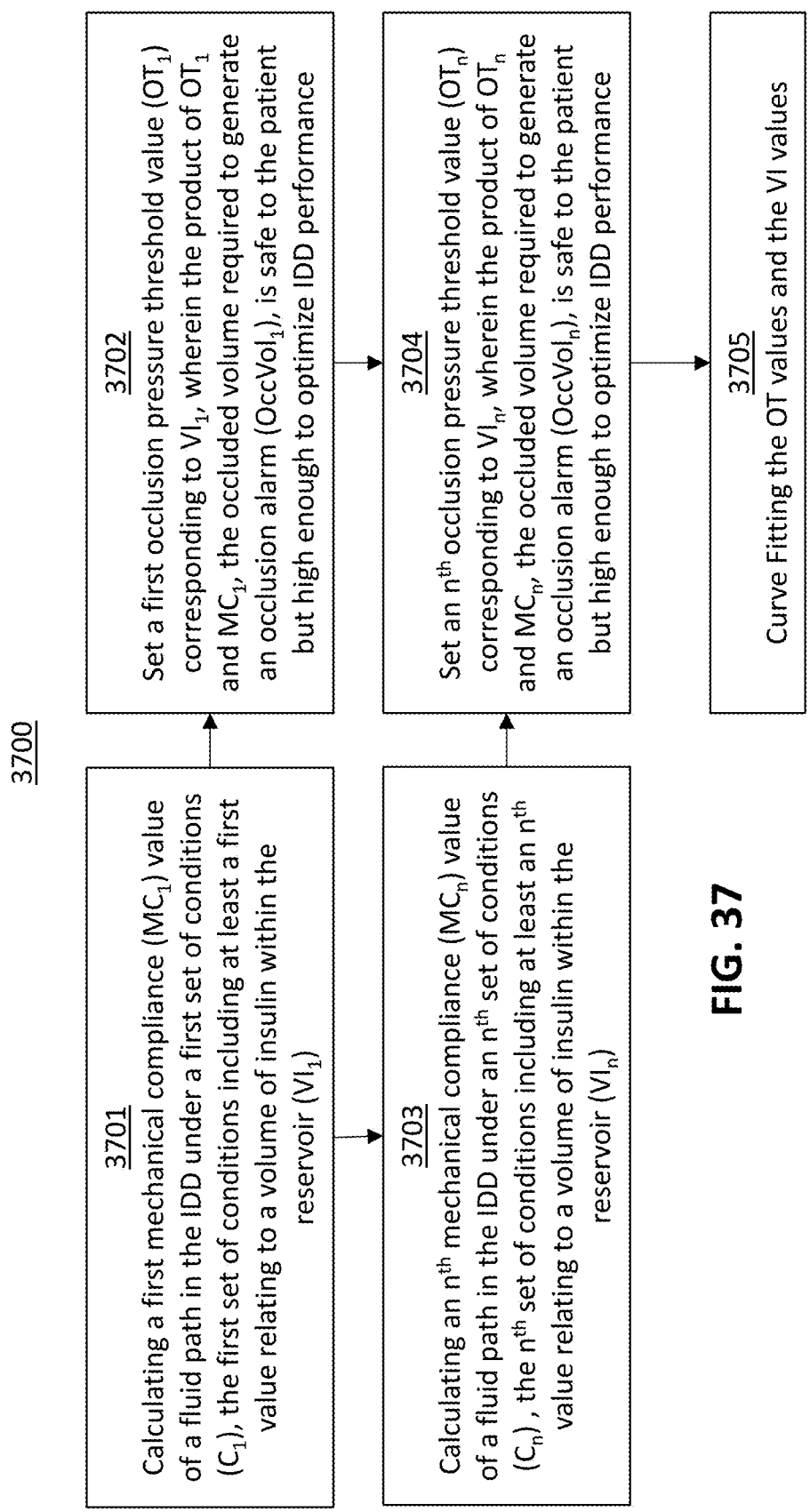
FIG. 37 is an exemplary method for occlusion detection for an IDD of the present disclosure.

FIG. 37 provides an exemplary method 3700 with steps for setting the dynamic pressure threshold for the present disclosure. In steps 3701 and 3703 $n$ mechanical compliance ($MC_n$) values of a fluid path in the IDD 10 system under n sets of conditions ($C_n$) is calculated, for example, as described above. In some embodiments, each set of conditions may include a value relating to the volume of medicament within the reservoir 34 ($VI_n$). Other conditions, for example, flow rate, impacting MC can also be used in addition or instead of the reservoir volume.

In steps 3702 and 3704, pressure threshold values corresponding to different volumes can be set, such that the occluded volume required to generate an occlusion alarm is safe to the patient but high enough to optimize IDD performance. In steps 3702 and 3704, the pressure threshold curve may be set considering a combination of sensitivity of the device within safety limits and a number of alarms set for achieving a desired safety. For example, using a static pressure curve, with reference to FIG. 35A, the pressure may be measured at any volume, then used as the threshold consistently such that any pressure exceeding that threshold, no matter the volume in the device, would set off an alert that an occlusion has occurred. As another example, with reference to FIG. 35A, a dynamic threshold curve may be set to account for changes in the MC of the IDD 10, such that the threshold may change based on the volume of the liquid in the reservoir 34. This dynamic threshold accounts for changes in pressure in the IDD 10, and therefore the occlusion. By adjusting the dynamic threshold, optimal safe operating points can be established to detect occlusions timely without creating unnecessary annoyance to the user. While the sensitivity to occlusions may be changed with the pressure threshold, the occluded volume will remain within a predetermined safety limit. In other embodiments of this design, the pressure threshold curve may be set to patients' individual needs. In step 3705, a pressure threshold curve is generated as a function of the reservoir volume.

G. Detecting an End of a Reservoir

In reference to step 1007 of FIG. 15, the present disclosure provides systems and methods for detecting when a reservoir is empty.

In some embodiments, the IDD 10 may be configured to safely deliver a medicament to a user while minimizing the amount of medicament leftover in the fluid path at the end of the IDD 10 lifetime. In particular, a volume of medicament delivered from the reservoir 34 may be maximized by advancing the plunger 54 through the reservoir 34 as far as possible, while maintaining dose accuracy, i.e., a relative change between an actual dose received by the user as compared to an expected dose. In some embodiments, an expected dose is how much medicament is expected to be received as the plunger advances a set distance or increment, which can be based on engineering assessments of the IDD 10. The systems and methods described herein are designed to minimize dose error and ensure dose accuracy to avoid inaccurate dosing after the plunger 54 has reached the end of the reservoir 34, since doses may not be accurately delivered at this point.

Figure 38:
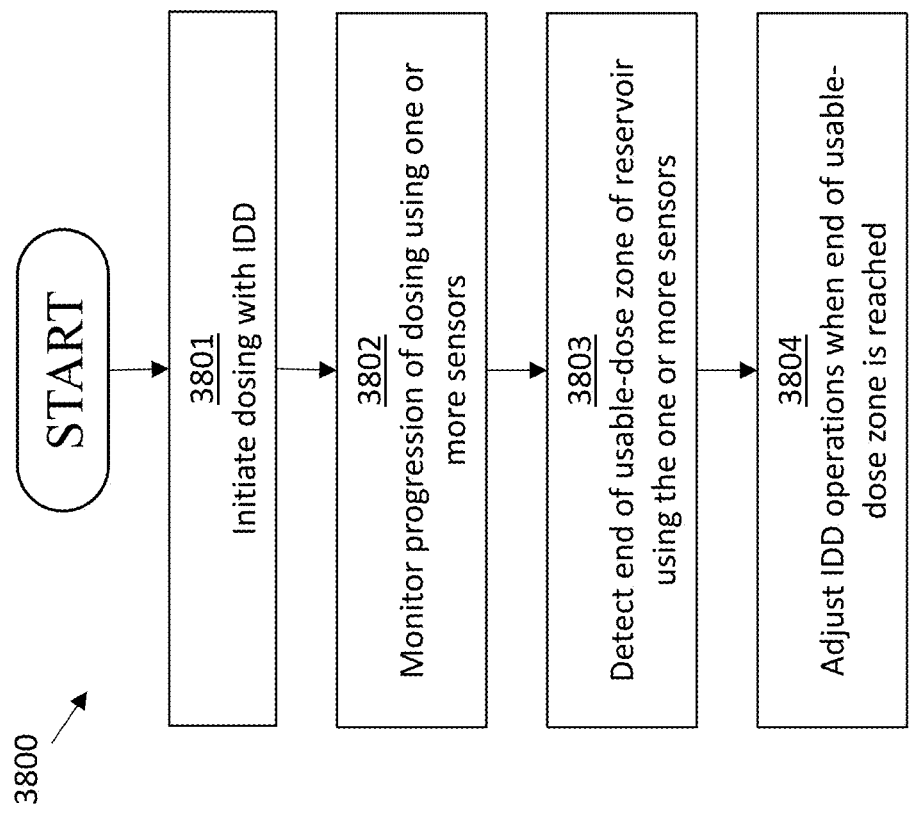
FIG. 38 presents an exemplary method for adjusting operating parameters based on a usable-dose zone of an exemplary IDD of the present disclosure.

FIG. 38 illustrates a flow chart of an exemplary process 3800 for adjusting operating parameters based on a usable-dose zone of an IDD 10. As discussed above, the IDD 10 comprises at least reservoir 34, plunger 54, a screw train drive assembly 42 for moving the plunger 54 within the reservoir 34 to release a medicament within the reservoir 34 towards the dispense fluid path, and at least one pressure sensor 50 positioned to interface with the reservoir 34 or fluid path. Before initiating the exemplary method 3800, the IDD 10 may be filled with a volume of medicament in the reservoir 34. In step 3801, dosing with the IDD 10 is initiated by moving the plunger 54 as dosing increments are administered. The number of doses administered may be monitored as they are delivered. In step 3802, the IDD 10 may monitor a progression of the plunger 54, where the monitoring may be based on information received from the pressure sensor 50 for detecting one or more infusion signals corresponding to each dose administered. In step 3803, the IDD 10 may detect the end of the usable-dose zone using the pressure sensor 50. In some embodiments, the detecting may be based on the one or more infusion signals exceeding a threshold. The end of the usable-dose zone may be used to determine a travel distance of the plunger 54 from the recorded position at the starting condition, thereby triggering further response of the IDD 10. In some embodiments, the end of the usable-dose zone may further be based on the received information regarding the usable-dose zone of the IDD 10. In step 3804, the operations conditions of the IDD 10 may be adjusted depending on a user-programmed preference for responding to the end of the usable-dose zone. For example, the IDD 10 may prevent a user from administering further doses or notify the user that the IDD 10 is at or near the end of the usable-dose zone. Further, the IDD 10 may adjust dosage parameters to compensate for a change in the one or more infusion signals to allow further dosing.

In some embodiments, the usable-dose zone of the IDD 10 may be estimated based on one or more infusion signals detected simultaneously to the number of doses delivered, such as, for example, a delta pressure, an average motor current, a motor on-time signal, and an energy for each dose signal. Such infusion signals may be indicative as to whether the plunger 54 has struck or is nearing the end of the reservoir 34 of the IDD 10, allowing a user to be more confident as to whether additional volume of medicament is available for dosing.

In some embodiments, the methods and systems for detecting an empty reservoir may improve the safety of the IDD 10. If the user believes they are delivering a certain amount of medicament when they are outside of the usable-dose zone, the user may not actually be delivering medicament. For example, inaccurate dosage delivery can result in under-infusion if the user believes that the IDD 10 is delivering a medicament, but instead the IDD 10 is delivering a different amount of medicament. In some embodiments, the IDD 10 could tell the user that the plunger 54 is approaching the end of the usable-dose zone where the accuracy of the dosage may be impaired, or could be used to deactivate the IDD 10 if being at the end of the usable-dose zone poses a danger. A significant amount of error in dosage could pose a threat to user safety since the infusion could deliver a different actual volume instead of an expected volume of medicament.

In some embodiments, methods for empty reservoir detection, as disclosed herein, relate generally to usable-dose zone determination processes for use in IDDs such as wearable medicament infusion patches. As discussed below, such methods may be used to determine, using infusion signals, an end of a usable-dose zone during operation of an IDD 10 relative to an initial fill detection of the reservoir in an IDD 10, from which the IDD 10 may prevent further use or adjust dosing parameters to compensate for inaccurate dosing.

Figure 39:
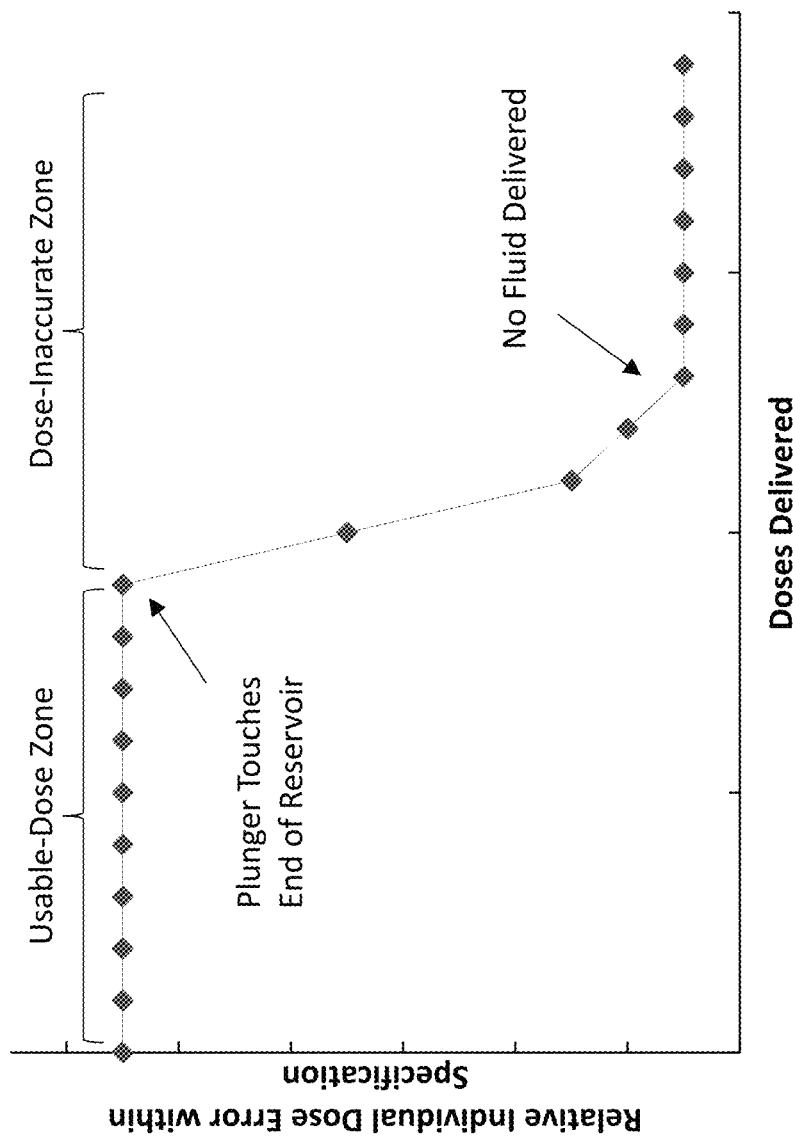
FIG. 39 illustrates an exemplary operating plot showing a dose error (%) generated from an individual IDD as doses are delivered.

FIG. 39 illustrates an exemplary operating plot showing a dose error (%) generated from an individual IDD as doses are delivered. In reference to FIG. 39, as the plunger 54 nears the closed end 34a of the reservoir, a dose error (%) may increase such that the actual dose may be significantly different than the expected dose. As further shown in FIG. 39, the dose error is expected to remain relatively consistent within a usable-dose zone of the reservoir 34. As more doses are delivered, eventually the fluid diminishes and the plunger 54 contacts the closed end 34a of the reservoir 34, as indicated by the relatively high change in dose error. The recorded dose delivered at this point marks the beginning of the dose-inaccurate zone. The dose error nearing 100% indicates that medicament is no longer being administered as doses are delivered. In some embodiments, once the dose-inaccurate zone is determined, a user may proceed to use the IDD 10 according to exemplary method 3800 in FIG. 38, exemplary process 4100 as described in more detail below with respect to FIG. 41A, or exemplary process 4200 as described in more detail below with respect to FIG. 42.

The methods and systems of the present disclosure are designed to ensure that the IDD 10 can deliver the greatest volume available while still reliably delivering fluid accurately for the entire duration of the infusion. In general, each IDD 10 has a minimum usable volume (e.g., a usable-dose zone), in which doses of medicament will have an actual volume (AV) as characterized during engineering dose accuracy assessments, described in more detail below, (i.e., a volume of medicament in the dose), that is the same or close to a claimed dispense volume or expected volume (EV), (i.e., an expected volume of medicament in each dose as, for example, determined by engineering tests), within error tolerance. A user can access more or less than that volume depending upon how much they fill the device with and the ultimate tolerances of the individual IDD 10. However, as the plunger nears the closed end 34a of the reservoir, it enters a dose-inaccurate zone, in which the dose error increases such that the AV of the doses may be significantly different than the EV.

In some embodiments, determining the dose error (%) of the IDD may include monitoring an AV delivered. As each dose is administered, the monitored AV is recorded along with infusion signals. It has been observed that several signals correlate directly to the dose accuracy of each dose. As doses are administered, the IDD 10 may dose past a range of doses administered where the doses are no longer accurate, (e.g., when the EV to be dispensed does not match the monitored AV), thus generating a range of inaccurate doses. The identifying may be based on a calculated error between the EV and the AV, such that the error exceeds a threshold. In some embodiments, the thresholds may be chosen to correspond to a point before the dose accuracy reaches a level that would be unacceptable to the safety of the user. The dose error may be calculated as follows:

$$\text{Dose Error} = 100 \times (AV - EV)/EV$$

Figure 40:
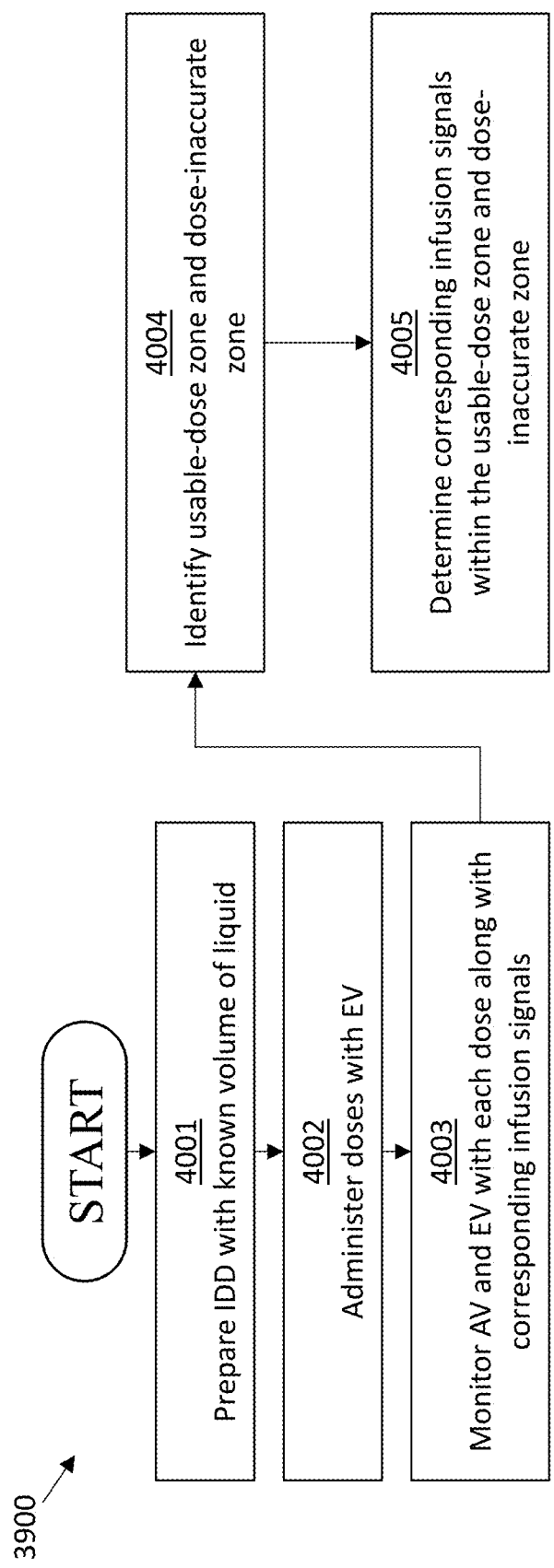
FIG. 40 illustrates an exemplary process for determining a usable-dose zone and a dose-inaccurate zone.

FIG. 40 illustrates steps in an exemplary process 3900 of the IDD 10 for performing an engineering assessment to determine the usable-dose zone and dose-inaccurate zone and associated infusion signals, such as, for example, a pressure delta and a motor current. In some embodiments, the engineering assessment is performed during development of the IDD 10. During the engineering assessment, the AV delivered may be determined using a mass-based dose accuracy test or a similar method. As the dosing occurs, the dose accuracy may be characterized through the calculation of a dose error (%) for each increment, which may be measured by comparing the mass of the dose delivered (i.e., an AV) to the mass of the dose requested (i.e., an EV), during dose-accuracy testing.

Step 4001 comprises preparing an IDD 10 with a known volume of medicament, such as, for example, insulin. Step 4002 comprises administering doses from the IDD 10 having a pre-determined EV. Step 4003 comprises monitoring the AV of each dose corresponding to an EV of each dose. In some embodiments, one or more infusion signals are simultaneously measured with each dose. Step 4004 comprises identifying, based on the monitoring from Step 4003, the usable-dose zone and the dose-inaccurate zone. For example, where the plunger may be at the closed end 34a of the reservoir 34 such as the dosage may be inaccurate, thereby identifying the usable-dose zone and dose-inaccurate zone. Step 4005 comprises determining signals of the one or more infusion signals that correspond to each of the usable-dose zone and dose-inaccurate zone. This information may be utilized to notify a user of the dose-accuracy, which may indicate that the dosing has approached the closed end 34a of the reservoir 34 and the dosage may be inaccurate. In some embodiments, the corresponding infusion signals allow for generating potential thresholds by which such signals may be used to identify the range of inaccurate doses.

Figure 41A:
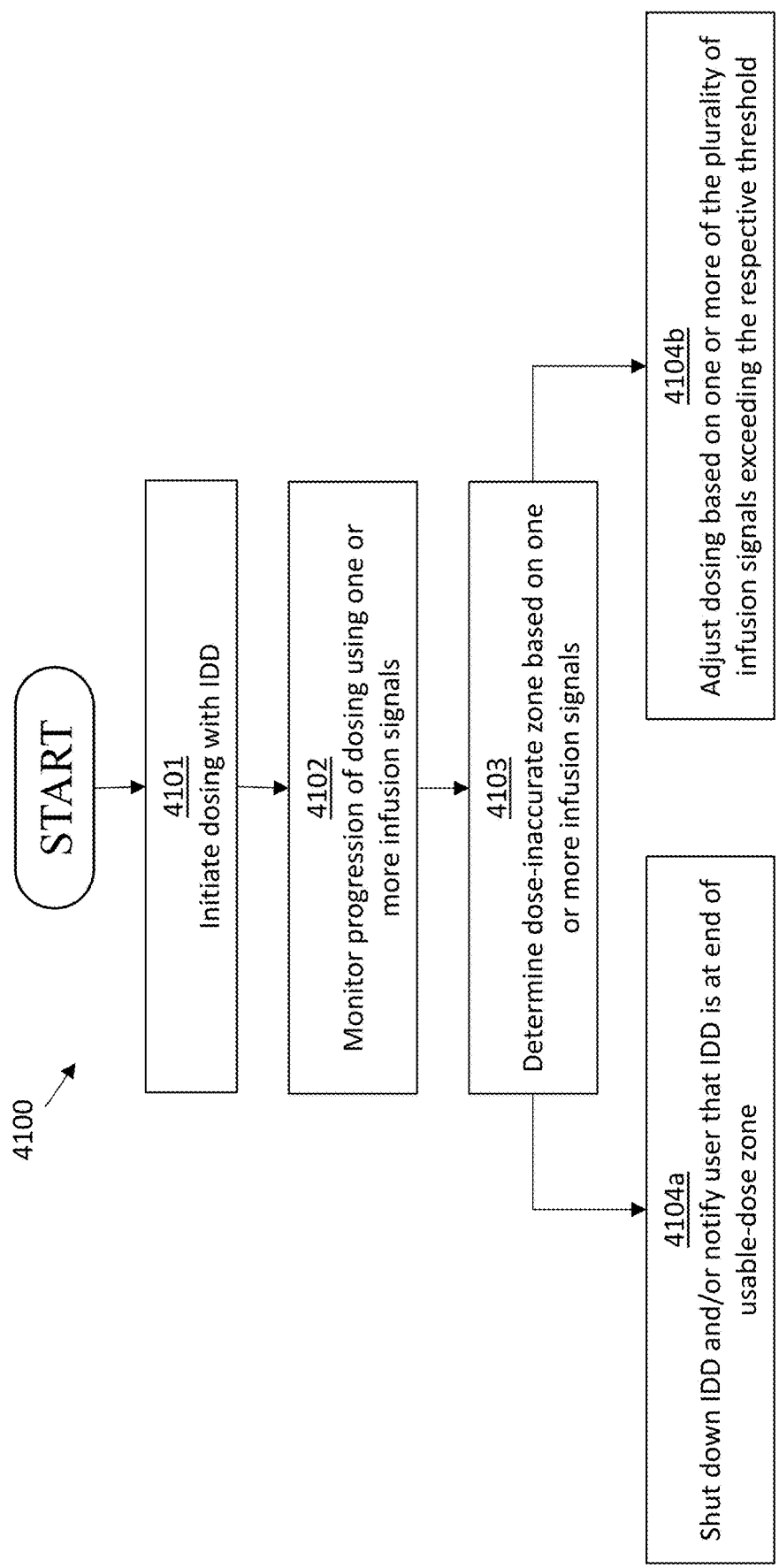
FIG. 41A illustrates an embodiment of a method for operating an exemplary IDD of the present disclosure based on a usable-dose zone information.
Figure 41B:
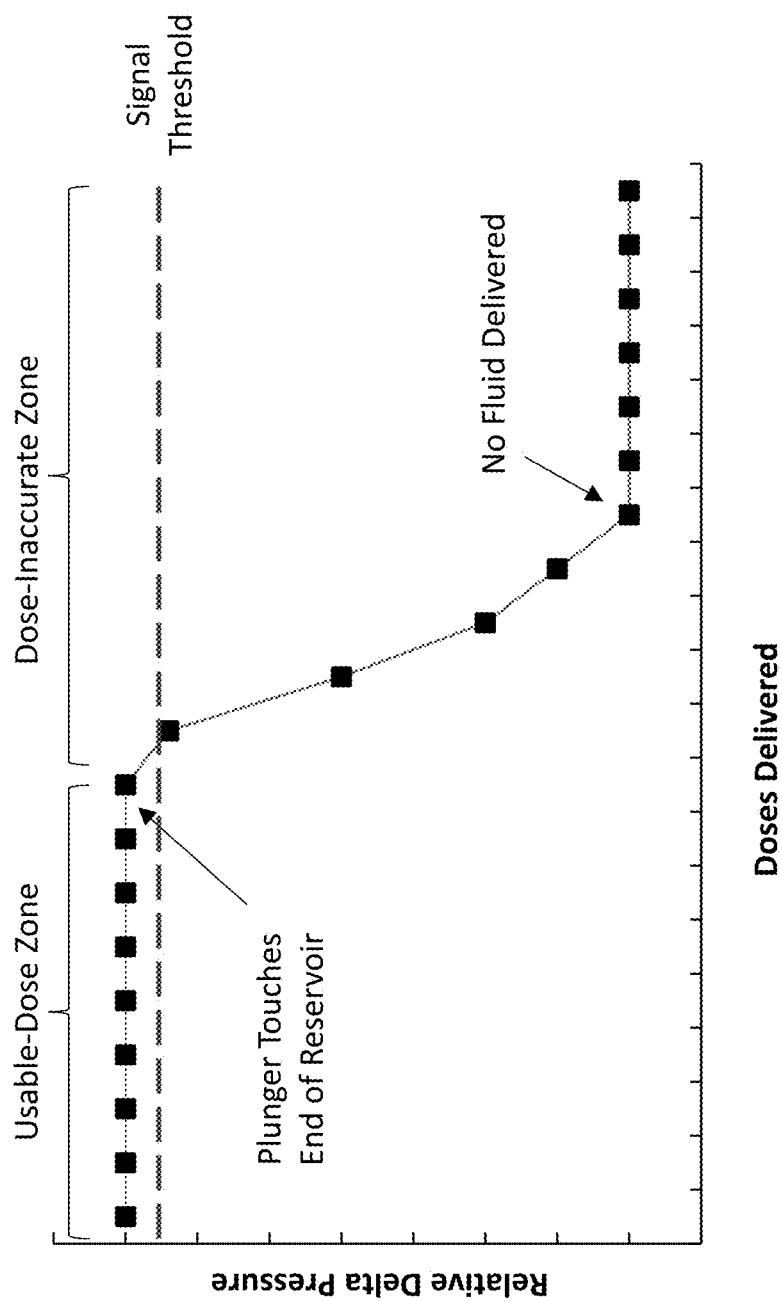
FIGS. 41B and 41C show exemplary operating plots showing infusion signals generated from an individual exemplary IDD of the present disclosure as doses are delivered.
Figure 41C:
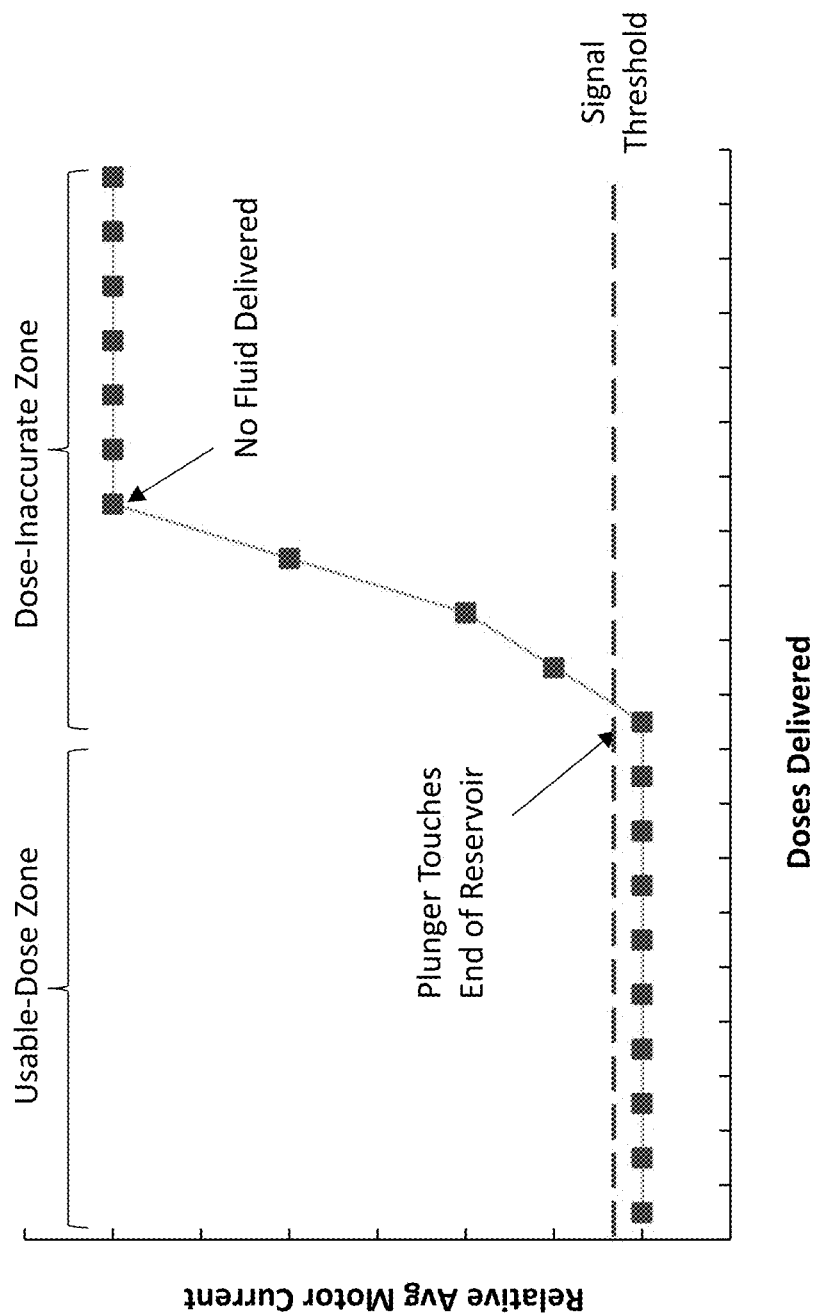

FIG. 41A illustrates an exemplary process 4000 for operating an exemplary IDD of the present disclosure based on a combination of engineering dose accuracy characterizations and a plurality of infusion signals, such as, for example, a delta pressure and a motor current. FIGS. 41B-41C illustrate exemplary operating plots showing infusion signals generated from an individual IDD 10 as doses are delivered, such as a delta pressure (psi) (FIG. 41B) and an average motor current (mA) (FIG. 41C), respectively.

In some embodiments, the IDD 10 has several integrated sensors which can read infusion signals while doses are administered for determining if the plunger 54 has struck or contacted the closed end 34a of the reservoir 34. Determining such contact allows the user to deliver the full available contents of the fluid path and not waste medicament. In this approach, the IDD 10, using the integrated sensors, may monitor multiple signals during the infusion to detect when the plunger 54 has reached the closed end 34a of the reservoir 34, at which point no further insulin can be delivered reliably. Then, the IDD 10 may stop any further infusion. This approach further allows the IDD 10 to proceed with infusion even after an estimated volume has been delivered. Rather than solely using empirical testing, monitoring signals to detect the closed end 34a of the reservoir 34 allows the IDD 10 to maximize delivered volume, even when there is pump-to-pump variability in the volume of medicament available.

In reference to FIG. 41A, step 4101 comprises initiating dosing with the IDD 10. The dosing may be performed automatically through a program or manually by the user. Dosing with the IDD 10 may be initiated by moving the plunger as dosing increments are administered. In step 4102, the IDD 10 may monitor a progression of the plunger, where the monitoring may be based on information received from at least one sensor for detecting the one or more infusion signals. In some embodiments, the infusion signals may correspond to each dose administered. In step 4103, the IDD 10 may detect when the end of the usable-dose zone, and thus the beginning of the dose-inaccurate zone, is approaching. The detecting may be achieved using the at least one sensor for measuring the one or more infusion signals. In some embodiments, the detecting may be based on the one or more infusion signals exceeding a threshold.

After step 4103, the IDD 10 may pursue either step 4104*a* or 4104*b*. In step 4104*a*, the IDD 10 may notify the user that the IDD 10 has reached the end of the usable-dose zone, and may optionally shut down automatically to prevent the IDD 10 from administering further doses. In step 4104*b*, the IDD 10 may instead adjust operations conditions, depending on a user-programmed preference for responding to the end of the usable-dose zone. In particular, the IDD 10 may adjust dosage parameters to compensate for a change in AV as indicated by the one or more infusion signals to allow further dosing. For example, if a pressure signal is a low delta pressure over a dose, indicating less volume is delivered than normal, an amount of motor-on-time, (e.g., the time for the motor to be advancing), could be increased until a more typical delta (Δ) pressure is reached. Step 4103 may be repeated until the IDD 10 determines that no further dose adjustments can be made and the IDD 10 needs to shut down.

FIG. 41B provides an example of an operating plot using a pressure sensor integrated with the reservoir or fluid path. The delta pressure of each dose may be calculated as the pressure immediately after a dose minus the pressure immediately preceding a dose. When each dose is delivered by the IDD 10, an amount of pressure is generated due to flow restrictors in the fluid path. When the plunger 54 nears the closed end 34*a* of the reservoir 34, less liquid flow goes through the flow restrictors in the fluid path, so less pressure is generated with each dose and thus delta pressure will decrease. For this reason, delta pressure (ΔP) may be highly correlated with an indication of the closed end 34*a* of the reservoir 34, and thus may be used as an indication that the IDD 10 is empty. For example, as the plunger 54 nears the closed end 34*a* of the reservoir, the delta pressure may decrease with each dose delivered, as illustrated in FIG. 41B. The delta pressure may thus decrease so as to fall below a signal threshold, indicating that the IDD 10 has reached the dose-inaccurate zone. The delta pressure reaching zero (0) may then indicate that no medicament is being delivered with each dose.

FIG. 41C provides an example operating plot using the motor current as an infusion signal. With each dose, a certain amount of current is required to power the motor/gearbox 15 through one increment of motion. When the reservoir 34 is nearing empty, the motor/gearbox 15 may drive the plunger 54 against the closed end 34*a* of the reservoir 34, which increases the torque on the motor/gearbox 15 and increases the amount of current required to drive the system forward. Thus, motor current may increase as the plunger 54 nears the closed end 34*a* of the reservoir. The motor current may thus increase so as to exceed a signal threshold, indicating that the IDD 10 has reached the dose-inaccurate zone. In other words, the increase in the current with each subsequent dose may indicates that the reservoir is close to empty and the plunger hits the closed end 34*a* of the reservoir. The motor current plateauing at a high current level may then indicate that no fluid is being delivered with each dose. For example, as the plunger 54 is pressed against the closed end 34*a* of the reservoir, the motor current will increase but will remain steady.

In some embodiments, to improve the device's detection that a plunger has reached the end of the reservoir, it may be beneficial to read more than one signal to prevent false positive or false negative end of reservoir detection. If the end of reservoir detection uses signals of delta pressure, motor current, or both, transient events that affect one signal may be less likely to have an impact on the second signal. As a result, the closed end 34*a* of the reservoir 34 may only be detected in true cases of full-available volume delivery. For example, motor current may increase in the case of an occlusion event, but the closed end 34*a* of the reservoir 34 would not be detected, because delta pressure would not decrease in the event of an occlusion.

Figure 42:
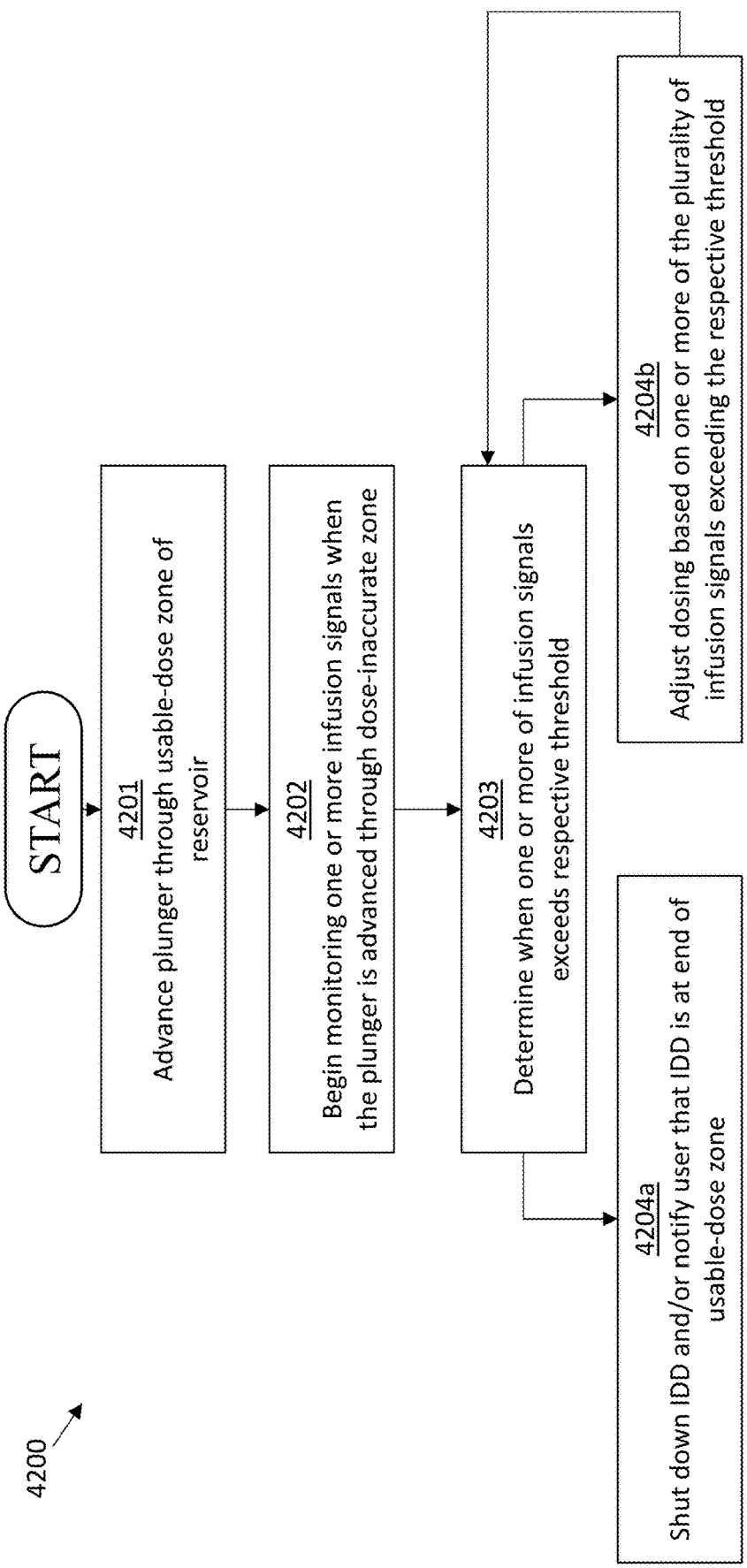
FIG. 42 illustrates an exemplary method for operating an exemplary IDD of the present disclosure based on a usable-dose zone information.

FIG. 42 illustrates an additional exemplary process 4200 for operating an IDD 10 within a usable-dose zone based on a combination of dose accuracy and the plurality of infusion signals, such as, for example, the delta pressure, the motor current, or both. The process 4200 can be carried out by any of the above-described computing devices. The process can be carried out by any of the below-described computing devices, such as the computing devices 112*a* and 112*b* (discussed in more detail with respect to FIG. 43 below, which describes the hardware and software components configured for carrying out the process 4200 in greater detail).

Process 4200 implements using receiving information regarding a usable-dose zone to potentially stop a user from administering a dose once a calculated end of the usable-dose zone of the reservoir 34 has been reached, but allow the user to proceed with the near-empty reservoir as the IDD 10 monitors for signals indicating the closed end 34*a* of the reservoir 34. For example, the dose accuracy may be used to determine an approximate end of the reservoir, at which point the infusion signal monitoring may be used to determine more exactly the closed end 34*a* of the reservoir 34 and either prevent the user from administering further doses and/or notify the user that the end of the usable-dose zone of the IDD 10 is approaching. This may minimize processing and reduce false positives by only allowing the infusion signal monitoring to detect the closed end 34*a* of the reservoir 34 when in a reasonable position to do so. Alternatively, based on whether the end of the usable-dose zone of the IDD 10 is approaching, such information may be used to adjust alternative dosage parameters to compensate for any potential difficulty in performing expected dosing.

Step 4201 comprises advancing the plunger through the usable-dose zone of the reservoir 34. Information regarding the usable-dose zone may be obtained as an estimated usable-dose zone range of the reservoir 34 using dose accuracy testing, which may be based on individual dose error (%) during dose delivery as illustrated in FIG. 40, or other methods of calibrating a usable-dose zone. At step 4202, the IDD 10 begins monitoring one or more infusion signals as the plunger nears and is advanced through the dose-inaccurate zone. The one or more infusion signals, for example, may be one or more of the delta pressure, the motor current, the motor on-time signal and the energy for each dose signal. The dose to begin monitoring the one or more infusion signals may be relative to an end of the usable-dose zone of the reservoir 34. In some embodiments, the one or more infusion signals may each be monitored at a different dose relative to the end of the usable-dose zone of the reservoir 34. Step 4203 comprises determining when each of the plurality of infusion signals, or a combination thereof, exceeds a respective threshold.

Similar to process 4100, once any number of the infusion signals exceeds or falls below a respective threshold, the IDD 10 may choose to perform either step 4204*a* or 4204*b*. Step 4204*a* comprises one or more of (1) shutting down the IDD 10 to prevent the user from administering further doses, and (2) notifying the user that the IDD 10 is at the end of a usable-dose zone of the reservoir 34. Alternatively, as shown in step 4204*b* comprises adjusting dosing parameters, such as a motor-on-time, based on one or more of the plurality of infusion signals exceeding their respective thresholds. For example, if the pressure sensor 50 reads a low delta pressure over a dose, indicating less volume is delivered than normal, the amount of a motor-on-time could be increased until a more typical delta pressure is reached. This kind of dosing compensation may be used to minimize any drop-off in dose accuracy observed as the plunger 54 reaches the closed end 34*a* of the reservoir 34. This may reduce the amount of wasted medicament leftover in the IDD 10 at the end of the IDD's life. Thus, since step 4201 may estimate whether the IDD 10 is approaching the closed end 34*a* of the reservoir 34, step 4204*b* may be implemented to selectively employ dosing compensation when the IDD 10 is known to be in a state where the plunger 54 is at, rather than approaching, the closed end 34*a* of the reservoir 34. The step 4203 may be repeated until the IDD 10 determines that no further dose adjustments can be made and the IDD 10 needs to shut down.

Different implementations of this same technique could be implemented to halt dosing at different points in the reservoir. For instance, it may be more advantageous for some IDDs to stop dosing at the mechanical end point of the reservoir 34, even if this includes dosing through the dose-inaccurate zone.

III. Embodiment Computer Systems for Use in Infusion Delivery Devices and Management Systems Techniques operating according to the principles described herein may be implemented in any suitable manner. Included in the discussion above are a series of flow charts showing the steps and acts of various processes that monitor IDD operations using a pressure sensor. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit, Field Programmable Gate Array (FPGA), or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one of ordinary skill in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of software. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application, for example as a software program application. In other implementations, the functional facilities may be adapted to interact with other functional facilities in such a way as form an operating system, including the Windows® operating system, available from the Microsoft® Corporation of Redmond, Washington. In other words, in some implementations, the functional facilities may be implemented alternatively as a portion of or outside of an operating system.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. As used herein, "computer-readable media" (also called "computer-readable storage medium") refers to tangible storage media or any tangible storage and/or transmission medium that participates in providing instructions to a processor for execution. Such a computer-readable medium may be implemented in any suitable manner, including as computer-readable storage media 1123 of FIG. 43 described below (i.e., as a portion of a computing device 112) or as a stand-alone, separate storage medium. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), optical media such as a Compact Disk (CD) or a Digital Versatile Disk (DVD), a persistent or non-persistent solid-state memory (e.g., Flash memory, Magnetic RAM, etc.), an erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored, it should be noted that any computer readable medium that is not a signal transmission may be considered non-transitory.

As used herein, tangible storage media are non-transitory and have at least one physical, structural component that has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process. In an embodiment, the computer-readable storage medium is configured to store program instructions and the processor is configured to, based on the instructions, perform steps. The network adapter may be any suitable hardware and/or software to enable the IDD 10 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media may be adapted to store data to be processed and/or instructions to be executed by a processor. The processor enables processing of data and execution of instructions. The data and instructions may be stored on the computer-readable storage media.

In some, but not all, implementations in which the techniques may be embodied as computer-executable instructions, these instructions may be executed on one or more suitable computing device(s) operating in any suitable computer system, including one or more computing devices (or one or more processors of one or more computing devices) may be programmed to execute the computer-executable instructions. A computing device or processor may be programmed to execute instructions when the instructions are stored in a manner accessible to the computing device/processor, such as in a local memory (e.g., an on-chip cache or instruction register, a computer-readable storage medium accessible via a bus, a computer-readable storage medium accessible via one or more networks and accessible by the device/processor, etc.). Functional facilities that comprise these computer-executable instructions may be integrated with and direct the operation of a single multi-purpose programmable digital computer apparatus, a coordinated system of two or more multi-purpose computer apparatuses sharing processing power and jointly carrying out the techniques described herein, a single computer apparatus or coordinated system of computer apparatuses (co-located or geographically distributed) dedicated to executing the techniques described herein, one or more Field-Programmable Gate Arrays (FPGAs) for carrying out the techniques described herein, or any other suitable system.

Figure 43:
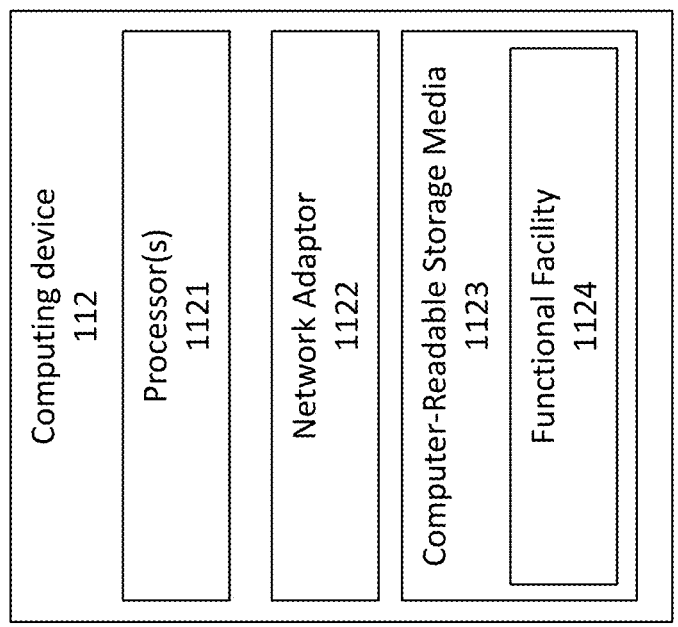
FIG. 43 is a block diagram of an exemplary implementation of a computing device that may be used for carrying out any of the above-described systems and methods.

FIG. 43 illustrates one exemplary implementation of a computing device in the form of a computing device 112 that may be used in a system implementing the techniques described herein, although others are possible. It should be appreciated that FIG. 43 is intended neither to be a depiction of necessary components for a computing device to operate in accordance with the principles described herein, nor a comprehensive depiction.

Computing device 112 may comprise at least one processor 1121, a network adapter 1122, and computer-readable storage media 1123. Computing device 112 may be, for example, a wireless controller (WC), desktop or laptop personal computer, a personal digital assistant (PDA), a smart mobile phone, a server, a wireless access point or other networking element, or any other suitable computing device. Network adapter 1122 may be any suitable hardware and/or software to enable the computing device 112 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1123 may be adapted to store data to be processed and/or instructions to be executed by one or more processors 1121. Processor 1121 enables processing of data and execution of instructions. The data and instructions may be stored on the computer-readable storage media 1123.

The data and instructions stored on computer-readable storage media 1123 may comprise computer-executable instructions implementing techniques which operate according to the principles described herein. In the example of FIG. 43, computer-readable storage media 1123 stores computer-executable instructions implementing various facilities and storing various information as described above.

Example functional facility 1124 present in the computer-readable storage media 1123 can include programming instructions for pressure detection, pressure analysis, order of operation, lockout, and alerts.

The functional facility 1124 can include one or more functional facilities for pressure detection, which may comprise one or more programming instructions for receiving data from the pressure sensor 50. The data from the pressure sensor 50 can be stored in one or more memory components, internal or external, of the computing device 112. The one or more functional facilities for pressure detection may comprise one or more programming instructions for detecting a fill event, detecting a fill volume, calibrating and/or calculating a mechanical compliance, detecting air in a fluid path, detecting an occlusion in a fluid path after removal of an insertion seal assembly, detecting deployment of one or more components of a fluid path, detecting an occlusion during operation of an IDD, detecting an empty reservoir, or combinations thereof. The one or more functional facilities for pressure detection may comprise one or more programming instructions for performing any number of processes 1000, 1600, 1700, 1800, 2000, 2100, 2200, 2400, 2500, 2600, 2700, 2800, 3000, 3200, 3300, 3700, 3800, 3900, 4100, 4200, or any combinations thereof.

In some embodiments, one or more functional facilities for pressure detection may comprise one or more programming instructions for determining whether the detected pressure in the fluid path 900 exceeds or deviates from the one or more threshold pressure values. For instance, in some embodiments, it can be determined whether the detected pressure in the fluid path 900 exceeds (e.g., is greater than) an upper pressure threshold value. For instance, in some embodiments, it can be determined whether the detected pressure in the fluid path 900 exceeds (e.g., is less than) a lower pressure threshold value. For instance, in some embodiments, it can be determined whether the detected pressure in the fluid path 900 extends beyond an acceptable range of pressures (e.g., is greater than an upper pressure threshold or less than a lower pressure threshold). In some embodiments, it can be determined whether the detected pressure in the fluid path 900 exceeds a threshold pressure value for a set or pre-determined amount of time (that is, extends beyond a threshold pressure value and remains beyond a threshold pressure value for a set amount of time). Such analysis can eliminate false positives associated with only determining whether the detected pressure in the fluid path 900 exceeds a pressure threshold value. In some embodiments, it can be determined whether the moving average of the detected pressure in the fluid path 900 (i.e., the average pressure in the fluid path 900 over any consecutive period of a set or predetermined amount of time (e.g., the average over any five second period)) exceeds a threshold average pressure value. Such analysis can eliminate false positives associated with only determining whether the detected pressure in the fluid path 900 exceeds a pressure threshold value. In some embodiments, it can be determined whether a rate of change of the detected pressure in the fluid path 900 exceeds a threshold rate of change value. In some embodiments, it can be determined whether the pressure signature of the detected pressure in the fluid path 900 (e.g., the shape of the pressure curve of detected pressure in the fluid path 900) deviates from a nominal pressure signature.

The functional facility 1124 can include one or more functional facilities for order of operation, which may comprise one or more programming instructions for determining the order or sequence of events taken in the operation of the IDD 10. In some embodiments, the computing device 112 can be configured to maintain a log of certain events concerning the use of the IDD 10. In some embodiments, the computing device 112 can be configured to maintain a log of the operation of the IDD 10 controlled by the electrical sub-system. For instance, based on a prompt from a user, the electrical sub-subsystem can be configured to operate a motor to drive the screw train assembly 42 to dispense medicine from the reservoir 34. The screw train assembly 42 can be driven to prime the fluid path 900 or to deliver a dose of medicament from the IDD 10. The computing device 112 can maintain a log of such events including the time at which such events were carried out, instructed to be carried out, and/or scheduled to be carried out. The functional facility 1124 can include one or more programming instructions for determining the relative sequence of events in the operation of the IDD 10 based on the log of events controlled or initiated by the electrical sub-system and the above-described determinations on the occurrence and time of occurrence of the deployment of one or more components of the fluid path 900 (either determined directly or indirectly based on the time of insertion seal assembly 20 removal). In other words, at every time segment during the operation of the IDD 10, the controller 112 can be configured to determine whether an instruction to prime the fluid path 900 was provided or scheduled, an instruction to deliver a dose of medicament from the IDD 10 was provided or scheduled, and whether one or more components of the fluid path 900 is in the pre-deployed or deployed configuration. Therefore, the relative time at which events such as priming the fluid path 900, delivery of a dose of medicament, and deployment of one or more components of the fluid path 900 occurred or are scheduled to occur (e.g., the temporal sequence) can be determined.

The functional facility 1124 can include one or more functional facilities for lockout, which may comprise one or more programming instructions for preventing use of the IDD 10 to perform one or more tasks. The prevention of the one or more tasks can be locking a user out of initiating the one or more tasks. The prevention of the one or more tasks can be disabling the IDD 10 from performing the one or more tasks. In some embodiments, based on the determinations made regarding the order of operation of the IDD 10, the IDD 10 can be prevented from performing one or more tasks out of a desired sequence of operation of the IDD 10. For instance, if it is determined that one or more components of the fluid path 900 have been deployed prior to priming the fluid path 900, the IDD 10 can be prevented from both priming the fluid path 900 and delivering a dose of medicament. This can ensure that if the catheter 48 is already inserted into the user's skin, any air bubbles in the fluid path 900 are not delivered to the patient. Similarly, if it is determined that the one or more components of the fluid path 900 have not been deployed, the IDD 10 can be prevented from delivering a dose of medicament (even if priming has already occurred). This can ensure that a dose of medicament is not wasted (e.g., expelled from the IDD 10 but not delivered into the user's skin).

The functional facility 1124 can include one or more functional facilities for alerts, which may comprise one or more programming instructions for presenting an alert to the user regarding IDD 10 operation. In some embodiments, the alert may be based on a predefined error code stored in the non-transitory computer-readable medium. The predefined error code may correspond to a message related to a specific alert type or process, e.g., processes 1000, 1600, 1700, 1800, 2000, 2100, 2200, 2400, 2500, 2600, 2700, 2800, 3000, 3200, 3300, 3700, 3800, 4000, 4100, 4200, any combinations thereof, or any steps within each of the above processes.

In some embodiments, the alert can be provided on the IDD 10 or on a remote device, such as a wireless controller or external computing device. The alert can be visual, auditory, and/or haptic. The alert can indicate when the IDD 10 is prevented from performing one or more tasks. For instance, in some embodiments, the alert can indicate that the IDD 10 is prevented from both priming the fluid path 900 and delivering a dose of medicament. In such cases, the alert can further include a prompt for the user to discard the IDD 10, as the IDD 10 cannot be used for its desired operation. In some embodiments, the alert can indicate that the IDD 10 is prevented from delivering a dose of medicament (even if priming has already occurred). In such cases, the alert can further include a prompt for the user to deploy the one or more components of the fluid path 900. That is, if the user has primed the fluid path 900 but is prevented from administering a dose because the one or more components of the fluid path 900 are not deployed, the alert can prompt the user to deploy the one or more components of the fluid path 900.

While not illustrated in FIG. 43, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Figure 44:
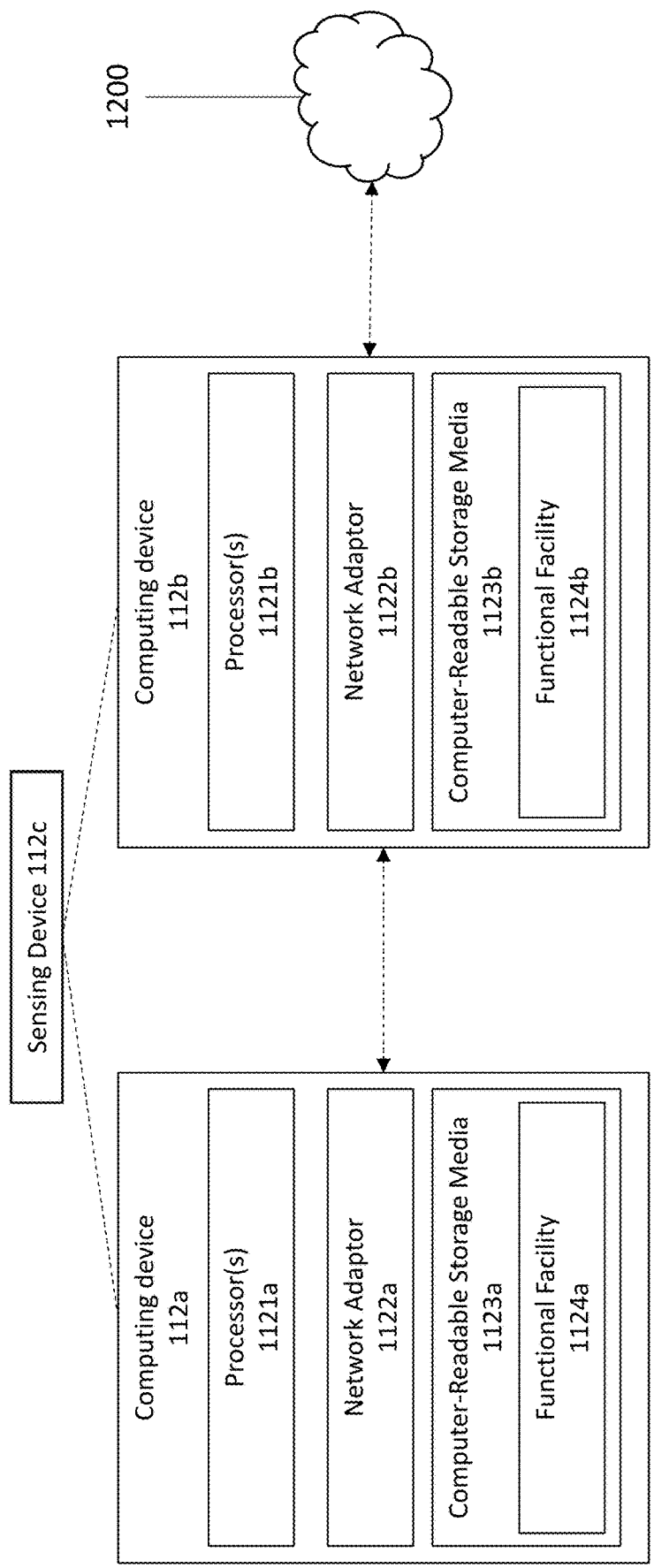
FIG. 44 is a block diagram of an exemplary implementation of at least one computing device that may be used for carrying out any of the above-described systems and methods.

FIG. 44 illustrates one exemplary implementation of an operating environment for carrying out any of the above-described systems and methods is depicted.

The operating environment can include a first computing device 112a, a second computing device 112b, and a cloud storage facility 1200. In some embodiments, the first computing device 112a can include at least one processor 1121a, a network adapter 1122a, computer-readable storage media 1123a, and functional facility 1124a. In some embodiments, the first computing device 112a can be internal to the IDD 10. For instance, in some embodiments, the first computing device 112a can be implemented in the electrical sub-subsystem. In some embodiments, the processor 1121a can be the MCU 52 of the electrical sub-subsystem discussed above.

In some embodiments, the second computing device 112b can include at least one processor 1121b, a network adapter 1122b, computer-readable storage media 1123b, and functional facility 1124b. In some embodiments, the second computing device 112b can be a WC communicatively coupled with the IDD 10, or the first computing device 112a. In some embodiments, the first computing device 112a and the second computing device 112b can be configured to transmit data, signals, instructions, calculations, and the like between each other. In some embodiments, the first computing device 112a and the second computing device 112b can be configured to wirelessly communicate with each other.

In some embodiments, the second computing device 112b can be a remote consumer electronic device or WC comprising applications and cloud service. The term "cloud service" refers to a service that is provided over a network connection, via a non-local computer. For instance, the second computing device 112b can be communicatively coupled with the cloud storage facility 1200. The second computing device 112b can be a mobile phone, such as a smartphone configured with, for example, Bluetooth®, Bluetooth® low energy, mobile, Wi-Fi or other communications protocols and modalities. In some embodiments, the second computing device 112b can be an electronic tablet or a laptop or desktop computer. In some embodiments, the second computing device 112b can be a smart watch. In some embodiments, the second computing device 112b can be a dedicated WC for use with the first computing device 112a or the IDD 10. In some embodiments, the first computing device 112a (i.e., the IDD 10) is paired with the second computing device 112b as an initial step in the user experience. The IDD 10 includes the power button 6 (FIG. 4) which can be depressed by the user and will blink, noting that it is ready to pair with the second computing device 112b. The application running on the second computing device 112b can ask the user to pair the IDD 10 with the second computing device 112b. The second computing device 112b can notify the user when the IDD 10 has successfully been paired with it.

In some embodiments, either the first computing device 112a, the second computing device 112b or both may be in communication with a sensing device 112c. In some embodiments, the sensing device may be either the first computing device 112a or the second computing device 112b. In some embodiments, the sensing device is a glucose sensing device. In some embodiments, the glucose sensing device is a continuous glucose sensing device or a continuous glucose monitor (CGM). In some embodiments, the glucose sensing device is directly in communication with the IDD 10. In some embodiments, the glucose sensing device is in communication with the WC. When communicatively coupled, the first computing device 112a (i.e., the IDD 10) and the second computing device 112b (i.e., the WC) can transmit data and instructions therebetween. The second computing device 112b can be a device that controls and monitors the operation of the IDD 10, such as operation of the pump, alarms, etc., using wireless technology. The second computing device 112b can recognize user inputs via a power button 6 and graphical user interface (GUI). The second computing device 112b can include a mobile application that a user can launch. The mobile application can be provided, for example, by a vendor of the IDD 10 that is being operated. The application can provide the necessary drivers and communication protocols to support fulfillment of system functions.

In some embodiments, the second computing device 112b of the present disclosure can be configured to communicate insulin delivery instructions to the IDD 10, which is configured to receive the insulin delivery instructions. The second computing device 112b can include a user-interactive touchscreen display and at least one processor 1121b. The second computing device 112b can present audible, visual, and haptic feedback to a user. The second computing device 112b can include a Wi-Fi radio and a processor 1121b for sending and receiving data to a cloud services interface (e.g., cloud storage facility 1200). The processor 1121b processes data associated with bolus dose calculator entered inputs, tracking of basal and bolus dosing in progress, and tracking confirmations and alarms. The second computing device 112b can store data associated with paring information, settings, basal and bolus dose pre-set programs, entered dose calculator settings, entered blood glucose reading, comment, carbs, entered dose calculator inputs, delivered basal and bolus doses, and all messages received from the first computing device (i.e., the IDD 10) via the Bluetooth link. The second computing device 112b can manage faults for certain conditions, including but not limited to, memory corruption, lower power, and synchronization.

Either or both of the first computing device 112a and the second computing device 112b can be configured in the same manner. Therefore, the internal components of the first computing device 112a and the second computing device 112b are not discussed in detail. Moreover, it should be appreciated that any of the above-described functional facilities can be stored in either or both of the first computing device 112a and the second computing device 112b. Therefore, the above-described methods and computations/determinations can be carried out entirely on the first computing device 112a, entirely on the second computing device 112b, or responsibilities (e.g., particular steps in the above-described methods or particular computations/determinations) can be shared between the first computing device 112*a* and the second computing device 112*b*, such that some steps of the above-described methods are carried out by the first computing device 112*a* and some steps of the above-described methods are carried out by the second computing device 112*b*.

In some embodiments, the above-described functional facility 1124*a* can be stored on the first computing device 112*a* (i.e., the IDD 10) and executed by an internal MCU 52/1121*a* of the first computing device 112*a*. In some embodiments, the above-described functional facility 1124*b* can be stored on the second computing device 112*b* (i.e., the WC) and executed by a processor 1121*b* of the second computing device 112*b*. Merely as an example, the instructions stored in the functional facility 1124*a* can be executed by a local processor of the first computing device 112*a* (i.e., the IDD 10), such that the first computing device 112*a* can determine whether and when contact between the plunger 54 and the reservoir 34 occurred. The first computing device 112*a* can transmit this determination to the second computing device 112*b* (i.e., the WC). The instructions stored in the functional facility 1124*b* can be executed by a processor of the second computing device 112*b*. The second computing device 112*b* can then transmit the determined adjustment of dosage parameters in the operation of the IDD 10 to the first computing device 112*a* (i.e., the IDD 10).

Non-limiting embodiments of the present disclosure are set out in the following clauses:

Clause 1. An infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: receive pressure data detected by the at least one pressure sensor while the fluid reservoir is being filled with a therapeutic fluid so as to translate the plunger within the fluid reservoir; determine when a fill event has occurred at a first time based on the pressure data satisfying a threshold value; and prevent or allow operation of the infusion delivery device at a second time based on whether a difference between the second time and the first time exceeds a degradation time of the therapeutic fluid.

Clause 2. The infusion delivery device of clause 1, wherein a time stamp is saved in memory when the pressure data satisfies the threshold value.

Clause 3. The infusion delivery device of clause 1 or clause 2, wherein the at least one pressure sensor interfaces with the distal end of the fluid reservoir.

Clause 4. The infusion delivery device of any one of clauses 1-3, wherein the instructions, when executed by the processor, cause the processor to alert a user based on a predefined error code corresponding to an amount of time the infusion delivery device is in use.

Clause 5. The infusion delivery device of any one of clauses 1-4, wherein the instructions, when executed by the processor, cause the processor to transmit one or more notifications to a user to alert the user of an amount of time the infusion delivery device has remaining to be in use.

Clause 6. The infusion delivery device of any one of clauses 1-5, wherein the threshold value is pre-programmed in the non-transitory computer-readable medium.

Clause 7. The infusion delivery device of any one of clauses 1-6, wherein the threshold value is based on a sum of a pre-defined base pressure and a pressure measurement from the at least one pressure sensor when the infusion delivery device is first paired to a controller.

Clause 8. The infusion delivery device of any one of clauses 1-7, wherein the threshold value is driven by an amount of pressure required to push the plunger through the fluid reservoir.

Clause 9. A method comprising: setting a pressure threshold of an infusion delivery device, wherein the infusion delivery device comprises: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; monitoring a pressure in the fluid reservoir or fluid path while the fluid reservoir is being filled with a therapeutic fluid; registering a fill event when the monitored pressure exceeds the pressure threshold and recording a first time of the fill event; and preventing or allowing operation of the infusion delivery device at a second time based on whether a difference between the second time and the first time exceeds a degradation time of the therapeutic fluid.

Clause 10. The method of clause 9, further comprising causing one or more notifications to be transmitted to alert a user of an amount of time the infusion delivery device is in use.

Clause 11. The method of clause 9 or clause 10, further comprising causing one or more notifications to be transmitted to alert a user of an amount of time the infusion delivery device has remaining to be in use.

Clause 12. The method of any one of clauses 9-11, wherein the registering is performed during a time when a user is instructed to fill the infusion delivery device.

Clause 13. The method of any one of clauses 9-12, wherein the pressure threshold is pre-programmed in the infusion delivery device.

Clause 14. The method of any one of clauses 9-13, wherein the pressure threshold is based on a sum of a pre-defined constant and a pressure measurement when the infusion delivery device is first paired to a controller.

Clause 15. The method of any one of clauses 9-14, wherein the pressure threshold is driven by an amount of pressure required to push the plunger through the fluid reservoir.

Clause 16. An infusion management system comprising: an infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with at least one pressure sensor and a non-transitory computer-readable medium having encoded thereon instructions that, when executed by the processor, cause the processor to: receive pressure data detected by the at least one pressure sensor while the fluid reservoir is being filled with a therapeutic fluid so as to translate the plunger within the fluid reservoir; determine when a fill event has occurred at a first time based on the pressure data satisfying a threshold value; and prevent or allow operation of the infusion delivery device at a second time based on whether a difference between the second time and the first time exceeds a degradation time of the therapeutic fluid; and at least one controller in communication with the infusion delivery device, wherein the at least one controller is configured to exchange data or instructions with the infusion delivery device.

Clause 17. The infusion management system of clause 16, wherein the at least one controller comprises a user interface for communicating with a user.

Clause 18. The infusion management system of clause 16 or clause 17, wherein the at least one controller comprises a smart phone.

Clause 19. The infusion management system of any one of clauses 16-18, wherein the processor is configured to transmit one or more notifications to the at least one controller.

Clause 20. The infusion management system of any one of clauses 16-19, wherein the at least one controller comprises a dedicated wireless remote controller.

Clause 21. An infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: record a first pressure signal when the plunger is at a first position, record a second pressure signal when the plunger is at a second position distal to the first position, calibrate a mechanical compliance (MC) value based on a difference between the first pressure signal and the second pressure signal and based on a difference between the first position and the second position, and adjust an operation of the infusion delivery device based on the MC value.

Clause 22. The infusion delivery device of clause 21, wherein the first pressure signal is recorded when the plunger is translated distally to contact a liquid in the fluid reservoir.

Clause 23. The infusion delivery device of clause 21 or clause 22, wherein the instructions, when executed by the processor, cause the processor to drive the plunger to the second position for a pre-determined number of increments.

Clause 24. The infusion delivery device of any one of clauses 21-23, wherein the second pressure signal is a predetermined second pressure signal, and wherein the instructions, when executed by the processor, cause the processor to drive the plunger to the second position until the at least one pressure sensor detects the predetermined second pressure signal.

Clause 25. The infusion delivery device of any one of clauses 21-24, wherein the instructions, when executed by the processor, cause the processor to calculate a change in MC based on a difference between the MC value and an expected MC value, wherein the expected MC value is stored in the non-transitory computer-readable medium.

Clause 26. The infusion delivery device of any one of clauses 21-25, wherein adjusting the operation comprises preventing use of the infusion delivery device if the change in MC satisfies a predetermined threshold.

Clause 27. The infusion delivery device of any one of clauses 21-26, wherein the instructions, when executed by the processor, cause the processor to: determine an air volume in the fluid reservoir based on a compliance difference between the MC value and an expected compliance value.

Clause 28. The infusion delivery device of any one of clauses 21-27, wherein the instructions, when executed by the processor, cause the processor to prevent a user from administering doses when the air volume exceeds a predetermined threshold.

Clause 29. The infusion delivery device of any one of clauses 21-28, wherein the instructions, when executed by the processor, cause the processor to transmit one or more notifications to a user when the air volume exceeds a predetermined threshold.

Clause 30. The infusion delivery device of any one of clauses 21-29, wherein the instructions, when executed by the processor, cause the processor to transmit one or more notifications to a user to proceed dosing with caution based on the air volume.

Clause 31. A method for an infusion delivery device comprising: recording a first pressure signal when a plunger of an infusion delivery device is at a first position, wherein the infusion delivery device comprises: a fluid reservoir having a proximal end, a distal end, and the plunger disposed inside the fluid reservoir and moveable therein; a fluid path in fluid communication with the fluid reservoir; and at least one pressure sensor interfacing at least one of the fluid reservoir or the fluid path; recording a second pressure signal when the plunger is at a second position distal to the first position, calibrating a mechanical compliance (MC) value based on a difference between the first pressure signal and the second pressure signal and based on a difference between the first position and the second position, and adjusting an operation of the infusion delivery device based on the MC value.

Clause 32. The method of clause 31, wherein the first pressure signal is recorded when the plunger is translated distally to contact a medicament in the fluid reservoir.

Clause 33. The method of clause 31 or clause 32, further comprising driving the plunger to the second position for a predetermined number of increments.

Clause 34. The method of any one of clauses 31-33, wherein the second pressure signal is a predetermined second pressure signal.

Clause 35. The method of any one of clauses 31-34, further comprising driving the plunger to the second position until the at least one pressure sensor detects the predetermined second pressure signal.

Clause 36. The method of any one of clauses 31-35, further comprising calculating a change in MC based on a difference between the MC value and an expected MC value.

Clause 37. The method of any one of clauses 31-36, wherein adjusting the operation comprises preventing use of the infusion delivery device if the change in MC satisfies a predetermined threshold.

Clause 38. The method of any one of clauses 31-37, further comprising: determining an air volume in the fluid reservoir based on a compliance difference between the MC value and an expected compliance value.

Clause 39. The method of any one of clauses 31-38, wherein the expected compliance value is predetermined or interpolated based on a mechanical compliance (MC) value of the fluid reservoir when the fluid reservoir is filled with each of one or more varying volumes of liquid.

Clause 40. The method of any one of clauses 31-39, further comprising, when the air volume exceeds a predetermined threshold, preventing a user from administering doses and/or notifying a user of an air volume.

Clause 41. The method of any one of clauses 31-40, further comprising notifying a user to proceed dosing with caution based on the air volume.

Clause 42. An infusion management system comprising: an infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: record a first pressure signal when the plunger is at a first position, record a second pressure signal when the plunger is at a second position distal to the first position, calibrate a mechanical compliance (MC) value based on a difference between the first pressure signal and the second pressure signal and based on a difference between the first position and the second position, and adjust an operation of the infusion delivery device based on the MC value; and at least one controller in communication with the infusion delivery device, wherein the at least one controller is configured to exchange data or instructions with the infusion delivery device.

Clause 43. The infusion management system of clause 42, wherein the at least one controller comprises a user interface for communicating with a user.

Clause 44. The infusion management system of clause 42 or clause 43, wherein the at least one controller comprises a smart phone.

Clause 45. The infusion management system of any one of clauses 42-44, wherein the processor is configured transmit one or more notifications to the at least one controller.

Clause 46. The infusion management system of any one of clauses 42-45, wherein the at least one controller comprises a dedicated wireless remote controller.

Clause 47. The infusion management system of any one of clauses 42-46, wherein the instructions, when executed by the processor, cause the processor to: determine an air volume in the fluid reservoir based on a compliance difference between the MC value and an expected compliance value.

Clause 48. An infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; a processor in communication with the at least one pressure sensor and a non-transitory computer-readable medium having encoded thereon instructions that, when executed by the processor, cause the processor to: determine whether the fluid path is in a pre-deployed configuration or a deployed configuration based on comparing pressure data collected from the at least one pressure sensor to one or more threshold values.

Clause 49. The infusion delivery device of clause 48, wherein the fluid path comprises one or more components in fluid communication with one another between the fluid reservoir at a first end and a catheter tip at a second end.

Clause 50. The infusion delivery device of clause 48 or clause 49, wherein: in the pre-deployed configuration, the one or more components of the fluid path has a first length, and in the deployed configuration, the one or more components of the fluid path has a second length that is greater than the first length.

Clause 51. The infusion delivery device of any one of clauses 48-50, wherein the fluid path comprises a catheter and a needle.

Clause 52. The infusion delivery device of any one of clauses 48-51, wherein: in the pre-deployed configuration, the needle is disposed within the catheter; and in the deployed configuration, the needle is retracted from the catheter.

Clause 53. The infusion delivery device of any one of clauses 48-52, wherein the pressure data comprises pressure data in the fluid path.

Clause 54. The infusion delivery device of any one of clauses 48-53, wherein the one or more threshold values comprises one or more of an amount of time for each of one or more pressure thresholds to be exceeded, a threshold moving average of pressure, a threshold rate of change of pressure, or a combination thereof.

Clause 55. The infusion delivery device of any one of clauses 48-54, wherein the one or more threshold values is pre-programmed in the non-transitory computer-readable medium.

Clause 56. The infusion delivery device of any one of clauses 48-55, wherein the instructions, when executed by the processor, cause the processor to determine a status of the infusion delivery device, wherein the status comprises one or more of the fluid path being in a pre-deployed configuration, the fluid path being in a deployed configuration, a priming of the fluid path, a delivery of a dose of medicament, or a combination thereof.

Clause 57. The infusion delivery device of any one of clauses 48-56, wherein, when the status comprises the fluid path being in the deployed configuration, the instructions, when executed by the processor, cause the processor to prevent priming the fluid path.

Clause 58. The infusion delivery device of any one of clauses 48-57, wherein, when the status comprises the fluid path being in the pre-deployed configuration, the instructions, when executed by the processor, cause the processor to prevent delivery of the dose of medicament.

Clause 59. The infusion delivery device of any one of clauses 48-58, wherein the instructions, when executed by the processor, cause the processor to generate an alert to a user based on one or more events during operation of the infusion delivery device, wherein the one or more events are based on a time of one or more of the fluid path being in a pre-deployed configuration, the fluid path being in a deployed configuration, a priming of the fluid path, a delivery of a dose of medicament, or a combination thereof.

Clause 60. A method for an infusion delivery device comprising: receiving pressure data from at least one pressure sensor of an infusion delivery device, wherein the infusion delivery device comprises: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir and the fluid path; and determining whether the fluid path is in a pre-deployed configuration or a deployed configuration based on comparing pressure data received from the at least one pressure sensor to one or more threshold values.

Clause 61. The infusion delivery device of clause 60, wherein the fluid path comprises one or more components in fluid communication with one another between the fluid reservoir at a first end and a catheter tip at a second end.

Clause 62. The infusion delivery device of clause 60 or clause 61, wherein: in the pre-deployed configuration, the one or more components of the fluid path has a first length, and in the deployed configuration, the one or more components of the fluid path has a second length that is greater than the first length.

Clause 63. The infusion delivery device of any one of clauses 60-62, wherein the fluid path comprises a catheter and a needle.

Clause 64. The infusion delivery device of any one of clauses 60-63, wherein: in the pre-deployed configuration, the needle is disposed within the catheter; and in the deployed configuration, the needle is retracted from the catheter.

Clause 65. The method of any one of clauses 60-64, wherein the pressure data comprises pressure data in the fluid path.

Clause 66. The method of any one of clauses 60-65, wherein the one or more threshold values comprises one or more of an amount of time for each of one or more pressure thresholds to be exceeded, a threshold moving average of pressure, a threshold rate of change of pressure, or a combination thereof.

Clause 67. The method of any one of clauses 60-66, wherein the one or more threshold values is pre-programmed in the infusion delivery device.

Clause 68. The method of any one of clauses 60-67, further comprising determining a status of the infusion delivery device, wherein the status comprises one or more of the fluid path being in a pre-deployed configuration, the fluid path being in a deployed configuration, a priming of the fluid path, a delivery of a dose of medicament, or a combination thereof.

Clause 69. The method of any one of clauses 60-68, further comprising preventing priming the fluid path when the status comprises the fluid path being in the deployed configuration.

Clause 70. The method of any one of clauses 60-69, further comprising preventing delivery of the dose of medicament when the status comprises the fluid path being in the pre-deployed configuration.

Clause 71. The method of any one of clauses 60-70, further comprising generating an alert to a user based on one or more events during operation of the infusion delivery device, wherein the one or more events are based on a time of one or more of the fluid path being in a pre-deployed configuration, the fluid path being in a deployed configuration, a priming of the fluid path, a delivery of a dose of medicament, or a combination thereof.

Clause 72. The method of any one of clauses 60-71, further comprising preventing the infusion delivery device from performing one or more tasks if it is determined that the fluid path is not deployed in a desired sequence with respect to one or more events taken in operation of the infusion delivery device.

Clause 73. An infusion management system comprising: an infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: determine whether the fluid path is in a pre-deployed configuration or a deployed configuration based on comparing pressure data collected from the at least one pressure sensor to one or more threshold values; and at least one controller in communication with the infusion delivery device, wherein the at least one controller is configured to exchange data or instructions with the infusion delivery device.

Clause 74. The infusion management system of clause 73, wherein the at least one controller comprises a user interface for communicating with a user.

Clause 75. The infusion management system of clause 73 or clause 74, wherein the at least one controller comprises a smart phone.

Clause 76. The infusion management system of any one of clauses 73-75, wherein the processor is configured transmit one or more notifications to the at least one controller.

Clause 77. The infusion management system of any one of clauses 73-76, wherein the at least one controller comprises a dedicated wireless remote controller.

Clause 78. An infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: set a plurality of mechanical compliance (MC) values of the fluid reservoir, each MC value corresponding to a respective volume of liquid in the fluid reservoir; calculate a plurality of occlusion pressure thresholds, wherein each of the plurality of occlusion pressure thresholds is based on a respective MC value of the plurality of MC values; monitor a signal corresponding to a pressure in the fluid reservoir; and register an occlusion when the pressure exceeds an occlusion pressure threshold of the plurality of occlusion pressure thresholds, the occlusion pressure threshold corresponding to a volume of liquid in the fluid reservoir.

Clause 79. The infusion delivery device of clause 78, wherein the plurality of MC values of the fluid reservoir are variable based on the respective volume of the liquid in the fluid reservoir, a medicament delivery rate, or a combination thereof.

Clause 80. The infusion delivery device of clause 78 or clause 79, wherein each of the plurality of occlusion pressure thresholds is pre-programmed in the non-transitory computer-readable medium.

Clause 81. The infusion delivery device of any one of clauses 78-80, wherein each of the plurality of occlusion pressure thresholds is static.

Clause 82. The infusion delivery device of any one of clauses 78-81, wherein each of the plurality of occlusion pressure thresholds is variable.

Clause 83. The infusion delivery device of any one of clauses 78-82, wherein the instructions, when executed by the processor, causes the processor to transmit one or more notifications to a user with an alert when the occlusion is registered, wherein the alert comprises a visual alert, an audible alert, or a combination thereof.

Clause 84. A method for an infusion delivery device comprising: setting a plurality of mechanical compliance (MC) values of a fluid reservoir of an infusion delivery device, each MC value corresponding to a respective volume of liquid in the fluid reservoir, wherein the infusion delivery device comprises: the fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; calculating a plurality of occlusion pressure thresholds, wherein each of the plurality of occlusion pressure thresholds is based on a respective MC value of the plurality of MC values; monitoring at least one signal corresponding to a pressure in the fluid reservoir; and registering an occlusion when the pressure exceeds an occlusion pressure threshold of the plurality of occlusion pressure thresholds, the occlusion pressure threshold corresponding to a volume of liquid in the fluid reservoir.

Clause 85. The method of clause 84, wherein the plurality of MC values of the fluid reservoir are variable based on the respective volume of the liquid in the fluid reservoir, a medicament delivery rate, or a combination thereof.

Clause 86. The method of clause 84 or clause 85, wherein each of the plurality of occlusion pressure thresholds is pre-programmed in the infusion delivery device.

Clause 87. The method of any one of clauses 84-86, wherein each of the plurality of occlusion pressure thresholds is static.

Clause 88. The method of any one of clauses 84-87, wherein each of the plurality of occlusion pressure thresholds is variable.

Clause 89. The method of any one of clauses 84-88, further comprising notifying a user with an alert when the occlusion is registered, wherein the alert comprises a visual alert, an audible alert, or a combination thereof.

Clause 90. An infusion management system comprising: an infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: set a plurality of mechanical compliance (MC) values of the fluid reservoir, each MC value corresponding to a respective volume of liquid in the fluid reservoir; calculate a plurality of occlusion pressure thresholds, wherein each of the plurality of occlusion pressure thresholds is based on a respective MC value of the plurality of MC values; monitor at least one signal corresponding to a pressure in the fluid reservoir; and register an occlusion when the pressure exceeds an occlusion pressure threshold of the plurality of occlusion pressure thresholds, the occlusion pressure threshold corresponding to a volume of liquid in the fluid reservoir; and at least one controller in communication with the infusion delivery device, wherein the at least one controller is configured to exchange data or instructions with the infusion delivery device.

Clause 91. The infusion management system of clause 90, wherein the at least one controller comprises a user interface for communicating with a user.

Clause 92. The infusion management system of clause 90 or clause 91, wherein the at least one controller comprises a smart phone.

Clause 93. The infusion management system of any one of clauses 90-92, wherein the processor is configured transmit one or more notifications to the at least one controller.

Clause 94. The infusion management system of any one of clauses 90-93, wherein the at least one controller comprises a dedicated wireless controller.

Clause 95. An infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: monitor one or more pressure signals; and determine an end of the fluid reservoir based on the one or more pressure signals.

Clause 96. The infusion delivery device of clause 95, wherein the end of the fluid reservoir corresponds to an end of a usable-dose zone, wherein the end of the usable-dose zone is based on an accuracy of an infusion dosage.

Clause 97. The infusion delivery device of clause 95 or clause 96, wherein the instructions, when executed by the processor, cause the processor to adjust operation by one or more of preventing a user from administering doses and notifying the user that the infusion delivery device is at or near the end of the usable-dose zone.

Clause 98. The infusion delivery device of any one of clauses 95-97, wherein the end of the fluid reservoir is relative to an initial fill volume of the fluid reservoir.

Clause 99. The infusion delivery device of any one of clauses 95-98, wherein the end of the fluid reservoir is based on an error between an actual volume of medicament in the fluid reservoir (AV) to an expected volume of medicament in the fluid reservoir (EV), wherein the error exceeds a predetermined threshold.

Clause 100. The infusion delivery device of any one of clauses 95-99, wherein the AV is calculated based on the one or more pressure signals.

Clause 101. The infusion delivery device of any one of clauses 95-100, wherein the EV is pre-programmed in the non-transitory computer-readable medium.

Clause 102. The infusion delivery device of any one of clauses 95-101, wherein the at least one pressure sensor comprises a pressure sensor, and wherein one or more pressure signals comprises a pressure signal.

Clause 103. A method for an infusion delivery device comprising: monitoring one or more pressure signals in an infusion delivery device, wherein the infusion delivery device comprises: a fluid reservoir having a proximal end, a distal end, and a plunger disposed inside the fluid reservoir and moveable therein; a fluid path in fluid communication with the fluid reservoir; and at least one pressure sensor interfacing at least one of the fluid reservoir or the fluid path; and determining an end of the fluid reservoir based on one or more pressure signals.

Clause 104. The method of clause 103, wherein the end of the fluid reservoir corresponds to an end of a usable-dose zone, wherein the end of the usable-dose zone is based on an accuracy of an infusion dosage.

Clause 105. The method of clause 103 or clause 104, further comprising adjusting operation by one or more of preventing a user from administering doses and notifying the user that the infusion delivery device is at or near the end of the usable-dose zone.

Clause 106. The method of any one of clauses 103-105, wherein the end of the fluid reservoir is relative to an initial fill volume of the fluid reservoir.

Clause 107. The method of any one of clauses 103-106, wherein the end of the fluid reservoir is based on an error between an actual volume of medicament in the fluid reservoir (AV) to an expected volume of medicament in the fluid reservoir (EV), wherein the error exceeds a predetermined threshold.

Clause 108. The method of any one of clauses 103-107, wherein the AV is calculated based on the one or more pressure signals.

Clause 109. The method of any one of clauses 103-108, wherein the EV is pre-programmed in the infusion delivery device.

Clause 110. The method of any one of clauses 103-109, wherein the at least one pressure sensor comprises a pressure sensor, and wherein the one or more pressure signals comprises a pressure signal.

Clause 111. An infusion management system comprising: an infusion delivery device comprising: a fluid reservoir having a proximal end, a distal end, and a plunger disposed inside the fluid reservoir and moveable therein; a fluid path in fluid communication with the fluid reservoir; at least one pressure sensor interfacing at least one of the fluid reservoir or the fluid path; and a processor in communication with the at least one pressure sensor and a non-transitory computer-readable medium having encoded thereon instructions that, when executed by the processor, cause the processor to: monitor one or more pressure signals; and determine an end of the fluid reservoir based on the one or more pressure signals; and at least one controller in communication with the infusion delivery device, wherein the at least one controller is configured to exchange data or instructions with the infusion delivery device.

Clause 112. The infusion management system of clause 111, wherein the at least one controller comprises a user interface for communicating with a user.

Clause 113. The infusion management system of clause 111 or clause 112, wherein the at least one controller comprises a smart phone.

Clause 114. The infusion management system of any one of clauses 111-113, wherein the processor is configured transmit one or more notifications to the at least one controller.

Clause 115. The infusion management system of any one of clauses 111-114, wherein the at least one controller comprises a dedicated wireless controller.

Clause 116. The infusion management system of any one of clauses 111-115, wherein the at least one pressure sensor comprises a pressure sensor, and wherein the one or more pressure signals comprises a pressure signal.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein can be employed. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification, embodiments have been described in a way which enables a clear and concise specification to be written, but it is intended and will be appreciated that embodiments may be variously combined or separated without parting from the scope of the present disclosure. It is intended that the present disclosure be limited only to the extent required by the appended claims and the applicable rules of law.

As utilized herein, the terms "comprise" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art. The use of the terminology X "or" Y herein should be interpreted as meaning either "X" or "Y" individually, or both "X and Y" together.

All patents and publications mentioned in this specification are herein incorporated by reference to the same extent as if each independent patent and publication was specifically and individually indicated to be incorporated by reference.

It is also to be understood that the following claims are to cover all generic and specific features of the disclosure described herein, and all statements of the scope of the disclosure which, as a matter of language, might be said to fall therebetween.

What is claimed is:

1. An infusion delivery device comprising:
   a fluid reservoir having a proximal end, a distal end, and a plunger disposed inside the fluid reservoir and moveable therein;
   a fluid path in fluid communication with the fluid reservoir;
   at least one pressure sensor interfacing at least one of the fluid reservoir or the fluid path; and
   a processor in communication with the at least one pressure sensor and a non-transitory computer-readable medium having encoded thereon instructions that, when executed by the processor, cause the processor to:
   receive pressure data detected by the at least one pressure sensor while the fluid reservoir is being filled with a therapeutic fluid so as to translate the plunger within the fluid reservoir;

determine when a fill event has occurred at a first time based on the pressure data satisfying a threshold value; and prevent or allow operation of the infusion delivery device at a second time based on whether a difference between the second time and the first time exceeds a degradation time of the therapeutic fluid.

2. The infusion delivery device of claim 1, wherein a time stamp is saved in memory when the pressure data satisfies the threshold value.

3. The infusion delivery device of claim 1, wherein the at least one pressure sensor interfaces with the distal end of the fluid reservoir.

4. The infusion delivery device of claim 1, wherein the instructions, when executed by the processor, cause the processor to alert a user based on a predefined error code corresponding to an amount of time the infusion delivery device is in use.

5. The infusion delivery device of claim 1, wherein the instructions, when executed by the processor, cause the processor to transmit one or more notifications to a user to alert the user of an amount of time the infusion delivery device has remaining to be in use.

6. The infusion delivery device of claim 1, wherein the threshold value is pre-programmed in the non-transitory computer-readable medium.

7. The infusion delivery device of claim 1, wherein the threshold value is based on a sum of a pre-defined base pressure and a pressure measurement from the at least one pressure sensor when the infusion delivery device is first paired to a controller.

8. The infusion delivery device of claim 1, wherein the threshold value is driven by an amount of pressure required to push the plunger through the fluid reservoir.

9. A method comprising:

setting a pressure threshold of an infusion delivery device, wherein the infusion delivery device comprises:
  a fluid reservoir having a proximal end, a distal end, and a plunger disposed inside the fluid reservoir and moveable therein;
  a fluid path in fluid communication with the fluid reservoir; and
  at least one pressure sensor interfacing at least one of the fluid reservoir or the fluid path;

monitoring a pressure in the fluid reservoir or fluid path while the fluid reservoir is being filled with a therapeutic fluid;

registering a fill event when the monitored pressure exceeds the pressure threshold and recording a first time of the fill event; and preventing or allowing operation of the infusion delivery device at a second time based on whether a difference between the second time and the first time exceeds a degradation time of the therapeutic fluid.

10. The method of claim 9, further comprising causing one or more notifications to be transmitted to alert a user of an amount of time the infusion delivery device is in use.

11. The method of claim 9, further comprising causing one or more notifications to be transmitted to alert a user of an amount of time the infusion delivery device has remaining to be in use.

12. The method of claim 9, wherein the registering is performed during a time when a user is instructed to fill the infusion delivery device.

13. The method of claim 9, wherein the pressure threshold is pre-programmed in the infusion delivery device.

14. The method of claim 9, wherein the pressure threshold is based on a sum of a pre-defined constant and a pressure measurement when the infusion delivery device is first paired to a controller.

15. The method of claim 9, wherein the pressure threshold is driven by an amount of pressure required to push the plunger through the fluid reservoir.

16. An infusion management system comprising:

an infusion delivery device comprising:
  a fluid reservoir having a proximal end, a distal end, and a plunger disposed inside the fluid reservoir and moveable therein;
  a fluid path in fluid communication with the fluid reservoir;
  at least one pressure sensor interfacing at least one of the fluid reservoir or the fluid path; and
  a processor in communication with at least one pressure sensor and a non-transitory computer-readable medium having encoded thereon instructions that, when executed by the processor, cause the processor to:
    receive pressure data detected by the at least one pressure sensor while the fluid reservoir is being filled with a therapeutic fluid so as to translate the plunger within the fluid reservoir;
    determine when a fill event has occurred at a first time based on the pressure data satisfying a threshold value; and
    prevent or allow operation of the infusion delivery device at a second time based on whether a difference between the second time and the first time exceeds a degradation time of the therapeutic fluid; and
  at least one controller in communication with the infusion delivery device, wherein the at least one controller is configured to exchange data or instructions with the infusion delivery device.

17. The infusion management system of claim 16, wherein the at least one controller comprises a user interface for communicating with a user.

18. The infusion management system of claim 16, wherein the at least one controller comprises a smart phone.

19. The infusion management system of claim 16, wherein the processor is configured to transmit one or more notifications to the at least one controller.

20. The infusion management system of claim 16, wherein the at least one controller comprises a dedicated wireless remote controller.

* * * * *